(12) United States Patent
Woods et al.

(10) Patent No.: US 9,605,014 B2
(45) Date of Patent: Mar. 28, 2017

(54) GLYCOMIMETICS TO INHIBIT PATHOGEN-HOST INTERACTIONS

(71) Applicants: UNIVERSITY OF GEORGIA RESEARCH FOUNDATION, INC., Athens, GA (US); NATIONAL UNIVERSITY OF IRELAND, GALWAY, Galway (IE); GLYCOSENSORS AND DIAGNOSTICS, LLC., Athens, GA (US)

(72) Inventors: Robert J. Woods, Athens, GA (US); Paul V. Murphy, Galway (IE); Loretta Yang, San Diego, CA (US); Hannah M. K. Smith, Clare (IE); Jenifer Hendel, Alymer (CA)

(73) Assignees: University of Georgia Research Foundation, Inc., Athens, GA (US); National University of Ireland, Galway, Galway (IE); Glycosensors and Diagnostics, LLC., Athens, GA (US)

( * ) Notice: Subject to any disclaimer, the term of this patent is extended or adjusted under 35 U.S.C. 154(b) by 112 days.

(21) Appl. No.: 14/385,312

(22) PCT Filed: Mar. 14, 2013

(86) PCT No.: PCT/US2013/031238
§ 371 (c)(1),
(2) Date: Sep. 15, 2014

(87) PCT Pub. No.: WO2013/138563
PCT Pub. Date: Sep. 19, 2013

(65) Prior Publication Data
US 2015/0072952 A1    Mar. 12, 2015

Related U.S. Application Data

(60) Provisional application No. 61/611,890, filed on Mar. 16, 2012.

(51) Int. Cl.
| | | |
|---|---|---|
| *C07H 17/04* | (2006.01) |
| *C07H 15/20* | (2006.01) |
| *C07H 17/02* | (2006.01) |
| *C07H 19/01* | (2006.01) |
| *C07H 19/02* | (2006.01) |
| *C07H 19/04* | (2006.01) |
| *C07H 19/24* | (2006.01) |
| *C07H 15/04* | (2006.01) |
| *C07D 455/02* | (2006.01) |
| *G06F 19/10* | (2011.01) |

(52) U.S. Cl.
CPC ........... *C07H 17/04* (2013.01); *C07D 455/02* (2013.01); *C07H 15/04* (2013.01); *C07H 15/20* (2013.01); *C07H 17/02* (2013.01); *C07H 19/01* (2013.01); *C07H 19/02* (2013.01); *C07H 19/04* (2013.01); *C07H 19/24* (2013.01); *G06F 19/10* (2013.01)

(58) Field of Classification Search
None
See application file for complete search history.

(56) References Cited

U.S. PATENT DOCUMENTS

| | | | |
|---|---|---|---|
| 5,637,569 A * | 6/1997 | Magnusson | A61K 47/4833 514/25 |
| 6,245,902 B1 | 6/2001 | Linhardt et al. | |
| 6,664,235 B1 | 12/2003 | Kanie et al. | |
| 2006/0173199 A1 | 8/2006 | Hong et al. | |
| 2011/0257032 A1 | 10/2011 | Sasisekharan et al. | |

FOREIGN PATENT DOCUMENTS

| | | |
|---|---|---|
| WO | WO 98/31697 A1 | 6/1998 |
| WO | WO 2012/118928 A2 | 9/2012 |

OTHER PUBLICATIONS

Itzstein, Mark von, Nature Reviews, "The war against influenza: discovery and development of sialidase inhibitors", 2007, vol. 6, pp. 967-974.*
International Patent Application No. PCT/US2013/031238, filed Mar. 14, 2013; Written Opinion, issued May 30, 2013; 8 pages.
International Patent Application No. PCT/US2013/031238, filed Mar. 14, 2013; International Search Report, issued May 30, 2013; 4 pages.
International Patent Application No. PCT/US2013/031238, filed Mar. 14, 2013; International Preliminary Report on Patentability, issued Sep. 16, 2014; 10 pages.
Angström et al., "Delineation and comparison of ganglioside-binding epitopes for the toxins of Vibrio cholerae, Escherichia coli, and Clostridium tetani: evidence for overlapping epitopes" *Proc Natl Acad Sci USA*, 1994; 91(25):11859-63.
Babai et al., "New fimbrial gene cluster of S-fimbrial adhesin family" *Infect Immun*, 2000; 68(10):5901-7.
Backenson, "Borrelia burgdorferi shows specificity of binding to glycosphingolipids" *Infect Immun*, 1995; 63(8):2811-7.
Blumenschein et al., "Atomic resolution insight into host cell recognition by Toxoplasma gondii" *EMBO J*, 2007; 26(11):2808-20.
Case et al., "The Amber biomolecular simulation programs" *J Computat Chem*, 2005; 26:1668-88.

(Continued)

*Primary Examiner* — Layla Berry
*Assistant Examiner* — Bahar Craigo
(74) *Attorney, Agent, or Firm* — Mueting, Raasch & Gebhardt, P.A.

(57) ABSTRACT

The present invention relates to novel glycomimetic compounds that are rationally designed to inhibit the binding of various pathogens to cell surface sialylated galactose and methods of use thereof. Specifically sialic acid glycosides and C-glycosides are disclosed that form a lactam ring structure or a cyclic ether/amine ring structure with the adjacent monosaccharide residue.

21 Claims, 13 Drawing Sheets

(56) References Cited

OTHER PUBLICATIONS

Delorme et al., "Glycosphingolipid binding specificities of rotavirus: identification of a sialic acid-binding epitope," *J Virol*, 2001; 75(5):2276-87.
Dugan et al., "An N-linked glycoprotein with alpha(2,3)-linked sialic acid is a receptor for BK virus," *J Virol*, 2005; 79(22):14442-5.
Fadda and Woods, "Molecular simulations of carbohydrates and protein-carbohydrate interactions: motivation, issues and prospects," *Drug Discov Today*, Aug. 2010; 15(15-16):596-609.
Ford et al., "Molecular dynamics simulations of galectin-1-oligosaccharide complexes reveal the molecular basis for ligand diversity," *Proteins*, Nov. 1, 2003; 53(2):229-40.
Gonzalez-Outeiriño et al., "Reconciling solvent effects on rotamer populations in carbohydrates—A joint MD and NMR analysis" *Can J Chem*, Apr. 1, 2006;84(4):569-79.
Ha et al., "X-ray structures of H5 avian and H9 swine influenza virus hemagglutinins bound to avian and human receptor analogs" *Proc Natl Acad Sci USA*, Sep. 25, 2001; 98(20):11181-6.
Ha et al., "X-ray structure of the hemagglutinin of a potential H3 avian progenitor of the 1968 Hong Kong pandemic influenza virus," *Virology*, May 10, 2003; 309(2):209-18.
Idänpään-Heikkilä et al., "Oligosaccharides interfere with the establishment and progression of experimental pneumococcal pneumonia," *J Infect Dis*, 1997; 176(3):704-12.
Itzstein, "The war against influenza: discovery and development of sialidase inhibitors" Nature reviews—drug discovery, Dec. 2007; 6:967-74. [retrieved on Aug. 5, 2016] from the Internet. Retrieved from the Internet:<URL:http://www.cmbi.ru.nl/edu/bioinf4/articles/pdf/cmc_nrd2400_Itzstein_NRDD07.pdf>; 8 pages.
Jorgensen, "Efficient drug lead discovery and optimization," *Acc Chem Res*, Jun. 16, 2009;42(6):724-33.
Kadirvelraj et al., "Understanding the bacterial polysaccharide antigenicity of *Streptococcus agalactiae* versus *Streptococcus pneumoniae*," *Proc Natl Acad Sci U S A*, May 23, 2006;103(21):8149-54.
Kirschner et al., "GLYCAM06: a generalizable biomolecular force field. Carbohydrates,"*J Comput Chem*, 2008; 29(4):622-55.
Lin et al., "The hemagglutinin structure of an avian H1N1 influenza A virus," *Virology*, Sep. 15, 2009;392(1):73-81.
Newhouse et al., "Mechanism of glycan receptor recognition and specificity switch for avian, swine, and human adapted influenza virus hemagglutinins: a molecular dynamics perspective," *J Am Chem Soc*, Dec. 2, 2009; 131(47):17430-42.
Ofek et al., "Anti-adhesion therapy of bacterial diseases: prospects and problems," *FEMS Immunol Med Microbiol*, Oct. 15, 2003; 38(3):181-91.
Roche et al., "Helicobacter pylori and complex gangliosides,"*Infect Immun*, 2004; 72(3):1519-29.
Rogers and Snyder, "High affinity binding of tetanus toxin to mammalian brain membranes," *J Biol Chem*, 1981; 256(5):2402-7.
Skehel et al., "Receptor Binding and Membrane Fusion in Virus Entry: The Influenza Hemagglutinin" Annu Rev Biochem, 2000; 69:531-69.
Wang et al., "Mechanism by which mutations at his274 alter sensitivity of influenza a virus n1 neuraminidase to oseltamivir carboxylate and zanamivir," *Antimicrob Agents Chemother*, 2002; 46(12):3809-16.
Webster et al., "Evolution and ecology of influenza A viruses," *Microbiol Rev*, 1992; 56(1):152-79.
Woods and Tessier, "Computational glycoscience: characterizing the spatial and temporal properties of glycans and glycan-protein complexes," *Curr Opin Struct Biol*, Oct. 2010; 20(5):575-83.
Yongye et al., "On achieving experimental accuracy from molecular dynamics simulations of flexible molecules: aqueous glycerol," *J Phys Chem A*, Mar. 27, 2008; 112(12):2634-9.
Bazin et al., "Regio- and Stereoselective Synthesis of beta-D-Gluco-, alpha-L-Ido-, and alpha-L-Altropyranosiduronic Acids from Delta(4)-Uronates," *J Org Chem*, Jan. 8, 1999; 64(1):144-52.

Biarnes et al., "Substrate distortion in the Michaelis complex of Bacillus 1,3-1,4-beta-glucanase. Insight from first principles molecular dynamics simulations," *J Biol Chem*, 2006, 281:1432-41.
Bloom et al., "Permissive Secondary Mutations Enable the Evolution of Influenza Oseltamivir Resistance," *Science*, 2010; 328(5983): 1272-5.
Bosques et al., "Effects of glycosylation on peptide conformation: a synergistic experimental and computational study," *J Am Chem Soc*, Jul. 14, 2004; 126(27):8421-5.
Busse et al., "Galactose-Phosphonates as Mimetics of the Sialyltransfer by Trypanosomal Sialidases," *J Carbohydrate Chem*, Jun. 1, 2007; 26(3):159-194.
Chagnault et al., "Synthesis of somatostatin mimetics based on 1-deoxynojirimycin," *ChemMedChem*, Jul. 2008; 3(7):1071-6.
Chandrasekaran et al., "Glycan topology determines human adaptation of avian H5N1 virus hemagglutinin," *Nat Biotechnol*, Jan. 2008; 26(1):107-13.
Charvatova et al., "Quantifying Protein Interface Footprinting by Hydroxyl Radical Oxidation and Molecular Dynamics Simulation: Application to Galectin-1," *J Am Soc Mass Spectrom*, Nov. 2008, 19(11):1692-705.
Cheng et al., "Convenient temporary methyl imidate protection of N-acetylglucosamine and glycosylation at O-4," *J Org Chem*, Oct. 3, 2008; 73(19):7574-9.
Chervenak et al., "Calorimetric analysis of the binding of lectins with overlapping carbohydrate-binding ligand specificities," *Biochem*, Apr. 25, 1995; 34(16):5685-95.
Connor et al., "Receptor specificity in human, avian, and equine H2 and H3 influenza virus isolates," *Virology*, Nov. 1994; 205(1): 17-23.
Cox et al., "Global epidemiology of influenza: past and present," *Annu Rev Med*, 2000; 51:407-21.
Cronin et al., "Novel synthesis of castanospermine and 1-epicastanospermine," *Org Lett*, Jun. 23, 2005; 7(13):2691-3.
Dam et al., "Thermodynamic studies of lectin-carbohydrate interactions by isothermal titration calorimetry," *Chem Rev*, Feb. 2002; 102(2):387-429.
Danieli et al., "Selective protecting group manipulations on the 1-deoxynojirimycin scaffold," *Tetrahedron*, 2007; 63:6827-34.
Desoky et al., "Preparation of trifluoroethyl- and phenyl-protected sulfates using sulfuryl imidazolium salts," *Tetrahedron*, 2011, 67(6):1281-7.
European Centre for Disease Prevention and Control, "Emergence of Seasonal Influenza Viruses Type A/H1N1 with Oseltamivir Resistance in Some European Countries at the Start of the 2007-8 Influenza Season" Interim ECDC Risk Assessment, Jan. 27, 2008; Retrieved from the Internet on Oct. 17, 2016: <URL:http://ecdc.europa.eu/en/press/Press%20Releases/080127_PR_Risk_assesment.pdf:>; 11 pgs.
Epand et al., "The role of the ganglioside GD1a as a receptor for Sendai virus," *Biochem*, Jan. 24, 1995; 34(3):1084-9.
Ernst et al., "From carbohydrate leads to glycomimetic drugs," *Nat Rev Drug Discov*, Aug. 2009; 8(8):661-77.
Ferraris et al., "Mutations of neuraminidase implicated in neuraminidase inhibitors resistance," *J Clin Virol*, Jan. 2008; 41(1):13-9.
Gamblin et al., "The structure and receptor binding properties of the 1918 influenza hemagglutinin," *Science*, Mar. 19, 2004; 303(5665):1838-42.
González-Outeiriño et al., "The structure and conformational behavior of sulfonium salt glycosidase inhibitors in solution: a combined quantum mechanical NMR approach," *J Am Chem Soc*, Jun. 9, 2004; 126(22):6866-7.
González-Outeiriño et al., "Structural elucidation of type III group B *Streptococcus* capsular polysaccharide using molecular dynamics simulations: the role of sialic acid," *Carbohydr Res*, Apr. 11, 2005; 340(5):1007-18.
Gouin et al., "Synthesis of somatostatin mimetics based on the 1-deoxymannojirimycin scaffold," *J Org Chem*, Oct. 14, 2005; 70(21):8527-32.
Gutierrez Gallego et al., "Identification of carbohydrates binding to lectins by using surface plasmon resonance in combination with HPLC profiling," *Glycobiology*, May 2004; 14(5):373-386.

(56) References Cited

OTHER PUBLICATIONS

Hancock et al., "Cross-reactive antibody responses to the 2009 pandemic H1N1 influenza virus," *N Engl J Med*, Nov. 12, 2009; 361(20):1945-52.
Hendel et al., "Application and limitations of the methyl imidate protection strategy of N-acetylglucosamine for glycosylations at O-4: synthesis of Lewis A and Lewis X trisaccharide analogues," *Carbohydr Res*, Nov. 24, 2008; 343(17):2914-23.
Hendel et al., "How the Substituent at 0-3 of N-Acetylglucosamine Impacts Glycosylation at 0-4: A Comparative Study," *J Org Chem*, Nov. 6, 2009; 74(21):8321-31.
Hendel et al., "Computationally-Guided Design and Synthesis of Glycomimetics to Inhibit Pathogen-host Adhesion" Poster presented Mar. 19, 2012, at the International Workshop "New Approaches in Drug Design & Discovery," Schloss Rauischholzhausen, Marburg, Germany, Mar. 19-22, 2012. 1 page.
Hirakawa et al., "Construction of enzyme-substrate complexes between hen egg-white lysozyme and N-acetyl-D-glucosamine hexamer by systematic conformational search and molecular dynamics simulation," *J Biochem*, Aug. 2006; 140(2):221-7.
Humphrey et al., "VMD: visual molecular dynamics," *J Mol Graph*, Feb. 1996; 14(1):33-8, 27-8.
Imberty et al., "Structures of the lectins from *Pseudomonas aeruginosa*: insight into the molecular basis for host glycan recognition," *Microbes Infect*, Feb. 2004; 6(2):221-8.
Johnson et al., "Updating the accounts: global mortality of the 1918-1920 "Spanish" influenza pandemic," *Bull Hist Med*, 2002 Spring; 76(1):105-15.
Jorgensen, "Transferable Intermolecular Potential Functions. Application to Liquid Methanol Including Internal Rotation," *J Am Chem Soc*, 1981; 103(2):341-5.
Jorgensen et al., "Comparison of Simple Potential Functions for Simulating Liquid Water," *J Chem Phys*, Jul. 1983; 79(2):926-35.
Jorgensen, "The many roles of computation in drug discovery," *Science*, Mar. 19, 2004; 303(5665):1813-8.
Ju et al., "Supramolecular Dendrimer Capsules by Cooperative Binding," *Chem Commun (Camb)*, Jan. 7, 2011, 47(1):268-70.
Kadirvelraj et al., "Involvement of Water in Carbohydrate-Protein Binding: Concanavalin A Revisited," *J Am Chem Soc*, 2008; 130:16933-42.
Kandun et al., "Three Indonesian clusters of H5N1 virus infection in 2005" *N Engl J Med*, Nov. 23, 2006; 355(21):2186-94.
Karlsson, "Microbial recognition of target-cell glycoconjugates," *Curr Opin Struct Biol*, Oct. 1995; 5(5):622-35.
Karplus and Kushick, "Method for estimating the configurational entropy of macromolecules," *Macromolecules*, 1981; 14(2):325-32.
Kim et al., "Neuraminidase inhibitors as anti-influenza virus agents," *Antivir Chem and Chemoth*, 1999, 10:141-5.
Kim et al., "Structure-activity relationship studies of novel carbocyclic influenza neuraminidase inhibitors," *J Med Chem*, Jul. 2, 1998; 41(14):2451-60.
Kitamura et al., "Interaction between Clostridium botulinum neurotoxin and gangliosides," *Biochim Biophys Acta*, Mar. 20, 1980; 628(3):328-35.
Kohata et al., "Synthetic mucin fragments: methyl 3-O-(2-acetamido-2-deoxy-beta-D-galactopyranosyl-beta-D-3-O-(2-acetamido-2-deoxy-3-O-beta-D-galactopyranosyl-beta-D-glucopyranosyl)-beta-D-galactoyranoside. pyranosyl)-beta-D-galactopyranoside," *Carbohydr Res*, Sep. 1, 1984; 132(1):127-35.
Kollman et al., "Calculating structures and free energies of complex molecules: combining molecular mechanics and continuum models," *Acc Chem Res*, Dec. 2000; 33(12):889-97.
Kosaki et al., "Ganglioside GT1b as a complementary receptor component for Clostridium botulinum neurotoxins," *Microb Pathog*, Aug. 1998; 25(2):91-9.
Llinares and Roy, "Multivalent neoglycoconjugates: solid-phase synthesis of N-linked α-sialodendrimers," *Chemical Communications*, 1997; 21:2119-2120.
Lommerse et al., "Conformational analysis of two xylose-containing N-glycans in aqueous solution by using 1H NMR ROESY and NOESY spectroscopy in combination with MD simulations," *Carbohydr Res*, Nov. 19, 2002; 337(21-23):2279-99.
Lycknert et al., "Solution structure of a type 1 H Antigen trisaccharide at a micellar surface. NMR relaxation and molecular dynamics simulation studies," *J Phys Chem B*, 2002; 106:5275-5280.
Lycknert et al., "A conformational study of alpha-D-Manp-(1→2)-alpha-D-Manp-(1→O)-L-Ser by NMR 1H,1H T-ROESY experiments and molecular-dynamics simulations," *Carbohydr Res*, May 17, 2004; 339(7):1331-8.
Maehr, "A proposed new convention for graphic presentation of molecular geometry and topography," *J Chem Educ*, Feb. 1985; 62(2):114-120.
Malapelle et al., "An Expeditious Synthesis of N-Acetylneuraminic Acid α-C-Glycosyl Derivatives ("α-C-Glycosides") from the Anomeric Acetates," *Eur J Org Chem*, Jul. 2007; 19:3145-57.
Malapelle et al., "Anomeric Samarium(III) Intermediates of N-Acetylneuraminic Acid from Anomeric 2-Pyridylsulfides," *Heterocycles*, 2009; 77(2):1417-1424. Published online Oct. 27, 2008.
Marcaurelle and Seeberger, "Combinatorial carbohydrate chemistry," *Curr Opin Chem Biol*, Jun. 2002; 6(3):289-96.
McDonnell et al., "A general synthesis of iminosugars," *J Org Chem*, May 14, 2004; 69(10):3565-8.
McKimm-Breschkin, "Resistance of influenza viruses to neuraminidase inhibitors—a review," *Antiviral Res*, 2000; 47(1):1-17.
Miller et al., "MMPBSA.py: An Efficient Program for End-State Free Energy Calculations," *J Chem Theory Comput*, Sep. 11, 2012; 8(9):3314-21.
Okamoto et al., "Efficient synthesis of MUC4 sialylglycopeptide through the new sialylation using 5-acetamido-neuraminamide donors," *J Org Chem*, May 2, 2008; 73(9):3460-6.
Pathiaseril and Woods, "Relative energies of binding for antibody-carbohydrate-antigen complexes computed from free-energy simulations," *J Am Chem Soc*, 2000, 122(2):331-8.
Paulsen and Tietz, "Synthese eines trisaccharides aus N-acetylneuraminsäure und N-acetyllactosamin," *Carbohydr Res*, Jan. 10, 1984; 125(1):47-64.
Paulsen et al., "Only the trivial alkyl and hydroxymethyl C-glycosides of Neu5Ac have been synthesized," *Liebigs Ann Chem*, 1991; 487-495.
Pedatella et al., "New sialyl Lewisx mimic containing an α-substituted β3-amino acid spacer," *Carbohydr Res*, Jan. 14, 2008; 343(1):31-8.
Pettersen et al., "UCSF Chimera—a visualization system for exploratory research and analysis," *J Comput Chem*, Oct. 2004; 25(13):1605-12.
Rajagopal and Treanor, "Pandemic (avian) influenza," *Semin Respir Crit Care Med*, Apr. 2007; 28(2):159-70.
Rothermel et al., "Synthesis of α-N-Ketosides of N-Acetylneuraminic Acid by Using Phase-Transfer Catalysis," *EurJOC*, Aug. 12, 1992; 8:799-802.
Roy et al., "Solid-phase synthesis of dendritic sialoside inhibitors of influenza A virus haemagglutinin," *J Chem Soc, Chem Commun*, 1993, 24:1869-1872.
Sambhara and Poland, "H5N1 Avian influenza: preventive and therapeutic strategies against a pandemic," *Annu Rev Med*, 2010; 61:187-98.
Sakarya and Oncü, "Bacterial adhesins and the role of sialic acid in bacterial adhesion," *Med Sci Monit*, Mar. 2003; 9(3):RA76-82.
Skehel and Wiley, "Receptor Binding and Membrane Fusion in Virus Entry: The Influenza Hemagglutinin," *Annu Rev Biochem*, 2000; 69:531-69.
Sharon, "Bacterial lectins, cell-cell recognition and infectious disease," *FEBS Lett*, Jun. 15, 1987; 217(2):145-57.
Sharon, "Carbohydrates as future anti-adhesion drugs for infectious diseases," *Biochem Biophys Acta*, Apr. 2006; 1760(4):527-37.
Simon, "Pharmaceutical oligosaccharides," *Drug Disc Today*, Dec. 1996; 1(12):522-528.
Simon et al., "Inhibition of *Helicobacter pylori* Binding to Gastrointestinal Epithelial Cells by Sialic Acid-Containing Oligosaccharides," *Infection Immun*, Feb. 1997; 65 (2):750-7.

(56) References Cited

OTHER PUBLICATIONS

Smid et al., "Synthesis, structure-activity relationships, and biological properties of 1-heteroaryl-4-[omega-(1H-indol-3-yl)alkyl]piperazines, novel potential antipsychotics combining potent dopamine D2 receptor antagonism with potent serotonin reuptake inhibition," *J Med Chem*, Nov. 3, 2005; 48(22):6855-69.
Sola et al., "Influence of modulated structural dynamics on the kinetics of alpha-chymotrypsin catalysis. Insights through chemical glycosylation, molecular dynamics and domain motion analysis," *FEBS J*, Dec. 2006; 273(23):5303-19.
Stevens et al., "Glycan microarray technologies: tools to survey host specificity of influenza viruses," *Nat Rev Microbiol*, Nov. 2006; 4(11):857-64.
Sudha et al., "Adherence of Shigella dysenteriae 1 to human colonic mucin," *Curr Microbiol*, Jun. 2001; 42(6):381-7.
Taubenberger and Morens, "1918 Influenza: the mother of all pandemics," *Emerg Infect Dis*, Jan. 2006; 12(1):15-22.
Tempel et al., "The xenograft antigen bound to Griffonia simplicifolia lectin 1-B(4). X-ray crystal structure of the complex and molecular dynamics characterization of the binding site," *J Biol Chem*, Feb. 22, 2002; 277(8):6615-21.
Tsuchida et al., "Simple synthesis of sialyllactose-carrying polystyrene and its binding with influenza virus," *Glycoconj J*, Nov. 1998; 15(11):1047-54.
Tumpey et al., "A Two-Amino Acid Change in the Hemagglutinin of the 1918 Influenza Virus Abolishes Transmission," *Science*, Feb. 2, 2007; 315(5812):655-9.
Turnbull et al., "Dissecting the cholera toxin-ganglioside GM1 interaction by isothermal titration calorimetry," *J Am Chem Soc*, Feb. 4, 2004; 126(4):1047-54.
Umemura et al., "One-step synthesis of efficient binding-inhibitor for influenza virus through multiple addition of sialyloligosaccharides on chitosan," *Carbohydrate Polymers*, Jun. 11, 2010; 81(2):330-4.
Ungchusak et al., "Probable person-to-person transmission of avian influenza A (H5N1)," *N Engl J Med*, Jan. 27, 2005; 352(4):333-40.
Varki and Varki, "Diversity in cell surface sialic acid presentations: implications for biology and disease," *Lab Invest*, Sep. 2007; 87(9):851-7.
von Itzstein et al., "Rational design of potent sialidase-based inhibitors of influenza virus replication," *Nature*, Jun. 3, 1993; 363(6428):418-23.
Wade, "'Flu' and structure-based drug-design," *Structure*, 1997; 5(9):1139-45.
Wang et al., "Inhibition of Neuraminidase with Neuraminic Acid C-Glycosides," *Bioorganic Med Chem Letters*, 2000; 10:941-4.
Wang et al., "Probable limited person-to-person transmission of highly pathogenic avian influenza A (H5N1) virus in China," *Lancet*, Apr. 26, 2008; 371(9622):1427-34.
Wang et al., "Convergent syntheses of Le analogues," *Beilstein J Org Chem*, Feb. 22, 2010; 6:17.
Weisser and Hall, "Applications of single-chain variable fragment antibodies in therapeutics and diagnostics," *Biotechnology Advances*, Jul.-Aug. 2009; 27(4):502-20.
Weisser et al., "A rAb screening method for improving the probability of identifying peptide mimotopes of carbohydrate antigens," *Vaccine*, Jun. 6, 2007; 25(23):4611-22.
Werz et al., "Automated synthesis of the tumor-associated carbohydrate antigens Gb-3 and Globo-H: incorporation of alpha-galactosidic linkages," *J Am Chem Soc*, Mar. 14, 2007; 129(10):2770-1.
World Health Organization (WHO), "Weekly Epidemiological Record—Human cases of avian influenza A (H5N1) in north-west frontier province, Pakistan, Oct.-Nov. 2007" 2008, 83(40):357-64. Retrieved from the Internet on Oct. 17, 2016: <URL:http://www.who.int/wer/2008/wer8340.pdf?ua=1>.
Woods et al., "Glycam_93: A generalized parameter set for molecular dynamics simulations of glycoproteins and oligosaccharides. Application to the structure and dynamics of a disaccharide related to oligomannose" in *Complex Carbohydrates in Drug Research*. Bock et al., (Eds) Alfred Benzon Symposium No. 36: Munksgaard, Copenhagen; 1993. pp. 15-26.
Wong and Yuen, "Avian influenza virus infections in humans," *Chest*, Jan. 2006; 129(1):156-68.
Xie et al., "Complexes with anti-epitope tag IgGs improve the therapeutic potential of epitope-tagged antibody fragments," *Molecular Immunology*, Apr. 2010; 47(7-8):1529-34.
Yan et al., "Multiplexed flow cytometric immunoassay for influenza virus detection and differentiation," *Anal Chem*, Dec. 1, 2005; 77(23):7673-8.
Zhao et al., "Hybrids of 1-deoxynojirimycin and aryl-1,2,3-triazoles and biological studies related to angiogenesis," *Bioorg Med Chem*, Jun. 15, 2008; 16(12):6333-7.
Zhou and Murphy, "New access to 1-deoxynojirimycin derivatives via azide-alkene cycloaddition," *Org Lett*, Sep. 4, 2008; 10(17):3777-80.

\* cited by examiner

Scheme 1. Preliminary synthetic steps toward the scaffold synthesis

Retrosynthetic analysis: Approach No. 1 to influenza inhibitor 1

Proposed synthesis of 1 from 2 and 3: Approach 1

Proposed synthesis of 1 from 2 and 4: Route 2

Scheme 2. Proposed synthetic routes to glycomimetic 1.

Type I

Type II

Type III

Type IV

Type V

GLYCOMIMETICS TO INHIBIT PATHOGEN-HOST INTERACTIONS

CONTINUING APPLICATION DATA

This application is the §371 U.S. National Stage of International Application No. PCT/US2013/031238, filed 14 Mar. 2013, which claims the benefit of U.S. Provisional Application Ser. No. 61/611,890, filed Mar. 16, 2012, which are incorporated by reference herein in their entireties.

BACKGROUND

The influenza virus remains a worldwide cause of sickness and death in humans (Rajagopal and Treanor, 2007, *Semin Respir Crit Care Med*; 28:159-170). Seasonal flu is estimated to kill approximately 36000 annually, despite widespread vaccination programs. Historically, there are an average of three influenza pandemics every century (Cox and Subbarao, 2000, *Annu Rev Med*; 51:407-421). It is estimated that the 1918 "Spanish Flu" pandemic killed up to 50 million worldwide (Johnson and Mueller, 2002, *Bull Hist Med*; 76:105-115). More recently, the 1957 "Asian Flu" and 1968 "Hong Kong Flu" pandemics resulted in up to 1 million and 700,000 deaths, respectively (Rajagopal and Treanor, 2007, *Semin Respir Crit Care Med*; 28(2):159-170). The "Swine Flu" outbreak of 2009, although relatively mild, spread alarmingly rapidly and led to a global awareness that there is a significant lag time associated with vaccine production. Recently, the transfer of the avian flu virus (H5N1) to humans has been documented. Current reports suggest the virus is mutating and when human-to-human transfer begins, the level of international travel could help foster a pandemic in a matter of weeks (Cox and Subbarao, 2000, *Annu Rev Med*; 51:407-421). The formulation of a vaccine to protect against pandemic flu is unlikely achievable until the exact virus strain has been identified. Once identified, it takes approximately 6 months to make the vaccine available (Sambhara and Poland, 2010, *Annu Rev Med*; 61:187-198). Current epidemiological models project that an influenza pandemic could result in 7.4 million deaths globally. Thus there is a need for new and improved agents and methods for the prevention and treatment of influenza, including pandemic influenza.

SUMMARY OF THE INVENTION

The present invention includes a glycomimetic compound having the formula of Type I

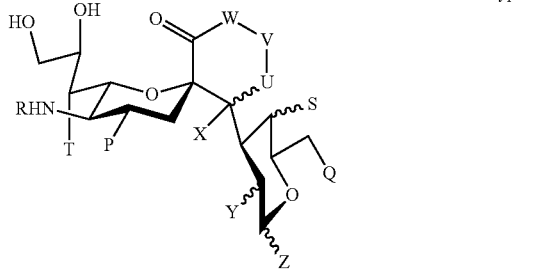

Type I and pharmaceutically acceptable salts, esters, intermediate, solvates, hydrates and multivalent versions thereof, wherein:

P is independently selected from the group consisting of a halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and $C_6$-$C_{20}$ aryl ester;

Q is independently selected from the group consisting of a halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and $C_6$-$C_{20}$ aryl ester;

R is independently selected from the group consisting of H, $C_1$-$C_5$ aliphatic ester, $C(O)CF_3$, triazole, and azide;

S is independently selected from the group consisting of an axial or equatorial halogen, OH, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and $C_6$-$C_{20}$ aryl ester;

T is independently selected from the group consisting of a halogen, OH, H, $C_1$-$C_5$ aliphatic ether, $C_1$-$C_5$ aliphatic thioether, $NH_2$, $C_1$-$C_5$ aliphatic amine, $C_1$-$C_5$ aryl amine, $C_5$-$C_{10}$ aryl ether, $C_1$-$C_{20}$ aliphatic ester, and $C_6$-$C_{20}$ aryl ester;

U is independently selected from the group consisting of $C_1$-$C_5$ aliphatic, O, NH, S, and $C_1$-$C_5$ aliphatic amine;

V is independently selected from a $C_1$-$C_5$ aliphatic;

W is independently selected from the group consisting of $C_1$-$C_5$ aliphatic, O, NH, S, and $C_1$-$C_5$ aliphatic amine;

X is independently selected from the group consisting of H, OH, halogen $C_1$-$C_5$ aliphatic ester, $C_1$-$C_5$ aliphatic ether, $C_5$-$C_{10}$ arylether, $C_1$-$C_{20}$ aliphatic ester, and $C_6$-$C_{20}$ aryl ester;

Y is independently selected from the group consisting of an axial or equatorial halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_5$ aliphatic amide, $C_1$-$C_5$ aryl amine, $C_5$-$C_{10}$ arylether, $C_1$-$C_{20}$ aliphatic ester, and $C_6$-$C_{20}$ aryl ester; and Z is independently selected from the group consisting of $C_1$-$C_5$ aliphatic, $C_1$-$C_{20}$ aryl, $C_1$-$C_{20}$ aliphatic ether, $C_1$-$C_{10}$ aliphatic thioether, $NH_2$, $C_1$-$C_5$ aliphatic amine, $C_1$-$C_5$ aryl amine, $C_1$-$C_{20}$ aliphatic ester, $C_6$-$C_{20}$ aryl ether, and a monosaccharide.

In some embodiments, P is selected from H, OH, halogen $C_1$-$C_5$ aliphatic ester, $C_1$-$C_5$ aliphatic ether, $C_5$-$C_{10}$ arylether, $C_1$-$C_{20}$ aliphatic ester, $C_6$-$C_{20}$ aryl ester, halogen, $OCH_3$, OBenzyl, or OCyclohexyl; U is O or $CH_2$; V=$CH_2$; W=NH; X=H; Y=equatorial OH; Z=$OCH_3$, S=axial OH; R=Ac ($CH_3C$=O); T=OH; and Q=OH.

In some embodiments, U is selected from $C_1$-$C_5$ aliphatic, O, NH, S, and $C_1$-$C_5$ aliphatic amine; V=$CH_2$; W=NH; X=H; Y=equatorial OH; Z=$OCH_3$, S=axial OH; R=Ac ($CH_3C$=O); T=OH; Q=OH; and P=OH.

In some embodiments, U is O or $CH_2$; V is selected from $C_1$-$C_5$ aliphatic; W=NH; X=H or OH; Y=equatorial OH; S=axial OH; R=Ac ($CH_3C$=O); T=OH; Q=OH; P=OH; and Z=$OCH_3$.

In some embodiments, U=O or $CH_2$; V=$CH_2$; W is selected from $C_1$-$C_5$ aliphatic, O, NH, S, and $C_1$-$C_5$ aliphatic amine; X=H or OH; Y=equatorial OH; S=axial OH; R=Ac ($CH_3C$=O); T=OH; Q=OH; Z=$OCH_3$; and P=OH.

In some embodiments, U=O or $CH_2$; V=$CH_2$; W=NH; X is selected from H, OH, halogen $C_1$-$C_5$ aliphatic ester, $C_1$-$C_5$ aliphatic ether, $C_5$-$C_{10}$ arylether, $C_1$-$C_{20}$ aliphatic ester, $C_6$-$C_{20}$ aryl ester, halogen, $OCH_3$, OBenzyl, or OCyclohexyl; Y=equatorial OH; S=axial OH; R=Ac ($CH_3C$=O), T=OH; Q=OH; Z=$OCH_3$; and P=OH.

In some embodiments, U=O or $CH_2$; V=$CH_2$; W=NH; X=H or OH; Y is selected from an axial or equatorial halogen, OH, CF$_3$, H, C$_1$-C$_5$ aliphatic ether, C$_1$-C$_5$ aliphatic thioether, NH$_2$, C$_1$-C$_5$ aliphatic amine, C$_1$-C$_5$ aliphatic amide, C$_1$-C$_5$ aryl amine, C$_5$-C$_{10}$ arylether, C$_1$-C$_{20}$ aliphatic ester, and C$_6$-C$_{20}$ aryl ester; and S=axial OH; R=Ac (CH$_3$C=O); T=OH; Q=OH; Z=OCH$_3$; and P=OH.

In some embodiments, U=O or CH$_2$; V=CH$_2$; W=NH; X=H or OH; Y=equatorial OH; S is selected from an axial or equatorial halogen, OH, H, C$_1$-C$_5$ aliphatic ether, C$_1$-C$_5$ aliphatic thioether, NH$_2$, C$_1$-C$_5$ aliphatic amine, C$_1$-C$_6$ aryl amine, C$_5$-C$_{10}$ aryl ether, C$_1$-C$_{20}$ aliphatic ester, and C$_6$-C$_{20}$ aryl ester; R=Ac (CH$_3$C=O); T=OH; Q=OH; Z=OCH$_3$; and P=OH.

In some embodiments, U=O or CH$_2$; V=CH$_2$; W=NH; X=H or OH; Y=equatorial OH; S=axial OH; R is selected from H, C$_1$-C$_5$ aliphatic ester, C(O)CF$_3$, substituted triazole, or azide; T=OH; Q=OH; Z=OCH$_3$; and P=OH.

In some embodiments, U=O or CH$_2$; V=CH$_2$; W=NH; X=H; Y=equatorial OH; S=axial OH; R=Ac (CH$_3$C=O), T is selected from a halogen, OH, H, C$_1$-C$_5$ aliphatic ether, C$_1$-C$_5$ aliphatic thioether, NH$_2$, C$_1$-C$_5$ aliphatic amine, C$_1$-C$_5$ aryl amine, C$_5$-C$_{10}$ aryl ether, C$_1$-C$_{20}$ aliphatic ester, or C$_6$-C$_{20}$ aryl ester; Q=OH; Z=OCH$_3$; and P=OH.

In some embodiments, U=O or CH$_2$; V=CH$_2$; W=NH; X=H; Y=equatorial OH; S=axial OH; R=Ac (CH$_3$C=O); T=OH; Q is selected a halogen, OH, CF$_3$, H, C$_1$-C$_5$ aliphatic ether, C$_1$-C$_5$ aliphatic thioether, NH$_2$, C$_1$-C$_5$ aliphatic amine, C$_1$-C$_6$ aryl amine, C$_5$-C$_{10}$ aryl ether, C$_1$-C$_{20}$ aliphatic ester, and C$_6$-C$_{20}$ aryl ester; Z=OCH$_3$; and P=OH.

In some embodiments, U=O or CH$_2$; V=CH$_2$; W=NH; X=H; Y=equatorial OH; S=axial OH; R=Ac (CH$_3$C=O); T=OH; Q=OH; P=OH; and Z is selected from C$_1$-C$_5$ aliphatic, C$_1$-C$_{20}$ aryl, C$_1$-C$_{20}$ aliphatic ether, C$_1$-C$_{10}$ aliphatic thioether, NH$_2$, C$_1$-C$_5$ aliphatic amine, C$_1$-C$_5$ aryl amine, C$_1$-C$_{20}$ aliphatic ester, C$_6$-C$_{20}$ aryl ether, and a monosaccharide.

In some embodiments, U=O or CH$_2$; V=CH$_2$; W=NH; X=H or OH; Y=equatorial OH; S=axial OH; R=Ac (CH$_3$C=O); T=OH; Q=OH; Z=OCH$_3$; and P=OH.

In some embodiments, a monosaccharide includes glucose, mannose, galactose, GlcNAc, GalNAc, and ManNAc.

The present invention includes a glycomimetic compound having the formula of Type II

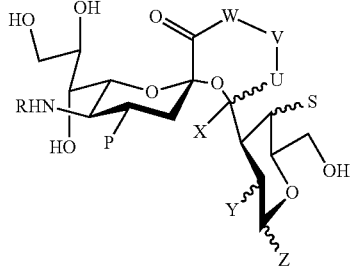

Type II and pharmaceutically acceptable salts, esters, intermediate, solvates, hydrates and multivalent versions thereof, wherein:

P is independently selected from the group consisting of a halogen, OH, CF$_3$, H, C$_1$-C$_5$ aliphatic ether, C$_1$-C$_5$ aliphatic thioether, NH$_2$, C$_1$-C$_5$ aliphatic amine, C$_1$-C$_6$ aryl amine, C$_5$-C$_{10}$ aryl ether, C$_1$-C$_{20}$ aliphatic ester, and C$_6$-C$_{20}$ aryl ester;

Q is independently selected from the group consisting of a halogen, OH, CF$_3$, H, C$_1$-C$_5$ aliphatic ether, C$_1$-C$_5$ aliphatic thioether, NH$_2$, C$_1$-C$_5$ aliphatic amine, C$_1$-C$_6$ aryl amine, C$_5$-C$_{10}$ aryl ether, C$_1$-C$_{20}$ aliphatic ester, and C$_6$-C$_{20}$ aryl ester;

R is independently selected from the group consisting of H, C$_1$-C$_5$ aliphatic ester, C(O)CF$_3$, triazole, and azide;

S is independently selected from the group consisting of an axial or equatorial halogen, OH, H, C$_1$-C$_5$ aliphatic ether, C$_1$-C$_5$ aliphatic thioether, NH$_2$, C$_1$-C$_5$ aliphatic amine, C$_1$-C$_6$ aryl amine, C$_5$-C$_{10}$ aryl ether, C$_1$-C$_{20}$ aliphatic ester, and C$_6$-C$_{20}$ aryl ester;

T is independently selected from the group consisting of a halogen, OH, H, C$_1$-C$_5$ aliphatic ether, C$_1$-C$_5$ aliphatic thioether, NH$_2$, C$_1$-C$_5$ aliphatic amine, C$_1$-C$_5$ aryl amine, C$_5$-C$_{10}$ aryl ether, C$_1$-C$_{20}$ aliphatic ester, and C$_6$-C$_{20}$ aryl ester;

U is independently selected from the group consisting of a C$_1$-C$_5$ aliphatic, O, NH, S, and a C$_1$-C$_5$ aliphatic amine;

V is independently selected from the group consisting of a C$_1$-C$_5$ aliphatic;

W is independently selected from the group consisting of a C$_1$-C$_5$ aliphatic, O, NH, S, and a C$_1$-C$_5$ aliphatic amine;

X is independently selected from the group consisting of H, OH, halogen C$_1$-C$_5$ aliphatic ester, C$_1$-C$_5$ aliphatic ether, C$_5$-C$_{10}$ arylether, C$_1$-C$_{20}$ aliphatic ester, and C$_6$-C$_{20}$ aryl ester;

Y is independently selected from the group consisting of an axial or equatorial halogen, OH, CF$_3$, H, C$_1$-C$_5$ aliphatic ether, C$_1$-C$_5$ aliphatic thioether, NH$_2$, C$_1$-C$_5$ aliphatic amine, C$_1$-C$_5$ aliphatic amide, C$_1$-C$_5$ aryl amine, C$_5$-C$_{10}$ arylether, C$_1$-C$_{20}$ aliphatic ester, and C$_6$-C$_{20}$ aryl ester; and Z is independently selected from the group consisting of C$_1$-C$_5$ aliphatic, C$_1$-C$_{20}$ aryl, C$_1$-C$_{20}$ aliphatic ether, C$_1$-C$_{10}$ aliphatic thioether, NH$_2$, C$_1$-C$_5$ aliphatic amine, C$_1$-C$_5$ aryl amine, C$_1$-C$_{20}$ aliphatic ester, C$_6$-C$_{20}$ aryl ether, and a monosaccharide.

In some embodiments, P is selected from H, OH, halogen C$_1$-C$_5$ aliphatic ester, C$_1$-C$_5$ aliphatic ether, C$_5$-C$_{10}$ arylether, C$_1$-C$_{20}$ aliphatic ester, C$_6$-C$_{20}$ aryl ester, halogen, OCH$_3$, OBenzyl, or OCyclohexyl; U is O or CH$_2$; V=CH2; W=NH; X=H; Y=equatorial OH; Z=OCH3, S=axial OH; R=Ac (CH3C=O); T=OH; and Q=OH.

In some embodiments, U is selected from C$_1$-C$_5$ aliphatic, O, NH, S, or C$_1$-C$_5$ aliphatic amine; V=CH$_2$; W=NH; X=H; Y=equatorial OH; Z=OCH$_3$, S=axial OH; R=Ac (CH$_3$C=O); T=OH; Q=OH; and P=OH.

In some embodiments, U is O or CH$_2$; V is selected from a C$_1$-C$_5$ aliphatic; W=NH; X=H or OH; Y=equatorial OH; S=axial OH; R=Ac (CH$_3$C=O); T=OH; Q=OH; P=OH; and Z=OCH$_3$.

In some embodiments, U=O or CH$_2$; V=CH$_2$; W is selected from C$_1$-C$_5$ aliphatic, O, NH, S, or a C$_1$-C$_5$ aliphatic amine; X=H or OH; Y=equatorial OH; S=axial OH; R=Ac (CH$_3$C=O); T=OH; Q=OH; Z=OCH$_3$; and P=OH.

In some embodiments, U=O or CH$_2$; V=CH$_2$; W=NH; X is selected from H, OH, halogen C$_1$-C$_5$ aliphatic ester, C$_1$-C$_5$ aliphatic ether, C$_5$-C$_{10}$ arylether, C$_1$-C$_{20}$ aliphatic ester, C$_6$-C$_{20}$ aryl ester, halogen, OCH$_3$, OBenzyl, or OCyclohexyl; Y=equatorial OH; S=axial OH; R=Ac (CH$_3$C=O); T=OH; Q=OH; Z=OCH$_3$; and P=OH.

In some embodiments, U=O or CH$_2$; V=CH$_2$; W=NH; X=H or OH; Y is selected from an axial or equatorial halogen, OH, CF$_3$, H, C$_1$-C$_5$ aliphatic ether, C$_1$-C$_5$ aliphatic thioether, NH$_2$, C$_1$-C$_5$ aliphatic amine, C$_1$-C$_5$ aliphatic amide, C$_1$-C$_5$ aryl amine, C$_5$-C$_{10}$ arylether, C$_1$-C$_{20}$ aliphatic ester, or a C$_6$-C$_{20}$ aryl ester; S=axial OH; R=Ac (CH$_3$C=O); T=OH; Q=OH; Z=OCH$_3$; and P=OH.

In some embodiments, U=O or CH$_2$; V=CH$_2$; W=NH; X=H or OH; Y=equatorial OH; S is selected from an axial or equatorial halogen, OH, H, C$_1$-C$_5$ aliphatic ether, C$_1$-C$_5$ aliphatic thioether, NH$_2$, C$_1$-C$_5$ aliphatic amine, C$_1$-C$_6$ aryl amine, C$_5$-C$_{10}$ aryl ether, C$_1$-C$_{20}$ aliphatic ester, or an C$_6$-C$_{20}$ aryl ester; R=Ac (CH$_3$C=O), T=OH; Q=OH; Z=OCH$_3$; and P=OH.

In some embodiments, U=O or CH$_2$; V=CH$_2$; W=NH; X=H or OH; Y=equatorial OH; S=axial OH; R is selected from H, C$_1$-C$_5$ aliphatic ester, C(O)CF$_3$, substituted triazole, or azide; T=OH; Q=OH; Z=OCH$_3$; and P=OH.

In some embodiments, U=O or CH$_2$; V=CH$_2$; W=NH; X=H; Y=equatorial OH; S=axial OH; R=Ac (CH$_3$C=O); T is selected from a halogen, OH, H, C$_1$-C$_5$ aliphatic ether, C$_1$-C$_5$ aliphatic thioether, NH$_2$, C$_1$-C$_5$ aliphatic amine, C$_1$-C$_5$ aryl amine, C$_5$-C$_{10}$ aryl ether, C$_1$-C$_{20}$ aliphatic ester, or a C$_6$-C$_{20}$ aryl ester; Q=OH; Z=OCH$_3$; and P=OH.

In some embodiments, U=O or CH$_2$; V=CH$_2$; W=NH; X=H; Y=equatorial OH; S=axial OH; R=Ac (CH$_3$C=O); T=OH; Q is selected from a halogen, OH, CF$_3$, H, C$_1$-C$_5$ aliphatic ether, C$_1$-C$_5$ aliphatic thioether, NH$_2$, C$_1$-C$_5$ aliphatic amine, C$_1$-C$_6$ aryl amine, C$_5$-C$_{10}$ aryl ether, C$_1$-C$_{20}$ aliphatic ester, or a C$_6$-C$_{20}$ aryl ester; Z=OCH$_3$; and P=OH.

In some embodiments, U=O or CH$_2$; V=CH$_2$; W=NH; X=H; Y=equatorial OH; S=axial OH; R=Ac (CH$_3$C=O); T=OH; Q=OH; P=OH; Z is selected from C$_1$-C$_5$ aliphatic, C$_1$-C$_{20}$ aryl, C$_1$-C$_{20}$ aliphatic ether, C$_1$-C$_{10}$ aliphatic thioether, NH$_2$, C$_1$-C$_5$ aliphatic amine, C$_1$-C$_5$ aryl amine, C$_1$-C$_{20}$ aliphatic ester, C$_6$-C$_{20}$ aryl ether, or a monosaccharide.

In some embodiments, U=O or CH$_2$; V=CH$_2$; W=NH; X=H or OH; Y=equatorial OH; S=axial OH; R=Ac (CH$_3$C=O); T=OH; Q=OH; Z=OCH$_3$; and P=OH.

In some embodiments, a monosaccharide includes glucose, mannose, galactose, GlcNAc, GalNAc, or ManNAc.

The present invention includes a glycomimetic compound having the formula of Type III

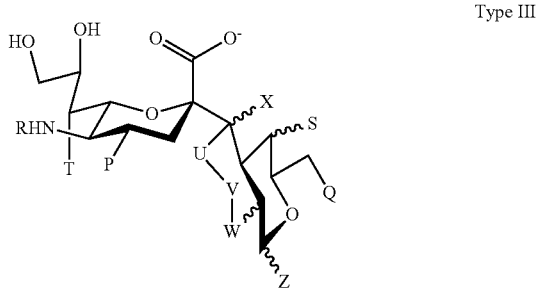

Type III and pharmaceutically acceptable salts, esters, intermediate, solvates, hydrates and multivalent versions thereof, wherein:

P is independently selected from the group consisting of a halogen, OH, CF$_3$, H, C$_1$-C$_5$ aliphatic ether, C$_1$-C$_5$ aliphatic thioether, NH$_2$, C$_1$-C$_5$ aliphatic amine, C$_1$-C$_6$ aryl amine, C$_5$-C$_{10}$ aryl ether, C$_1$-C$_{20}$ aliphatic ester, and C$_6$-C$_{20}$ aryl ester;

Q is independently selected from the group consisting of a halogen, OH, CF$_3$, H, C$_1$-C$_5$ aliphatic ether, C$_1$-C$_5$ aliphatic thioether, NH$_2$, C$_1$-C$_5$ aliphatic amine, C$_1$-C$_6$ aryl amine, C$_5$-C$_{10}$ aryl ether, C$_1$-C$_{20}$ aliphatic ester, and C$_6$-C$_{20}$ aryl ester;

R is independently selected from H, C$_1$-C$_5$ aliphatic ester, C(O)CF$_3$, triazole, and azide;

S is independently selected from the group consisting of an axial or equatorial halogen, OH, H, C$_1$-C$_5$ aliphatic ether, C$_1$-C$_5$ aliphatic thioether, NH$_2$, C$_1$-C$_5$ aliphatic amine, C$_1$-C$_6$ aryl amine, C$_5$-C$_{10}$ aryl ether, C$_1$-C$_{20}$ aliphatic ester, and C$_6$-C$_{20}$ aryl ester;

T is independently selected from the group consisting of a halogen, OH, H, C$_1$-C$_5$ aliphatic ether, C$_1$-C$_5$ aliphatic thioether, NH$_2$, C$_1$-C$_5$ aliphatic amine, C$_1$-C$_5$ aryl amine, C$_5$-C$_{10}$ aryl ether, C$_1$-C$_{20}$ aliphatic ester, and C$_6$-C$_{20}$ aryl ester;

U is independently selected from C$_1$-C$_5$ aliphatic, O, NH, S, and C$_1$-C$_5$ aliphatic amine;

V is independently selected from a C$_1$-C$_5$ aliphatic;

W is independently selected from C$_1$-C$_5$ aliphatic, O, NH, S, and C$_1$-C$_5$ aliphatic amine;

X is independently selected from H, OH, halogen C$_1$-C$_5$ aliphatic ester, C$_1$-C$_5$ aliphatic ether, C$_5$-C$_{10}$ arylether, C$_1$-C$_{20}$ aliphatic ester, and C$_6$-C$_{20}$ aryl ester; and Z is independently selected from C$_1$-C$_5$ aliphatic, C$_1$-C$_{20}$ aryl, C$_1$-C$_{20}$ aliphatic ether, C$_1$-C$_{10}$ aliphatic thioether, NH$_2$, C$_1$-C$_5$ aliphatic amine, C$_1$-C$_5$ aryl amine, C$_1$-C$_{20}$ aliphatic ester, C$_6$-C$_{20}$ aryl ether, and a monosaccharide.

In some embodiments, P is H, OH, halogen C$_1$-C$_5$ aliphatic ester, C$_1$-C$_5$ aliphatic ether, C$_5$-C$_{10}$ arylether, C$_1$-C$_{20}$ aliphatic ester, C$_6$-C$_{20}$ aryl ester, halogen, OCH$_3$, OBenzyl, and OCyclohexyl; U is O or CH$_2$; V=CH2; W=NH; X=H; Z=OCH3, S=axial OH; R=Ac (CH3C=O); T=OH; and Q=OH.

In some embodiments, U is selected from C$_1$-C$_5$ aliphatic, O, NH, S, or a C$_1$-C$_5$ aliphatic amine; V=CH$_2$; W=NH; X=H; Z=OCH$_3$, S=axial OH; R=Ac (CH$_3$C=O); T=OH; Q=OH; and P=OH.

In some embodiments, U is O or CH$_2$; V is selected from a C$_1$-C$_5$ aliphatic; W=NH; X=H or OH; S=axial OH; R=Ac (CH$_3$C=O); T=OH; Q=OH; P=OH; and Z=OCH$_3$.

In some embodiments, U=O or CH$_2$; V=CH$_2$; W is selected from C$_1$-C$_5$ aliphatic, O, NH, S, or a C$_1$-C$_5$ aliphatic amine; X=H or OH; S=axial OH; R=Ac (CH$_3$C=O); T=OH; Q=OH; Z=OCH$_3$; and P=OH.

In some embodiments, U=O or CH$_2$; V=CH$_2$; W=NH; X is selected from H, OH, halogen C$_1$-C$_5$ aliphatic ester, C$_1$-C$_5$ aliphatic ether, C$_5$-C$_{10}$ arylether, C$_1$-C$_{20}$ aliphatic ester, C$_6$-C$_{20}$ aryl ester, halogen, OCH$_3$, OBenzyl, or OCyclohexyl; S=axial OH; R=Ac (CH$_3$C=O), T=OH; Q=OH; Z=OCH$_3$; and P=OH.

In some embodiments, U=O or CH$_2$; V=CH$_2$; W=NH; X=H or OH; S is selected from an axial or equatorial halogen, OH, H, C$_1$-C$_5$ aliphatic ether, C$_1$-C$_5$ aliphatic thioether, NH$_2$, C$_1$-C$_5$ aliphatic amine, C$_1$-C$_6$ aryl amine, C$_5$-C$_{10}$ aryl ether, C$_1$-C$_{20}$ aliphatic ester, or a C$_6$-C$_{20}$ aryl ester; R=Ac (CH$_3$C=O), T=OH; Q=OH; Z=OCH$_3$; and P=OH.

In some embodiments, U=O or CH$_2$; V=CH$_2$; W=NH; X=H or OH; S=axial OH; R is selected from H, C$_1$-C$_5$ aliphatic ester, C(O)CF$_3$, substituted triazole, or azide; T=OH; Q=OH; Z=OCH$_3$; and P=OH.

In some embodiments, U=O or CH$_2$; V=CH$_2$; W=NH; X=H; S=axial OH; R=Ac (CH$_3$C=O), T is selected from a halogen, OH, H, C$_1$-C$_5$ aliphatic ether, C$_1$-C$_5$ aliphatic thioether, NH$_2$, C$_1$-C$_5$ aliphatic amine, C$_1$-C$_5$ aryl amine, C$_5$-C$_{10}$ aryl ether, C$_1$-C$_{20}$ aliphatic ester, or a C$_6$-C$_{20}$ aryl ester; Q=OH; Z=OCH$_3$; and P=OH.

In some embodiments, U=O or CH$_2$; V=CH$_2$; W=NH; X=H; S=axial OH; R=Ac (CH$_3$C=O); T=OH; Q is selected from a halogen, OH, CF$_3$, H, C$_1$-C$_5$ aliphatic ether, C$_1$-C$_5$ aliphatic thioether, NH$_2$, C$_1$-C$_5$ aliphatic amine, C$_1$-C$_6$ aryl amine, C$_5$-C$_{10}$ aryl ether, C$_1$-C$_{20}$ aliphatic ester, or a C$_6$-C$_{20}$ aryl ester; Z=OCH$_3$; and P=OH.

In some embodiments, U=O or CH$_2$; V=CH$_2$; W=NH; X=H; S=axial OH; R=Ac (CH$_3$C=O); T=OH; Q=OH;

P=OH; and Z is selected from $C_1$-$C_5$ aliphatic, $C_1$-$C_{20}$ aryl, $C_1$-$C_{20}$ aliphatic ether, $C_1$-$C_{10}$ aliphatic thioether, $NH_2$, $C_1$-$C_5$ aliphatic amine, $C_1$-$C_5$ aryl amine, $C_1$-$C_{20}$ aliphatic ester, $C_6$-$C_{20}$ aryl ether, or a monosaccharide.

In some embodiments, U=O or $CH_2$; V=$CH_2$; W=NH; X=H or OH; S=axial OH; R=Ac ($CH_3C$=O); T=OH; Q=OH; Z=$OCH_3$; and P=OH.

In some embodiments, a monosaccharide includes glucose, mannose, galactose, GlcNAc, GalNAc, or ManNAc.

The present invention includes a glycomimetic compound having the formula of Type IV

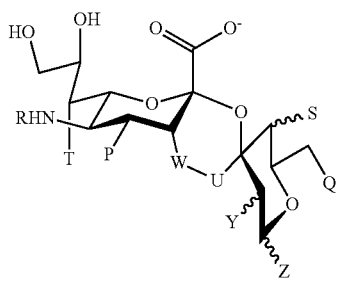

Type IV and pharmaceutically acceptable salts, esters, solvates, hydrates and multivalent versions thereof, wherein:

P is independently selected from the group consisting of a halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and a $C_6$-$C_{20}$ aryl ester;

Q is independently selected from the group consisting of a halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and a $C_6$-$C_{20}$ aryl ester;

R is independently selected from the group consisting of H, $C_1$-$C_5$ aliphatic ester, $C(O)CF_3$, triazole, and azide;

S is independently selected from the group consisting of an axial or equatorial halogen, OH, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and a $C_6$-$C_{20}$ aryl ester;

T is independently selected from the group consisting of a halogen, OH, H, $C_1$-$C_5$ aliphatic ether, $C_1$-$C_5$ aliphatic thioether, $NH_2$, $C_1$-$C_5$ aliphatic amine, $C_1$-$C_5$ aryl amine, $C_5$-$C_{10}$ aryl ether, $C_1$-$C_{20}$ aliphatic ester, and a $C_6$-$C_{20}$ aryl ester;

U is independently selected from the group consisting of $C_1$-$C_5$ aliphatic, O, NH, S, and a $C_1$-$C_5$ aliphatic amine;

W is independently selected from the group consisting of an axial or equatorial $C_1$-$C_5$ aliphatic, O, NH, S, and $C_1$-$C_5$ aliphatic amine;

Y is independently selected from the group consisting of an axial or equatorial halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_5$ aliphatic amide, $C_1$-$C_5$ aryl amine, $C_5$-$C_{10}$ arylether, $C_1$-$C_{20}$ aliphatic ester, and a $C_6$-$C_{20}$ aryl ester; and Z is independently selected from the group consisting of $C_1$-$C_5$ aliphatic, $C_1$-$C_{20}$ aryl, $C_1$-$C_{20}$ aliphatic ether, $C_1$-$C_{10}$ aliphatic thioether, $NH_2$, $C_1$-$C_5$ aliphatic amine, $C_1$-$C_5$ aryl amine, $C_1$-$C_{20}$ aliphatic ester, $C_6$-$C_{20}$ aryl ether, and a monosaccharide.

In some embodiments, P is selected from H, OH, halogen $C_1$-$C_5$ aliphatic ester, $C_1$-$C_5$ aliphatic ether, $C_5$-$C_{10}$ arylether, $C_1$-$C_{20}$ aliphatic ester, $C_6$-$C_{20}$ aryl ester, halogen, $OCH_3$, OBenzyl, or OCyclohexyl; U is O or $CH_2$; W=axial NH; Y=equatorial OH; Z=$OCH_3$; S=axial OH; R=Ac ($CH_3C$=O); T=OH; and Q=OH.

In some embodiments, U is selected from $C_1$-$C_5$ aliphatic, O, NH, S, or a $C_1$-$C_5$ aliphatic amine; W=axial NH; Y=equatorial OH; Z=$OCH_3$; S=axial OH; R=Ac ($CH_3C$=O); T=OH; Q=OH; and P=OH.

In some embodiments, U=O or $CH_2$; W is selected from an axial or equatorial $C_1$-$C_5$ aliphatic, O, NH, S, or a $C_1$-$C_5$ aliphatic amine; Y=equatorial OH; S=axial OH; R=Ac ($CH_3C$=O); T=OH; Q=OH; Z=$OCH_3$; and P=OH.

In some embodiments, U=O or $CH_2$; W=axial NH; Y is selected from an axial or equatorial halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_5$ aliphatic amide, $C_1$-$C_5$ aryl amine, $C_5$-$C_{10}$ arylether, $C_1$-$C_{20}$ aliphatic ester, or a $C_6$-$C_{20}$ aryl ester; and S=axial OH; R=Ac ($CH_3C$=O), T=OH; Q=OH; Z=$OCH_3$; and P=OH.

In some embodiments, U=O or $CH_2$; W=axial NH; Y=equatorial OH; S is selected from an axial or equatorial halogen, OH, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, or a $C_6$-$C_{20}$ aryl ester; R=Ac ($CH_3C$=O), T=OH; Q=OH; Z=$OCH_3$; and P=OH.

In some embodiments, U=O or $CH_2$; W=axial NH; Y=equatorial OH; S=axial OH; R is selected from H, $C_1$-$C_5$ aliphatic ester, $C(O)CF_3$, substituted triazole, or azide; T=OH; Q=OH; Z=$OCH_3$; and P=OH.

In some embodiments, U=O or $CH_2$; W=axial NH; Y=equatorial OH; S=axial OH; R=Ac ($CH_3C$=O; T is selected from a halogen, OH, H, $C_1$-$C_5$ aliphatic ether, $C_1$-$C_5$ aliphatic thioether, $NH_2$, $C_1$-$C_5$ aliphatic amine, $C_1$-$C_5$ aryl amine, $C_5$-$C_{10}$ aryl ether, $C_1$-$C_{20}$ aliphatic ester, or a $C_6$-$C_{20}$ aryl ester; Q=OH; Z=$OCH_3$; and P=OH.

In some embodiments, U=O or $CH_2$; W=axial NH; Y=equatorial OH; S=axial OH; R=Ac ($CH_3C$=O); T=OH; Q is selected from a halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, or a $C_6$-$C_{20}$ aryl ester; Z=$OCH_3$; and P=OH.

In some embodiments, U=O or $CH_2$; W=axial NH; Y=equatorial OH; S=axial OH; R=Ac ($CH_3C$=O); T=OH; Q=OH; P=OH; Z is selected from $C_1$-$C_5$ aliphatic, $C_1$-$C_{20}$ aryl, $C_1$-$C_{20}$ aliphatic ether, $C_1$-$C_{10}$ aliphatic thioether, $NH_2$, $C_1$-$C_5$ aliphatic amine, $C_1$-$C_5$ aryl amine, $C_1$-$C_{20}$ aliphatic ester, $C_6$-$C_{20}$ aryl ether, or a monosaccharide.

In some embodiments, U=O or $CH_2$; W=axial NH; Y=equatorial OH; S=axial OH; R=Ac ($CH_3C$=O); T=OH; Q=OH; Z=$OCH_3$; and P=OH.

In some embodiments, a monosaccharide includes glucose, mannose, galactose, GlcNAc, GalNAc, or ManNAc.

The present invention includes a glycomimetic compound having the formula of Type V

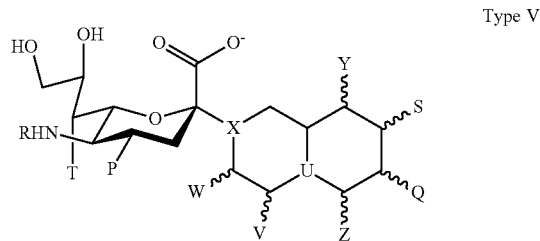

Type V and pharmaceutically acceptable salts, esters, solvates, hydrates and multivalent versions thereof, wherein:

P is independently selected from a halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and a $C_6$-$C_{20}$ aryl ester;

Q is independently selected from a halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and a $C_6$-$C_{20}$ aryl ester;

R is independently selected from H, $C_1$-$C_5$ aliphatic ester, $C(O)CF_3$, triazole, and azide;

S is independently selected from an axial or equatorial halogen, OH, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and a $C_6$-$C_{20}$ aryl ester;

T is independently selected from a halogen, OH, H, $C_1$-$C_5$ aliphatic ether, $C_1$-$C_5$ aliphatic thioether, $NH_2$, $C_1$-$C_5$ aliphatic amine, $C_1$-$C_5$ aryl amine, $C_5$-$C_{10}$ aryl ether, $C_1$-$C_{20}$ aliphatic ester, and a $C_6$-$C_{20}$ aryl ester;

U is independently selected from $C_1$-$C_5$ aliphatic, N, and S;

V is independently selected from $C_1$-$C_{20}$ aliphatic, $C_1$-$C_{20}$ aryl, halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and a $C_6$-$C_{20}$ aryl ester;

W is independently selected from $C_1$-$C_{20}$ aliphatic, $C_1$-$C_{20}$ aryl, halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and a $C_6$-$C_{20}$ aryl ester;

X is independently selected from COH, $C_1$-$C_5$ aliphatic, N, and S;

Y is independently selected from an axial or equatorial halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_5$ aliphatic amide, $C_1$-$C_5$ aryl amine, $C_5$-$C_{10}$ arylether, $C_1$-$C_{20}$ aliphatic ester, and a $C_6$-$C_{20}$ aryl ester; and Z is independently selected from $C_1$-$C_{20}$ aliphatic, $C_1$-$C_{20}$ aryl, $C_1$-$C_{20}$ aliphatic ether, $C_1$-$C_{10}$ aliphatic thioether, $C_1$-$C_5$ aliphatic amine, $C_1$-$C_5$ aryl amine, $C_1$-$C_{20}$ aliphatic ester, $C_6$-$C_{20}$ aryl ether, H, and a monosaccharide.

In some embodiments, P is selected from a halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and a $C_6$-$C_{20}$ aryl ester; U=N or CH; W=H; Y=axial OH; Z=$CH_2OMe$, S=equatorial OH; R=Ac ($CH_3C$=O); T=OH; Q=equatorial OH; V=H; and X=COH.

In some embodiments, U is selected from CH, $C_1$-$C_5$ aliphatic, N, and S; W=H; Y=axial OH; Z=$CH_2OMe$, S=equatorial OH; R=Ac ($CH_3C$=O); T=OH; Q=equatorial OH; V=H; X=COH; and P=equatorial OH.

In some embodiments, U=N or CH; W is selected from $C_1$-$C_{20}$ aliphatic, $C_1$-$C_{20}$ aryl, halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and a $C_6$-$C_{20}$ aryl ester; Y=axial OH; Z=$CH_2OMe$; S=equatorial OH; R=Ac ($CH_3C$=O); T=OH; Q=equatorial OH; V=H; X=COH; and P=equatorial OH.

In some embodiments, U=N or CH; W=H; Y is selected from an axial or equatorial halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_5$ aliphatic amide, $C_1$-$C_5$ aryl amine, $C_5$-$C_{10}$ arylether, $C_1$-$C_{20}$ aliphatic ester, and a $C_6$-$C_{20}$ aryl ester; Z=$CH_2OMe$, S=equatorial OH; R=Ac ($CH_3C$=O); T=OH; Q=equatorial OH; V=H; X=COH; and P=equatorial OH.

In some embodiments, U=N or CH; W=H; Y=axial OH; Z is selected from $C_1$-$C_{20}$ aliphatic, $C_1$-$C_{20}$ aryl, $C_1$-$C_{20}$ aliphatic ether, $C_1$-$C_{10}$ aliphatic thioether, $C_1$-$C_5$ aliphatic amine, $C_1$-$C_5$ aryl amine, $C_1$-$C_{20}$ aliphatic ester, $C_6$-$C_{20}$ aryl ether, H, and a monosaccharide; S=equatorial OH; R=Ac ($CH_3C$=O); T=OH; Q=equatorial OH; V=H; X=COH; and P=equatorial OH.

In some embodiments, U=N or CH; W=H; Y=axial OH; Z=$CH_2OMe$; S is selected from an axial or equatorial halogen, OH, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and a $C_6$-$C_{20}$ aryl ester; R=Ac ($CH_3C$=O); T=OH; Q=equatorial OH; V=H; X=COH; and P=equatorial OH.

In some embodiments, U=N or CH; W=H; Y=axial OH; Z=$CH_2OMe$; S=equatorial OH; R is selected from H, $C_1$-$C_5$ aliphatic ester, $C(O)CF_3$, triazole, and azide); T=OH; Q=equatorial OH; V=H; X=COH; and P=equatorial OH.

In some embodiments, U=N or CH; W=H; Y=axial OH; Z=$CH_2OMe$; S=equatorial OH; R=Ac ($CH_3C$=O); T is selected from a halogen, OH, H, $C_1$-$C_5$ aliphatic ether, $C_1$-$C_5$ aliphatic thioether, $NH_2$, $C_1$-$C_5$ aliphatic amine, $C_1$-$C_5$ aryl amine, $C_5$-$C_{10}$ aryl ether, $C_1$-$C_{20}$ aliphatic ester, and a $C_6$-$C_{20}$ aryl ester; Q=equatorial OH; V=H; X=COH; and P=equatorial OH.

In some embodiments, U=N or CH; W=H; Y=axial OH; Z=$CH_2OMe$; S=equatorial OH; R=Ac ($CH_3C$=O); T=OH; Q is selected from a halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and a $C_6$-$C_{20}$ aryl ester; V=H; X=COH; and P=equatorial OH.

In some embodiments, U=N or CH; W=H; Y=axial OH; Z=$CH_2OMe$; S=equatorial OH; R=Ac ($CH_3C$=O); T=OH; Q=equatorial OH; V is selected from $C_1$-$C_{20}$ aliphatic, $C_1$-$C_{20}$ aryl, halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and a $C_6$-$C_{20}$ aryl ester; X=COH; V=H; and P=equatorial OH.

In some embodiments, U=N or CH; W=H; Y=axial OH; Z=$CH_2OMe$; S=equatorial OH; R=Ac ($CH_3C$=O); T=OH; Q=equatorial OH; X is selected from COH, $C_1$-$C_5$ aliphatic, N, and S; V=H; and P=equatorial OH.

In some embodiments, U=N or CH; W=H; Y=axial OH; Z=$CH_2OMe$; S=equatorial OH; R=Ac ($CH_3C$=O); T=OH; Q=equatorial OH; V=H; X=COH; and P=equatorial OH.

In some embodiments, a monosaccharide includes glucose, mannose, galactose, GlcNAc, GalNAc, or ManNAc.

In some embodiments, a Type I, Type II, Type III, Type IV, or Type V glycomimetic of the present invention inhibits the binding of a pathogen to a cell surface sialylated galactose. In some embodiments, the cell surface sialylated galactose includes a terminal Neu5Ac-α-(2-3)-Gal. In some embodiments, the pathogen is BK virus, *H. pylori, S. pneumoniae, M. pneumoniae, E. coli, N. meningitides, T. gondii,* or influenza A.

The present invention also includes compositions including one or more glycomimetics as described herein. In some embodiments, a composition includes a pharmaceutically acceptable carrier. In some embodiments, a composition is formulated for oral, topical, mucosal, parenteral, or aerosol administration. In some embodiments, a composition is formulated for impregnating filters, masks, clothing, and/or an indwelling medical device.

The present invention includes a method of treating a disorder in which a sialylated glycan receptor is implicated, the method including administering a glycomimetic or composition as described herein. In some embodiments, the disorder is mediated by an infectious agent that binds to a sialylated galactose on a host cell surface. In some embodiments, the sialylated galactose includes a terminal Neu5Ac-α-(2-3)-Gal or a terminal Neu5Ac-α-(2-6)-Gal. In some embodiments, the disorder is mediated by BK virus, *H. pylori, S. pneumoniae, M. pneumoniae, E. coli, N. meningitides, T. gondii* or influenza A. In some embodiments, administration is oral, topical, mucosal, parenteral, or aerosol administration. In some embodiments, administration is by impregnated filters, masks, clothing, and/or indwelling medical device.

The present invention includes a method of preventing or reducing transmission and/or infection of an infectious agent, the method including administering a glycomimetic or composition as described herein. In some embodiments, the infectious agent binds to a sialylated galactose on a host cell surface. In some embodiments, the sialylated galactose includes a terminal Neu5Ac-α-(2-3)-Gal or a terminal Neu5Ac-α-(2-3)-Gal. In some embodiments, the disorder is mediated by BK virus, *H. pylori, S. pneumoniae, M. pneumoniae, E. coli, N. meningitides, T. gondii* or influenza A. In some embodiments, administration is oral, topical, mucosal, parenteral, or aerosol administration. In some embodiments, administration is by impregnated filters, masks, clothing, and/or indwelling medical device.

The present invention includes a method of impregnating an article, the method including contacting an article with a glycomimetic or composition as described herein.

The present invention includes a method of synthesizing a glycomimetic compound as described herein.

The present invention includes an article impregnated with a glycomimetic or composition as described herein. In some embodiments, the article is a filter, mask, an article of clothing, or an indwelling medical device.

The present invention includes a computer aided method for generating glycomimetics to inhibit pathogen-host interactions, the method including one or more of:

analysing the conformation of the natural glycan using computational simulations;

performing a computational simulations to predict the binding energies of native glycan-pathogen complex;

proposing alterations to the native glycan including, but not limited to, increasing the affinity of the glycomimetic for the receptor protein by pre-ordering the glycan in the bound conformation in order to reduce the entropic penalty upon binding, or by modifying the glycomimetic structure with additional chemical moieties to yield a glycomimetic scaffold or glycomimetic;

analysing the conformation of the glycomimetic compound or glycomimetic scaffold using computational simulations to allow comparison to the natural glycan;

performing a computational simulation to predict the binding energies of glycomimetic-pathogen complex or glycomimetic scaffold-pathogen complex;

performing computational substituent remodelling of the glycomimetic or glycomimetic scaffold to further improve the affinity of the molecule for the pathogen, or to modify certain properties of the molecule including, but not limited to, molecular mass, octanol-water partition coefficient, polarity, charge, number of hydrogen bond donors/acceptors, number of halogen bond donors/acceptors; and/or performing further computational simulations, including to MMPBSA analysis, MMGBSA analysis, Free Energy Perturbation (FEP) calculations, or Thermodynamic Integration (TI) to predict the binding energies of glycomimetic-pathogen complex.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

BRIEF DESCRIPTION OF THE FIGURES

FIG. 1A shows the structure of α-Neu5Ac-(2,3)-Gal. FIG. 1B shows the structure of Glycomimetic Target I. FIG. 1C shows the structure of Glycomimetic Target II.

FIG. 3A shows structure for optimization using BOMB. FIG. 3B shows structure for optimization with HA.

FIG. 11. Development of a hypothetical carbohydrate-based lead inhibitor.

FIGS. 12A to 12D. Structure of the influenza receptor glycan in complex with H1 domain (FIG. 12A) and in complex with the conformationally-restricted glycomimetic scaffold (FIG. 12B). Structure of the influenza receptor glycan in complex with H1 domain (FIG. 12C) and in complex with the conformationally-restricted glycomimetic scaffold (FIG. 12D).

DETAILED DESCRIPTION OF ILLUSTRATIVE EMBODIMENTS

Figure 1A:
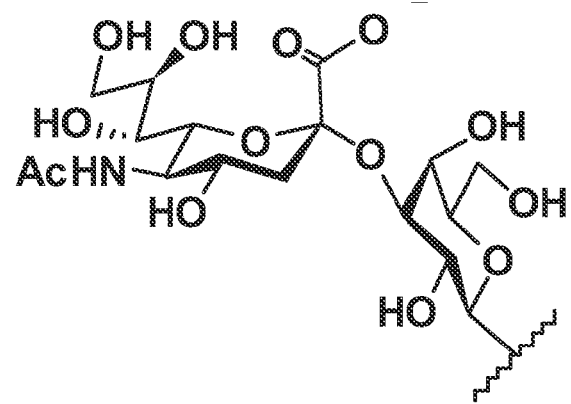
FIGS. 1A to 1C. Glycomimetic structures.

The first stage of infection for many pathogens is their adherence through specific interactions between surface proteins and glycans present on host cells. The present invention includes glycomimetics that block pathogen adhesion and/or infection. These glycomimetic compounds are rationally designed to inhibit the binding of a pathogen to a cell surface sialylated galactose. As used herein, the term "glycomimetic" refers to a molecule designed based on the natural glycan, but improved upon in one or more ways including, but not limited to, an increased binding affinity of the glycomimetic for the receptor protein, increased membrane permeability, increased serum halflife, and/or increased resistance to metabolic degradation Ernst. Glycomimetic compounds of the present invention are organic, non-peptidic topomimetic compounds that mimic a portion of the surface topography of, for example, a sialylated galactose such as, for example, ($\alpha$-Neu5Ac-(2,3)-Gal) or, ($\alpha$-Neu5Ac-(2,6)-Gal). Such glycomimetic compounds are useful for the blocking of pathogen adhesion to host cells or tissues and/or preventing infection of influenza A and other pathogens. A glycomimetic of the present invention mimics the natural influenza sialylated glycan receptors found on host cells, including (Neu5Ac-(2,3)-Gal (avian receptor) or Neu5Ac-(2,6)-Gal (human receptor)) and thus blocks virus particles from adhering to and infecting host tissue.

The outer membrane of the influenza virion is made up of a lipid bilayer that is densely studded with two viral membrane glycoproteins, hemagglutinin (HA) and neuraminidase (NA). HA is a protein that binds tightly to the sugar portions of various cell-surface glycoproteins by recognizing and binding the sugar sialic acid (Neu5Ac). Human influenza viruses preferentially bind to glycans containing terminal sialic acid residues linked to galactose though $\alpha$-(2,6) linkages (Wong et al., 2006, Chest; 129:156-168; and Webster et al., 1992, Microbiol Mol Biol Rev; 56:152-179) and avian influenza viruses bind to glycans containing terminal sialic acid residues linked to galactose though $\alpha$-(2,3) linkages. HA permits the influenza virus to attach to a host cell during the initial infection. The NA on the surface of the virion is necessary for new viral particles to break away from the host cell. NA is a glycosidase that promotes the cleavage of sialic acid from glycoprotein saccharide chains. When the glycosidic linkage is cleaved, the viral particle is no longer tethered to the host cell and can infect other cells.

Inhibitors of NA, such as zanamivir (Relenza) and oseltamivir carboxylate (Tamiflu) are currently used for the treatment of influenza infections, but the rapid evolution of the virus has produced resistant strains by point mutations in the viral NA (von Itzstein et al., 1993, Nature; 363:418-423; McKimm-Breschkin, 2000, Antiviral Res; 47:1-17; and Wang et al., 2002, Antimicrob Agents Chemother; 46:3809-3816). The potential for oligosaccharides containing terminal sialic acid to compete with natural glycans and thus function as anti-adhesives has been demonstrated (Ilona Idanpaan-Heikkila et al., 1997, J Infect Dis; 176:704-712). However, considerable work needs to be done to establish approaches for converting the exogenous oligosaccharides into high affinity inhibitors that can compete effectively at low to moderate concentrations against the native glycans.

In scaffold-based drug design, an anchoring moiety provides the specificity for the receptor, and the design process consists of appending various functional groups to a core scaffold in an attempt to fill the void space in the binding site and match electrostatic surface interactions. Substituent modifications of carbohydrate scaffolds have been shown to lead to promising affinity enhancement. The resulting compounds may be considered to be glycomimetics. The Sharon laboratory was the first to show that a glycomimetic could be used to ameliorate infection, however, the development of carbohydrate-based anti-adhesives has since made little headway (Sharon, 2006, Biochim Biophys Acta; 1760:527-37). In principle, computational methods are well suited to determining potential modifications of the basic scaffold (Jorgensen, 2004, Science; 303:1813-1818) but they have not yet been widely applied to the design of carbohydrate-based inhibitors. A significant challenge in using carbohydrates as therapeutic agents is the low affinity of most carbohydrate-protein interactions. However, several carbohydrate leads have been converted to glycomimetic drugs (Ernst and Magnani, 2009, Nature Rev Drug Disc; 8:661-677) and the NA inhibitors Relenza and Tamiflu demonstrate that with appropriate chemical derivatisation molecules based on carbohydrate scaffolds can be converted into anti-influenza agents. A more significant limitation has been the lack of accurate and convenient computational tools for use in guiding glycomimetic design. Also, the synthetic chemistry associated with carbohydrates is highly specialized, and not amenable to the creation of large combinatorial libraries of the type required by high-throughput screening. Thus, without a rational design strategy, the development of carbohydrate-based anti-adhesives has made little headway (Sharon, 2006, Biochim Biophys Acta; 1760:527-37) and thus, the need for the rational design protocol of the present invention.

Many pathogens employ the same glycans as influenza A (sialylated galactose) as their adhesion partner (Ernst and Magnani, 2009, *Nature Rev Drug Disc;* 8:661-677; Blumenschein et al., 2007, *EMBO J;* 26:2808-2820; Dugan et al., 2005, *J Virol;* 79:14442-14445; and Simon, 1996, *Drug Disc Today;* 1:522-528), including BK virus, *H. pylori, S. pneumoniae, M. pneumoniae, E. coli, N. meningitides,* and *T. gondii.* Thus, in addition to blocking influenza A adhesion and/or infection, a glycomimetic of the present invention may also be effective against a broad range of unrelated pathogens.

Figure 14A:
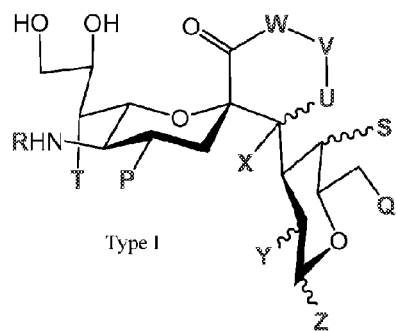
FIGS. 14A to 14E. Structures of glycomimetic compounds Type I, Type II, Type, III, Type IV, and Type V.
Figure 14B:
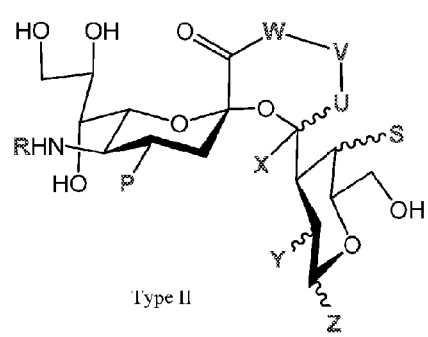
Figure 14C:
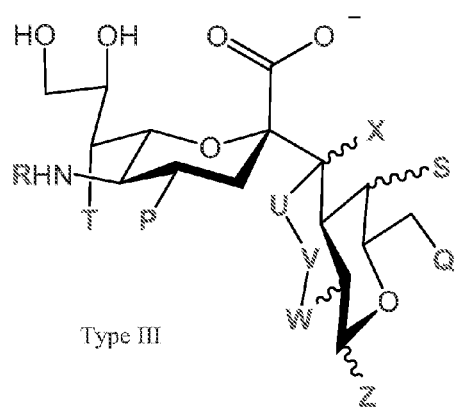
Figure 14D:
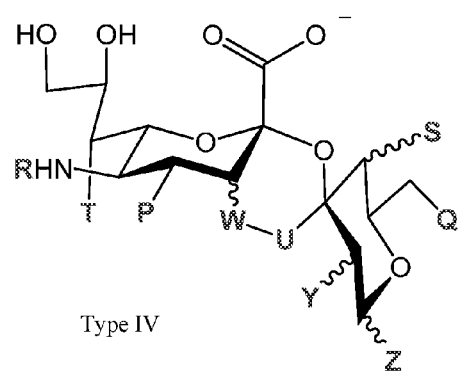
Figure 14E:
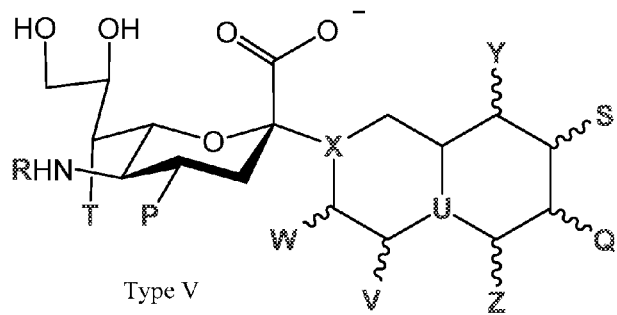

A glycomimetic compound of the present invention includes a glycomimetic compound having a formula of Type I (see also FIG. 14A), Type II (see also FIG. 14B), Type III (see also FIG. 14C), Type IV (see also FIG. 14D), and Type V (FIG. 14E), as shown below, and pharmaceutically acceptable salts, esters, intermediate, solvates, hydrates and multivalent versions thereof.

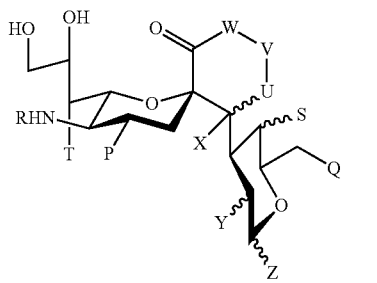

Type I

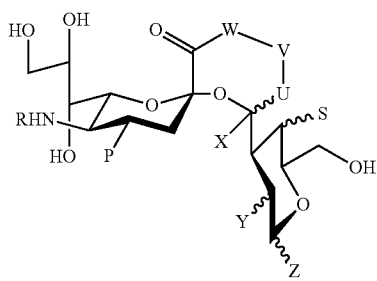

Type II

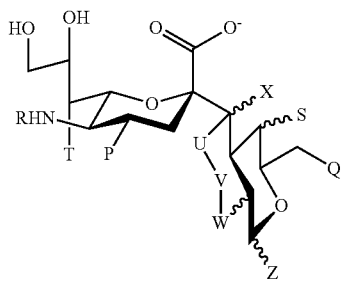

Type III

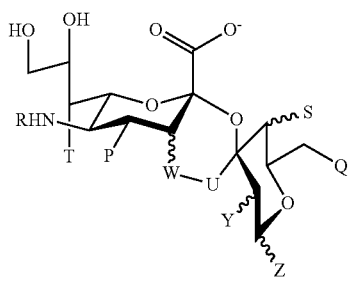

Type IV

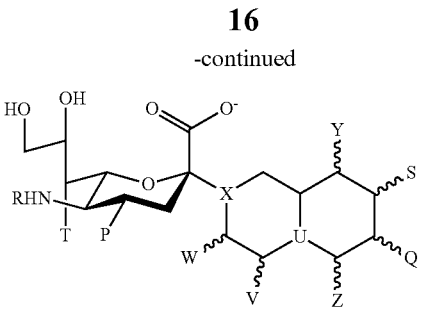

Type V

In various embodiments of compounds of Type I, Type II, Type III, or Type IV:

P may be independently selected from a halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, or $C_6$-$C_{20}$ aryl ester;

Q may be independently selected a halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, or $C_6$-$C_{20}$ aryl ester;

R may be independently selected from H, $C_1$-$C_5$ aliphatic ester, $C(O)CF_3$, triazole, azide;

S may be independently selected an axial or equatorial halogen, OH, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, or $C_6$-$C_{20}$ aryl ester;

T may be independently selected from a halogen, OH, H, $C_1$-$C_5$ aliphatic ether, $C_1$-$C_5$ aliphatic thioether, $NH_2$, $C_1$-$C_5$ aliphatic amine, $C_1$-$C_5$ aryl amine, $C_5$-$C_{10}$ aryl ether, $C_1$-$C_{20}$ aliphatic ester, or $C_6$-$C_{20}$ aryl ester;

U may be independently selected from $C_1$-$C_5$ aliphatic, O, NH, S, or $C_1$-$C_5$ aliphatic amine;

V may be independently selected from $C_1$-$C_5$ aliphatic;

W may be independently selected from $C_1$-$C_5$ aliphatic, O, NH, S, or $C_1$-$C_5$ aliphatic amine;

X may be independently selected from H, OH, halogen $C_1$-$C_5$ aliphatic ester, $C_1$-$C_5$ aliphatic ether, $C_5$-$C_{10}$ arylether, $C_1$-$C_{20}$ aliphatic ester, or $C_6$-$C_{20}$ aryl ester;

Y may be independently selected an axial or equatorial halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_5$ aliphatic amide, $C_1$-$C_5$ aryl amine, $C_5$-$C_{10}$ arylether, $C_1$-$C_{20}$ aliphatic ester, or $C_6$-$C_{20}$ aryl ester; and Z may be independently selected from $C_1$-$C_5$ aliphatic, $C_1$-$C_{20}$ aryl, $C_1$-$C_{20}$ aliphatic ether, $C_1$-$C_{10}$ aliphatic thioether, $NH_2$, $C_1$-$C_5$ aliphatic amine, $C_1$-$C_5$ aryl amine, $C_1$-$C_{20}$ aliphatic ester, $C_6$-$C_{20}$ aryl ether, or monosaccharide (where a monosaccharide may be, for example, glucose, mannose, galactose, GlcNAc, GalNAc, or ManNAc).

In various embodiments of compounds of Type V:

P may be independently selected from a halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and a $C_6$-$C_{20}$ aryl ester;

Q may be independently selected from a halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and a $C_6$-$C_{20}$ aryl ester;

R may be independently selected from H, $C_1$-$C_5$ aliphatic ester, $C(O)CF_3$, triazole, and azide;

S may be independently selected from an axial or equatorial halogen, OH, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and a $C_6$-$C_{20}$ aryl ester;

T may be a halogen, OH, H, $C_1$-$C_5$ aliphatic ether, $C_1$-$C_5$ aliphatic thioether, $NH_2$, $C_1$-$C_5$ aliphatic amine, $C_1$-$C_5$ aryl amine, $C_5$-$C_{10}$ aryl ether, $C_1$-$C_{20}$ aliphatic ester, and a $C_6$-$C_{20}$ aryl ester;

U may be independently selected from $C_1$-$C_5$ aliphatic, N, and S;

V may be selected from $C_1$-$C_{20}$ aliphatic, $C_1$-$C_{20}$ aryl, halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and a $C_6$-$C_{20}$ aryl ester;

W may be selected from $C_1$-$C_{20}$ aliphatic, $C_1$-$C_{20}$ aryl, halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and a $C_6$-$C_{20}$ aryl ester;

X may be selected from COH, $C_1$-$C_5$ aliphatic, N, and S;

Y may be independently selected from an axial or equatorial halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_5$ aliphatic amide, $C_1$-$C_5$ aryl amine, $C_5$-$C_{10}$ arylether, $C_1$-$C_{20}$ aliphatic ester, and a $C_6$-$C_{20}$ aryl ester; and Z may be independently selected from $C_1$-$C_{20}$ aliphatic, $C_1$-$C_{20}$ aryl, $C_1$-$C_{20}$ aliphatic ether, $C_1$-$C_{10}$ aliphatic thioether, $C_1$-$C_5$ aliphatic amine, $C_1$-$C_5$ aryl amine, $C_1$-$C_{20}$ aliphatic ester, $C_6$-$C_{20}$ aryl ether, H, and a monosaccharide.

In some embodiments of a glycomimetic of Type I, Type II, Type III, Type IV, or Type V, P may be H, OH, halogen $C_1$-$C_5$ aliphatic ester, $C_1$-$C_5$ aliphatic ether, $C_5$-$C_{10}$ arylether, $C_1$-$C_{20}$ aliphatic ester, $C_6$-$C_{20}$ aryl ester, halogen, $OCH_3$, OBenzyl, OCyclohexyl; U is O or $CH_2$; V=CH2; W=NH; X=H; Y=equatorial OH; Z=OCH3, S=axial OH; R=Ac ($CH_3C$=O); T=OH; and Q=OH.

In some embodiments of a glycomimetic of Type I, Type II, Type III, Type IV, or Type V, U may be a $C_1$-$C_5$ aliphatic, O, NH, S, and $C_1$-$C_5$ aliphatic amine; V=$CH_2$; W=NH; X=H; Y=equatorial OH; Z=$OCH_3$, S=axial OH; R=Ac ($CH_3C$=O); T=OH; Q=OH; and P=OH.

In some embodiments of a glycomimetic of Type I, Type II, Type III, Type IV, or Type V, U is O or $CH_2$; V may be a $C_1$-$C_5$ aliphatic; W=NH; X=H or OH; Y=equatorial OH; S=axial OH; R=Ac ($CH_3C$=O); T=OH; Q=OH; P=OH; and Z=$OCH_3$.

In some embodiments of a glycomimetic of Type I, Type II, Type III, Type IV, or Type V, U=O or $CH_2$; V=$CH_2$; W may be a $C_1$-$C_5$ aliphatic, O, NH, S, and $C_1$-$C_5$ aliphatic amine; X=H or OH; Y=equatorial OH; S=axial OH; R=Ac ($CH_3C$=O); T=OH; Q=OH; Z=$OCH_3$; and P=OH.

In some embodiments of a glycomimetic of Type I, Type II, Type III, Type IV, or Type V, U=O or $CH_2$; V=$CH_2$; W=NH; X may be H, OH, halogen $C_1$-$C_5$ aliphatic ester, $C_1$-$C_5$ aliphatic ether, $C_5$-$C_{10}$ arylether, $C_1$-$C_{20}$ aliphatic ester, $C_6$-$C_{20}$ aryl ester, halogen, $OCH_3$, OBenzyl, OCyclohexyl; Y=equatorial OH; S=axial OH; R=Ac ($CH_3C$=O); T=OH; Q=OH; Z=$OCH_3$; and P=OH.

In some embodiments of a glycomimetic of Type I, Type II, Type III, Type IV, or Type V, U=O or $CH_2$; V=$CH_2$; W=NH; X=H or OH; Y may be an axial or equatorial halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_5$ aliphatic amide, $C_1$-$C_5$ aryl amine, $C_5$-$C_{10}$ arylether, $C_1$-$C_{20}$ aliphatic ester, $C_6$-$C_{20}$ aryl ester; S=axial OH; R=Ac ($CH_3C$=O), T=OH; Q=OH; Z=$OCH_3$; and P=OH.

In some embodiments of a glycomimetic of Type I, Type II, Type III, Type IV, or Type V, U=O or $CH_2$; V=$CH_2$; W=NH; X=H or OH; Y=equatorial OH; may be an axial or equatorial halogen, OH, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, or $C_6$-$C_{20}$ aryl ester; R=Ac ($CH_3C$=O); T=OH; Q=OH; Z=$OCH_3$; and P=OH.

In some embodiments of a glycomimetic of Type I, Type II, Type III, Type IV, or Type V, U=O or $CH_2$; V=$CH_2$; W=NH; X=H or OH; Y=equatorial OH; S=axial OH; R may be H, $C_1$-$C_5$ aliphatic ester, $C(O)CF_3$, substituted triazole, or azide; T=OH; Q=OH; Z=$OCH_3$; and P=OH.

In some embodiments of a glycomimetic of Type I, Type II, Type III, Type IV, or Type V, U=O or $CH_2$; V=$CH_2$; W=NH; X=H; Y=equatorial OH; S=axial OH; R=Ac ($CH_3C$=O), T may be a halogen, OH, H, $C_1$-$C_5$ aliphatic ether, $C_1$-$C_5$ aliphatic thioether, $NH_2$, $C_1$-$C_5$ aliphatic amine, $C_1$-$C_5$ aryl amine, $C_5$-$C_{10}$ aryl ether, $C_1$-$C_{20}$ aliphatic ester, or $C_6$-$C_{20}$ aryl ester; Q=OH; Z=$OCH_3$; and P=OH.

In some embodiments of a glycomimetic of Type I, Type II, Type III, Type IV, or Type V, U=O or $CH_2$; V=$CH_2$; W=NH; X=H; Y=equatorial OH; S=axial OH; R=Ac ($CH_3C$=O); T=OH; Q may be a halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, or $C_6$-$C_{20}$ aryl ester; Z=$OCH_3$; and P=OH.

In some embodiments of a glycomimetic of Type I, Type II, Type III, Type IV, or Type V, U=O or $CH_2$; V=$CH_2$; W=NH; X=H; Y=equatorial OH; S=axial OH; R=Ac ($CH_3C$=O); T=OH; Q=OH; P=OH; and Z may be a $C_1$-$C_5$ aliphatic, $C_1$-$C_{20}$ aryl, $C_1$-$C_{20}$ aliphatic ether, $C_1$-$C_{10}$ aliphatic thioether, $NH_2$, $C_1$-$C_5$ aliphatic amine, $C_1$-$C_5$ aryl amine, $C_1$-$C_{20}$ aliphatic ester, $C_6$-$C_{20}$ aryl ether, or monosaccharide (where a monosaccharide may be, for example, glucose, mannose, galactose, GlcNAc, GalNAc, ManNAc.

In some embodiments of a glycomimetic of Type I, Type II, Type III, Type IV, or Type V, U=O or $CH_2$; V=$CH_2$; W=NH; X=H or OH; Y=equatorial OH; S=axial OH; R=Ac ($CH_3C$=O); T=OH; Q=OH; Z=$OCH_3$; and P=OH.

A glycomimetic compound of the present invention, may also be referred to herein as, for example, a glycomimetic, a glycomimetic agent, a topomimetic, a topomimetic compound, a topomimetic agent, a non-peptidic topomimetic, a non-peptidic topomimetic compound, a non-peptidic topomimetic agent, an anti-adhesion compound, an anti-adhesive compound, a glycomimetic anti-adhesion compound, a glycomimetic anti-adhesive compound, an anti-adhesion agent, an anti-adhesive agent, a glycomimetic anti-adhesion agent, a glycomimetic anti-adhesive agent, an anti-adhesive, a therapeutic compound, a therapeutic agent, a compound, or an agent.

A compound of the present invention also includes precursors, intermediates and derivatives (including, for example, synthetic derivatives) of a glycomimetic compound of Type I, Type II, Type III, Type IV, or Type V, as described herein, and pharmaceutically acceptable salts of the compounds, precursors, intermediates and derivatives. The compounds of the present invention may be isolated in the form of esters, salts, hydrates or solvates—all of which are embraced by the present invention. Where suitable, it will be appreciated that all optional and/or preferred features of one embodiment of the invention may be combined with optional and/or preferred features of another/other embodiment(s) of the invention.

It should be understood that a glycomimetic compound as described herein includes any or all of such forms, whether explicitly stated or not (although at times, "salts" are explicitly stated). The present disclosure also includes pharmaceutically acceptable salts of the compounds described herein. As used herein, "pharmaceutically acceptable salts"

refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. The pharmaceutically acceptable salts can be synthesized from the parent compound which contains a basic or acidic moiety by conventional chemical methods. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like. Certain specific compounds of the present invention contain both basic and acidic functionalities that allow the compounds to be converted into either base or acid addition salts.

In addition to salt forms, the present invention provides compounds which are in a prodrug form. Prodrugs of the compounds or complexes described herein readily undergo chemical changes under physiological conditions to provide the compounds of the present invention. The term, "prodrug", as defined herein, is a biologically inactive derivative of a parent drug molecule that exerts its pharmacological effect only after chemical and/or enzymatic conversion to its active form in vivo. Prodrugs include those designed to circumvent problems associated with delivery of the parent drug. This may be due to poor physicochemical properties, such as poor chemical stability or low aqueous solubility, and may also be due to poor pharmacokinetic properties, such as poor bioavailability or poor half-life. Thus, certain advantages of prodrugs may include improved chemical stability, absorption, and/or PK properties of the parent carboxylic acids. Prodrugs may also be used to make drugs more "patient friendly," by minimizing the frequency (e.g., once daily) or route of dosing (e.g., oral), or to improve the taste or odor if given orally, or to minimize pain if given parenterally. Additionally, prodrugs can be converted to the compounds of the present invention by chemical or biochemical methods in an ex vivo environment.

Compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

Compounds of the present invention may possess asymmetric carbon atoms (optical centers) or double bonds; the racemates, diastereomers, geometric isomers and individual isomers are encompassed within the scope of the present invention. The graphic representations of racemic, ambiscalemic and scalemic or enantiomerically pure compounds used herein follow those described by Maehr, 1985, *J Chem Ed;* 62:114-120.

Compounds of the invention can exist in particular geometric or stereoisomeric forms. The invention contemplates all such compounds, including cis- and trans-isomers, (−)- and (+)-enantiomers, (R)- and (S)-enantiomers, diastereomers, (D)-isomers, (L)-isomers, the racemic mixtures thereof, and other mixtures thereof, such as enantiomerically or diastereomerically enriched mixtures, as falling within the scope of the invention. Additional asymmetric carbon atoms can be present in a substituent such as an alkyl group. All such isomers, as well as mixtures thereof, are intended to be included in this invention.

The compounds of the present invention may also contain unnatural proportions of atomic isotopes at one or more of the atoms that constitute such compounds. For example, the compounds may be radiolabeled with radioactive isotopes, such as for example tritium, iodine-125, or carbon-14. All isotopic variations of the compounds of the present invention, whether radioactive or not, are intended to be encompassed within the scope of the present invention.

As used herein, the terms "alkyl", and the prefix "alk-" are inclusive of both straight chain and branched chain groups and of cyclic groups, e.g., cycloalkyl. Preferably, these groups contain from 1 to 20 carbon atoms. In some embodiments, these groups have a total of up to 10 carbon atoms, up to 8 carbon atoms, up to 6 carbon atoms, or up to 4 carbon atoms. Alkyls may be fully saturated, mono- or polyunsaturated and can include di- and multivalent radicals. Examples of saturated hydrocarbon radicals include, but are not limited to, groups such as methyl, ethyl, n-propyl, isopropyl, n-butyl, t-butyl, isobutyl, sec-butyl, cyclohexyl, (cyclohexyl)methyl, cyclopropylmethyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1, 4-pentadienyl), ethynyl, 1- and 3-propynyl, 3-butynyl, and the higher homologs and isomers. The term "unsubstituted alkyl" encompasses straight or branched chain saturated hydrocarbon radicals. Examples of saturated hydrocarbon radicals include, but are not limited to, groups such as methyl, ethyl, n-propyl, isopropyl, n-butyl, t-butyl, isobutyl, sec-butyl, n-pentyl. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2 to 12 carbon atoms, 1 to 3 rings, 1 to 4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The terms ester, amide, amine, hydroxyl, halide, sulfonate, phosphonate, and guanidine refer to various different optional functional groups that may be included on groups attached to the topomimetic substrates of the invention. The functional groups are further described by the following chemical formulas: ester=—(CO)—O—; amide=—(CO)—NH—; amine=—NH$_2$, hydroxyl=—OH; halogen is an element selected from the group consisting of F, Cl, Br, and I; sulfonate=—O—SO$_3^-$; phosphonate=—P(O)(OH)$_2$; and guanidine=—NH—C(=NH)—NH$_2$. An example of a group used in an embodiment of the invention that includes a halogen functional group is a trifluoromethyl group.

As used herein, the terms "alkoxy" and "thioalkoxy" refer to groups wherein two hydrocarbon alkyl groups are bonded to an oxygen or a sulfur atom, respectively. For example, a group represented by the formula —O—R is an alkoxy group, whereas a group represented by the formula —S—R is a thioalkoxy group. For example, a cycloalkylalkoxy group is an alkoxy group attached to a cycloalkyl group, whereas an aralkyloxy group is an alkoxy group attached to an aralkyl group, as defined herein. The R within an alkoxy or thioalkoxy group, described above, may be any aryl or alkyl group, as described herein.

The terms "halo" or "halogen," by themselves or as part of another substituent, mean, unless otherwise stated, a fluorine, chlorine, bromine, or iodine atom. Additionally, terms such as "haloalkyl," are meant to include monohaloalkyl and polyhaloalkyl.

When a group is present more than once in any formula described herein, each group is independently selected, whether explicitly stated or not.

The present invention includes computer aided methods for generating glycomimetics to inhibit pathogen-host interactions, and the glycimimetics generated. Such a method may include one or more of the following steps:

analysing the conformation of the natural glycan using computational simulations;

performing a computational simulations to predict the binding energies of native glycan-pathogen complex;

proposing alterations to the native glycan including, but not limited to, increasing the affinity of the glycomimetic for the receptor protein by pre-ordering the glycan in the bound conformation in order to reduce the entropic penalty upon binding, or by modifying the glycomimetic structure with additional chemical moieties to yield a glycomimetic scaffold or glycomimetic. Additional improvements might include increasing membrane permeability, and or increasing serum halflife, and or increasing resistance to metabolic degradation;

analysing the conformation of the glycomimetic compound or glycomimetic scaffold using computational simulations to allow comparison to the natural glycan;

performing computational simulations to predict the binding energies of glycomimetic-pathogen complex or glycomimetic scaffold-pathogen complex;

performing computational substituent remodelling of the glycomimetic or glycomimetic scaffold to further improve the affinity of the molecule for the pathogen, or to modify certain properties of the molecule including, but not limited to, molecular mass, octanol-water partition coefficient, polarity, charge, number of hydrogen bond donors/acceptors, number of halogen bond donors/acceptors; and/or performing further computational simulations, including but not limited to, MM-PBSA analysis, MM-GBSA analysis, Free Energy Perturbation (FEP) calculations, or Thermodynamic Integration (TI) to predict the binding energies of glycomimetic-pathogen complex.

Computational simulations may include, but are not limited to, minimization, Monte Carlo methods, molecular dynamics and molecular docking. The steps, which are described in greater detail herein, can be modified as explained herein to arrive at the glycomimetic of the present invention.

There are a number of well-known methods for characterizing the conformation of the glycomimetic or native glycan both free in solution and in complex with a protein. One such technique involves using molecular dynamics (MD) simulations. Typical simulations can be performed under constant pressure and temperature (NPT) conditions or under constant volume and temperature (NVT) conditions. These simulations can be performed with the PMEMD module of AMBER (D. A. Case, T. A. D., T. E. Cheatham, III, C. L. Simmerling, J. Wang, R. E. Duke, R. Luo, R. C. Walker, W. Zhang, K. M. Merz, B. Roberts, B. Wang, S. Hayik, A. Roitberg, G. Seabra, I. Kolossvai, K. F. Wong, F. Paesani, J. Vanicek, J. Liu, X. Wu, S. R. Brozell, T. Steinbrecher, H. Gohlke, Q. Cai, X. Ye, J. Wang, M.-J. Hsieh, G. Cui, D. R. Roe, D. H. Mathews, M. G. Seetin, C. Sagui, V. Babin, T. Luchko, S. Gusarov, A. Kovalenko, and P. A. Kollman AMBER11, University of California, San Francisco, 2010) and the TIP3P water model. In certain embodiments, protein force field parameters are taken from the Parm99 set, carbohydrate parameters from GLYCAM06, and glycomimetic parameters may be taken from General AMBER force field (GAFF). Simulations may be performed with implicit solvent models under non-periodic boundary conditions.

AMBER is a molecular modelling and simulation package that provides simulation-based methods for structure-based ligand design and understanding of structure and free energy in any complex molecular system. AMBER was developed at and is available from University of California, San Francisco. Other modules within AMBER can be employed to perform these MD simulations. Indeed, programs other than AMBER exist for performing MD simulations including, but not limited to BOSS, CHARMM, GROMACS and MOE. Such programs are also applicable to the present invention.

In some aspects, initial coordinates for the glycan-protein complexes or glycomimetic-protein complexes can be selected from crystallographic data, if available. A theoretical model for the protein can also be employed, such as a model generated by homology or comparative modelling. When only a structure of the free enzyme is available, a co-complex can be predicted using AutoDock or another comparable program. AutoDock is a suite of automated docking tools designed to predict how small molecules bind to a receptor of known 3D structure. Other docking programs exist (e.g. DOCK, FlexiDock, GLIDE, GOLD, DOCK, MOE) and would be applicable to the present invention.

In certain embodiments, histidine protonation states can be inferred from intramolecular hydrogen bonds where possible, otherwise the histidine can be treated as neutral, protonated at NE. Any net charge on the complex can be neutralized by the addition of the appropriate number of counter ions (Cl− or Na+). Typically, the oligosaccharide-protein complexes will be solvated by, for example, ~10,000 TIP3P water molecules, in a periodic cube with a minimum distance between the edge of the box and the closest atom of the solute of 10 Å. Periodic boundary conditions can be applied together with Ewald treatment of long-range electrostatics with a direct space cutoff distance of 12 Å. It is understood that these parameters are not limiting of the invention. Indeed, it is understood that TIP3P is but just one of the classical water models that may be used for computational chemistry. Other water models, such as TIP4P, TIP5P, SPC, BNS, and others, can be used in the present invention. The water can also be approximated using implicit solvation models such as a dielectric constant, a distance-dependent dielectric constant, a generalized Born model, or by the Poisson-Boltzmann approximation.

In some aspects, ligand parameters and charges can be determined using Antechamber in AMBER 11 with the General AMBER force field (GAFF). The ligand is solvated TIP3P and neutralized using counter ions. The initial configurations can be energy minimized with the SANDER module. In one aspect, the initial configurations comprise 5,000 cycles of steepest descent and 25,000 cycles of conjugate gradient energy minimization with the SANDER module. Prior to the production dynamics stage, the entire system can be thermally equilibrated by heating again to 300K in 150 ps. Bonds containing hydrogen can be constrained to their equilibrium lengths using the SHAKE algorithm. The trajectory can then be processed using a trajectory processing program such as ptraj. From this characteristics including, but not limited to, bond angles, bond lengths and dihedral angles can be monitored.

In other aspects, the total free energy of binding (ΔG) may be calculated by direct decomposition of the interaction energies between the substrate and the protein (the reactants). Direct ΔG calculations combine molecular mechanics (MM) energy estimates with continuum solvent models, such as Poisson Boltzmann (PB) or generalized Born (GB) that attempt to capture the desolvation free energy. These calculations generally require the additional contributions from conformational entropy to be separately computed.

By way of example, and not by way of limitation, in a typical MM-GB/PB calculation the free energy is computed for the protein ($\Delta G_{protein}$), ligand ($\Delta G_{ligand}$), and complex ($\Delta G_{complex}$) for each structural "snapshot" extracted from the MD trajectories.

The initial portion of the data may be discarded to allow the system to equilibrate. For example, in a 10 ns trajectory, the first 1 ns can be discarded. In these models, snapshots of data can be collected at set intervals. By way of illustration only, 500 snapshots can selected from the remaining 9 ns for molecular mechanical (MM) binding energy analysis. The binding free energy (ΔG) can then be computed by subtraction (see Equation 1). Averaging over the entire trajectory results in the final average interaction energies ($\Delta G_{bind}$).

$$\Delta G_{bind} = \Delta G_{complex} - \Delta G_{protein} - \Delta G_{ligand} \quad \text{[Equation 1]}$$

where the averaging is over the MD snapshots.

The free energy of each reactant is calculated by summing four terms (see Equation 2):

$$\Delta G = \langle \Delta E_{MM} \rangle + \langle \Delta G_{Solv} \rangle + \langle \Delta G_{np} \rangle - T \langle \Delta S_{MM} \rangle \quad \text{[Equation 2]}$$

Where:

$\Delta Gs_{olv}$=Polar solvation energy of molecule (estimated using Poisson-Boltzman);

$\Delta G_{np}$=Non-polar solvation energy (estimated using the solvent accessible surface area of the molecule);

T=Temperature;

$\Delta S_{MM}$=Entropy of the molecule; and $\Delta E_{MM}$=Molecular mechanics energy of the molecule, i.e. sum of the internal energy of the molecule, electrostatics and van der Waals interaction (see Equation 3):

$$\Delta E_{MM} = E_{int} + E_{es} + E_{vdW} \quad \text{[Equation 3]}.$$

Prior to the analyses, the water molecules can be removed from the solvated trajectories. The energy contribution from solvation can then be obtained through application of the Poisson-Boltzmann (PB) implicit solvent model or the generalized Born (GB) implicit solvation model. The MM-GBSA results compare well with those from the more rigorous MM-PBSA analysis.

In some embodiments, vibrational, translational, and rotational contributions to the entropy can be derived from a normal mode analysis of the energy-minimized coordinates, while the conformational entropy is estimated from an analysis of the covariance matrix of the relevant internal coordinates (Karplus and Kushick, 1981, *Macromolecules;* 14(2):325-332). Changes in conformational entropy, arising primarily from hindered rotations, can be estimated from the motions of the backbone torsion angles in the free and bound forms of each ligand. From the determinants of the covariance matrices for the torsion angles in the bound and free states the relative conformational entropies can be derived.

This describes just one method for calculating ΔG. In another embodiment the glycomimetic may be subjected to MMPBSA analysis, MMGBSA analysis, Free Energy Perturbation (FEP) calculations, or Thermodynamic Integration (TI) to predict the total free energy of binding (ΔG).

Ligand stability in the binding site can be assessed by evaluating intermolecular hydrogen bonds between the glycan and the receptor protein. Average values for the hydrogen bonds and their percentage occupancies can be collected, and if possible they are collected along with crystallographically determined values.

Biochemical and Organic Molecule Builder (BOMB) (see Jorgensen, 2004, BOMB, Yale University: New Haven, Conn.) or similar algorithms used for de novo design of therapeutics may be employed to construct individual structures, or combinatorial libraries of structures given a glycomimetic scaffold. These calculations employ a library of ca.600 chemical moieties, each of which may be assessed for suitability as a substituent on the glycomimetic scaffold at a user specified position inside a binding site. A conformational search can be performed on each ligand produced, utilizing rotamer information stored for each substituent. The OPLS-AA force field for the protein and OPLS/CM1A for the analogue are applied to optimize the position and orientation of the analogue in the protein binding site. A docking-like scoring function (based on known SAR data) is then applied to the lowest energy conformer for each analogue to predict its efficacy.

In some embodiments the substituted analogues may be subjected to computational molecular docking using AutoDock or another equivalent program. AutoDock is a suite of automated docking tools designed to predict how small molecules bind to a receptor of known 3D structure. Other docking programs exist (e.g. DOCK, FlexiDock, GLIDE, GOLD, DOCK, MOE) and would also be applicable to the present invention.

In other embodiments the glycomimetic may be subjected to MMPBSA analysis, MMGBSA analysis, Free Energy Perturbation (FEP) calculations, or Thermodynamic Integration (TI) to predict the total free energy of binding ($\Delta G$).

As used herein, the term "$\Delta G$" refers to the Gibbs free energy of binding. The Gibbs free energy is a thermodynamic potential that represents the work which must be done in acting against the forces which hold a complex together, while disassembling the complex into component parts separated by sufficient distance that further separation requires negligible additional work. The expression "$\Delta E_{MM}$" refers to molecular mechanics free energy in gas-phase.

As used herein, the term "Molecular Dynamics" (MD) refers to a form of computer simulation in which atoms and molecules are allowed to interact for a period of time by approximations of known physics, giving a view of the motion of the particles. Classical MD simulations are governed by Newton's equations of motion employing energies and forces derived from a classical force field. A classical force field is a mathematic model that relates the atomic positions in a molecule or aggregate.

As used herein, the term "MM-PBSA" refers to a method of calculating the Gibbs free energy of binding as follows. The binding free energy ($\Delta G$) can be computed by subtraction (see Equation 1):

$$\Delta G_{bind} = \Delta G_{complex} - \Delta G_{protein} - \Delta G_{ligand} \quad \text{[Equation 1]}$$

The free energy of each reactant is calculated by summing four terms (see Equation 2):

$$\Delta G = <\Delta E_{MM}> + <\Delta G_{Solv}> + <\Delta G_{np}> - T<\Delta S_{MM}> \quad \text{[Equation 2]}$$

Where:
$\Delta Gs_{olv}$=Polar solvation energy of molecule (estimated using Poisson-Boltzman model);
$\Delta G_{np}$=Non-polar solvation energy (estimated using the solvent accessible surface area of the molecule);
T=Temperature;
$\Delta S_{MM}$=Entropy of the molecule; and
$\Delta E_{MM}$=Molecular mechanics energy of the molecule, i.e. sum of the internal energy of the molecule, electrostatics and van der Waals interaction (see Equation 3):

$$\Delta E_{MM} = E_{int} + E_{es} + E_{vdW} \quad \text{[Equation 3]}.$$

The term "MM-GBSA" refers to a method of calculating the Gibbs free energy of binding as follows. The binding free energy ($\Delta G$) can be computed by subtraction (see Equation 1):

$$\Delta G_{bind} = \Delta G_{complex} - \Delta G_{protein} - \Delta G_{ligand} \quad \text{[Equation 1]}$$

The free energy of each reactant is calculated by summing four terms (see Equation 2):

$$\Delta G = <\Delta E_{MM}> + <\Delta G_{Solv}> + <\Delta G_{np}> - T<\Delta S_{MM}> \quad \text{[Equation 2]}$$

Where:
$\Delta Gs_{olv}$=Polar solvation energy of molecule (estimated using generalized Born model);
$\Delta G_{np}$=Non-polar solvation energy (estimated using the solvent accessible surface area of the molecule);
T=Temperature;
$\Delta S_{MM}$=Entropy of the molecule; and
$\Delta E_{MM}$=Molecular mechanics energy of the molecule, i.e. sum of the internal energy of the molecule, electrostatics and van der Waals interaction (see Equation 3):

$$\Delta E_{MM} = E_{int} + E_{es} + E_{vdW} \quad \text{[Equation 3]}.$$

A glycomimetic as described herein may inhibit the binding of any of a variety of pathogens to their target. For example, a Type I, Type II, Type III, Type IV, or Type V glycomimetic as described herein may inhibit the binding of a pathogen to a sialylated galactose on the surface of a host cell or tissue. In some embodiments, the cell surface sialylated galactose includes a terminal Neu5Ac-α-(2-3)-Gal or a terminal Neu5Ac-α-(2-6)-Gal.

Target pathogens for inhibition by a glycomimetic of the present invention may include, but are not limited to, any of those described by Karlsson, 1995, *Curr Opin Struct Biol;* 5(5):622-635; Backenson et al., 1995, *Infect Immun;* 63(8): 2811-7 (*Borrelia burgdorferi* binding to glycosphingolipids); Kitamura et al., 1980, *Biochim Biophys Acta;* 628(3): 328-335 (binding of *Clostridium botulinum* neurotoxin and gangliosides); Kozaki et al., 1998, *Microb Pathog;* 25(2): 91-9 (interaction of ganglioside GT1b and *Clostridium botulinum* neurotoxins); Rogers and Snyder, 1981, *J Biol Chem;* 256:2402-7 (binding of tetanus toxin and mammalian brain membranes); Angstrom et al., 1994, *Proc Natl Acad Sci USA;* 91(25):11859-11863 (ganglioside-binding epitopes for the toxins of *Vibrio cholerae, Escherichia coli,* and *Clostridium tetani*); Babai et al., 2000, *Infect Immun;* 68(10):5901-5907; Sakarya and Oncu, 2003, *Med Sci Monit;* 9(3):RA76-82 (sialic acids and bacterial adhesins); Roche et al., 2004, *Infect Immun;* 72(3):1519-1529 (interaction of *Helicobacter pylori* and complex gangliosides); Connor et al., 1994, *Virol;* 205(1):17-23 (Receptor specificity in human, avian, and equine H2 and H3 influenza virus isolates); Sharon, 1987, *FEBS Lett;* 217(2):145-157; Imberty et al., 2005, *Microbes Infect;* 6(2):221-8; Delorme et al., 2001, *J Virol;* 75(5):2276-87 (glycosphingolipid binding specificities of rotavirus); Epand et al., 1995, *Biochem;* 34(3):1084-9 (binding of ganglioside GD1a and Sendai virus); and Sudha et al., 2001, *Curr Microbiol;* 42(6):381-7 (binding of *Shigella dysenteriae* 1 to human colonic mucin), each of which is incorporated by reference herein in its entirety.

A glycomimetic as described herein may bind to any of variety of pathogen protein targets, including, but not limited to, any of those shown in Table 1.

TABLE 1

Target Pathogens for Inhibition with Glycomimetics

| Toxin/Pathogen | Ligand | Reference |
| --- | --- | --- |
| *Bordetella pertussis* toxin | Neu5AcαGal | Karlsson, 1995, *Curr Opin Struct Biol;* 5(5): 622-635 |
| *Borrelia burgdorferi* | Neu5Acα(2-3)Gal/ Neu5Acα(2-8)Gal | Backenson et al., 1995, *Infect Immun;* 63(8): 2811-7 |
| *Clostridium botulinum* neurotoxin type A/B | Neu5Acα(2-3)Gal/ Neu5Acα(2-8)Gal | Kitamura et al., 1980, *Biochim Biophys Acta;* 628(3): 328-335 and Kozaki et al., 1998, *Microb Pathog;* 25(2): 91-9 |

TABLE 1-continued

Target Pathogens for Inhibition with Glycomimetics

| Toxin/Pathogen | Ligand | Reference |
|---|---|---|
| *Clostridium tetani* tetanus neurotoxin | Neu5Acα(2-3)Gal/ Neu5Acα(2-8)Gal | Rogers and Snyder, 1981, *J Biol Chem*; 256: 2402-7 and Angstrom et al., 1994, Proc *Natl Acad Sci USA*; 91(25): 11859-11863 |
| *Escherichia coli* | Neu5Ac-α(2-3)Gal | Babai et al., 2000, *Infect Immun*; 68(10): 5901-5907 |
| *Haemophilus influenzae* | Neu5Ac-α(2-3)Gal | Sakarya and Oncu, 2003, *Med Sci Monit*; 9(3): RA76-82 |
| *Helicobacter pylori* | Neu5Ac-α(2-3)Gal | Roche et al., 2004, *Infect Immun*; 72(3): 1519-1529 |
| Influenza | Neu5Acα(2-3)Gal/ Neu5Acα(2-6)Gal/ Neu5Acα(2-8)Gal | Connor et al., 1994, *Virol*; 205(1): 17-23 |
| *Mycoplasma gallisepticum* | Neu5Ac-α(2-3)Gal | Sharon, 1987, *FEBS Lett*; 217(2): 145-157 |
| *Mycoplasma pneumonia* | Neu5Ac-α(2-3)Gal | Sharon, 1987, *FEBS Lett*; 217(2): 145-157 |
| *Pseudomonas aeruginosa* | Neu5Ac-α(2-3)Gal | Imberty et al., 2005, *Microbes Infect*; 6(2): 221-8 |
| Rotavirus | Neu5Ac-α(2-3)Gal | Delorme et al., 2001, *J Virol*; 75(5): 2276-87 |
| Sendai virus | Neu5Ac-α(2-3)Gal | Epand et al., 1995, *Biochem*; 34(3): 1084-9 |
| *Shigella dysenteriae* | Neu5Ac-α(2-3)Gal | Sudha et al., 2001, *Curr Microbiol*; 42(6): 381-7 |
| *Streptococcus mitis* | Neu5Ac-α(2-3)Gal | Sharon, 1987, *FEBS Lett*; 217(2): 145-157 |
| *Streptococcus sanguinis* | Neu5Ac-α(2-3)Gal | Sharon, 1987, *FEBS Lett*; 217(2): 145-157 |
| *Vibrio cholerae* toxin | Neu5Ac-α(2-3)Gal/ Neu5Ac-α(2-8)Gal | Sharon, 1987, *FEBS Lett*; 217(2): 145-157 |

In some embodiments, a glycomimetic of the present invention is a glycomimetic of Type I, Type II, Type III, Type IV, or Type V as described herein, wherein X=CH2, Y=CH2 and R=H.

Figure 3A:
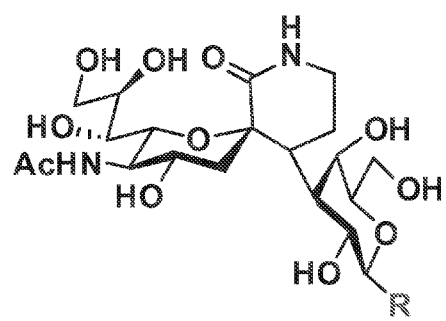
FIGS. 3A and 3B. Structures for optimization.
Figure 3B:
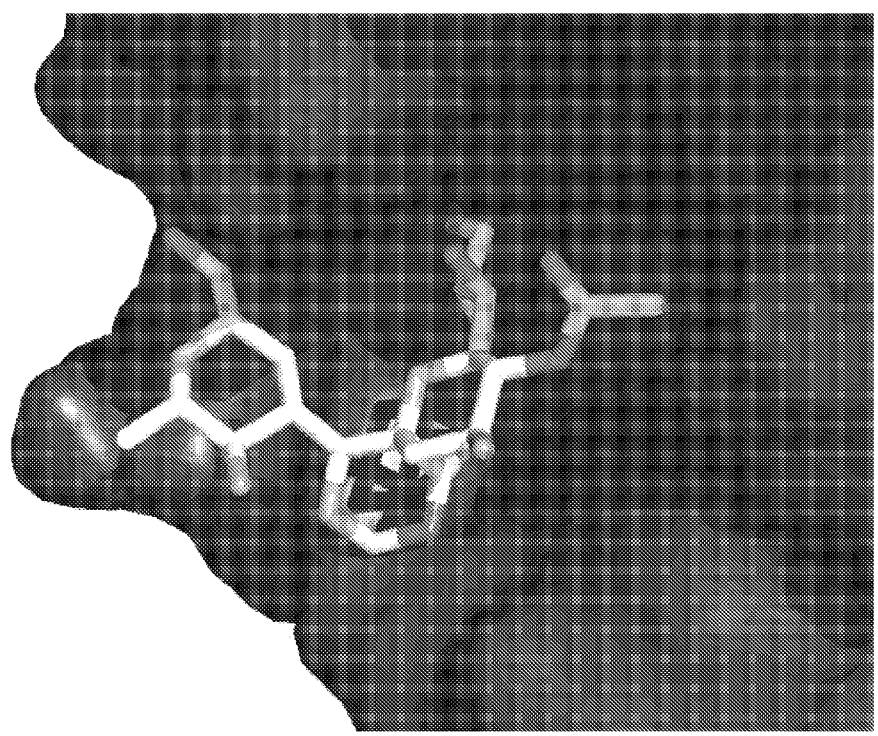
Figure 4:
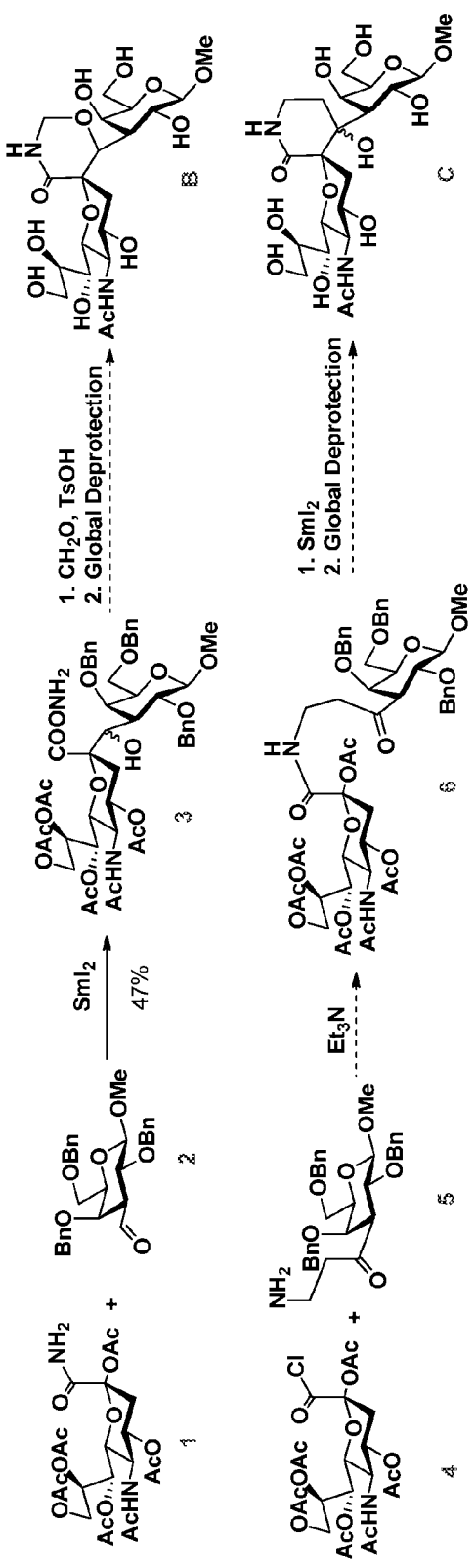
FIG. 4. Synthetic strategy towards glycomimetics B and C.
Figure 9:
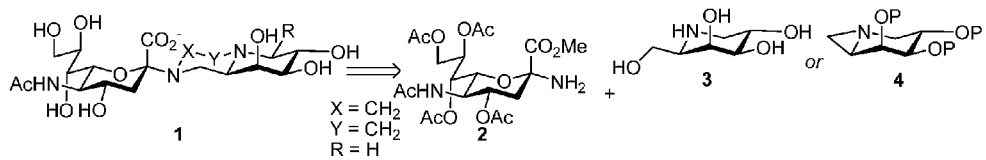
FIG. 9. Synthetic Scheme 2. Proposed synthetic routes to glycomimetic 1.
Figure 9:
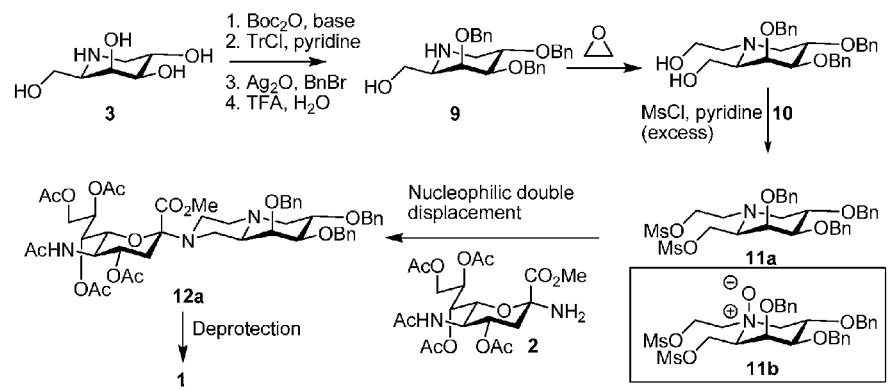
Figure 9:
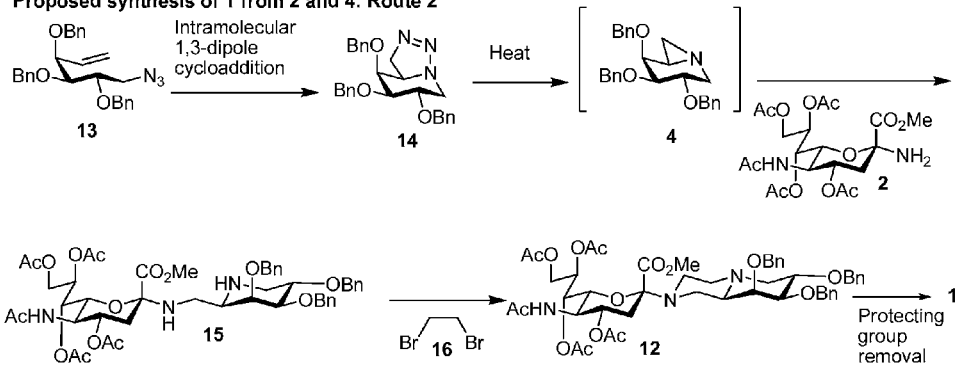
Figures 11, 12:
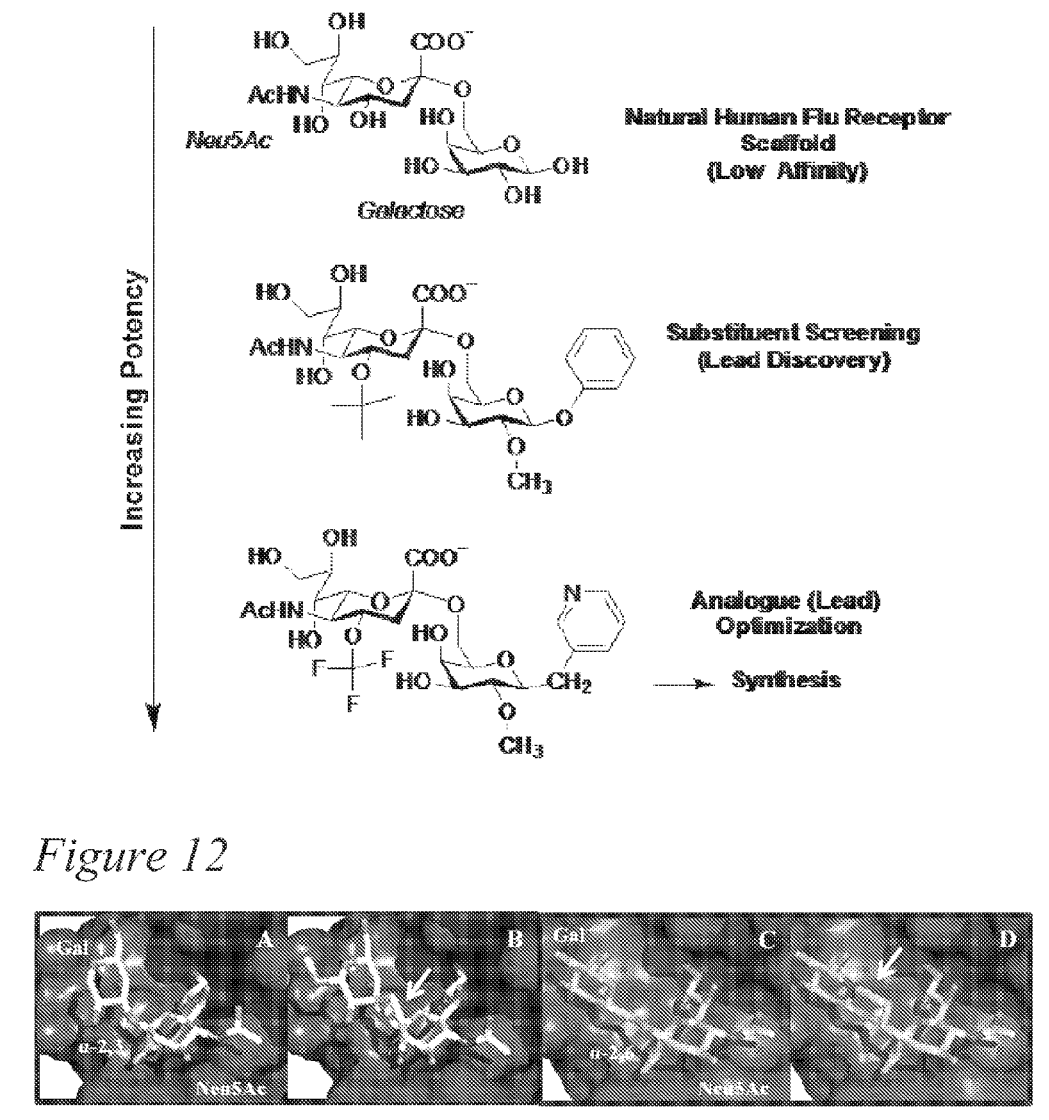
Figure 13:
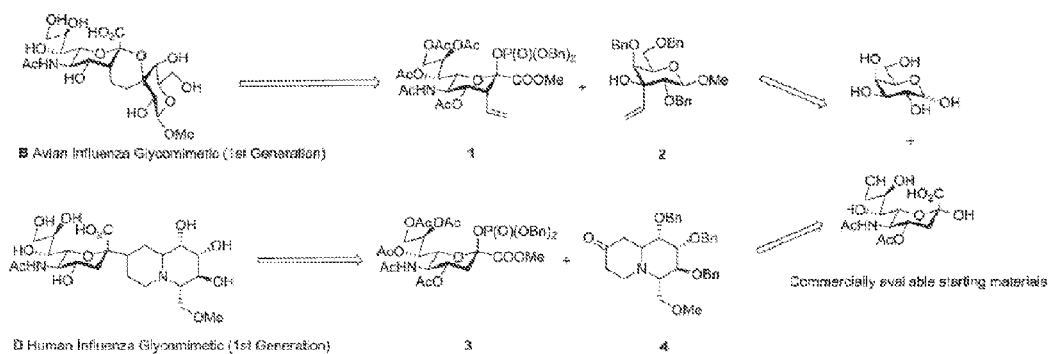
FIG. 13. Synthetic route to first generation glycomimetics B and D.

In some embodiments, a glycomimetic of the present invention is a glycomimetic described in the examples and figures included herewith. For example, in one embodiment, a glycomimetic is compound I, as shown in FIG. 9, where X=CH2, Y=CH2 and R=H, or a derivative thereof. This target 1 contains an N-glycosylated sialic acid in which the aglycon is a bicyclic iminosugar derivative (see FIGS. 7 and 9). In some embodiments, a glycomimetic has a structure as shown in FIG. 3A, FIG. 3B, or FIG. 11, or a derivative thereof. In some embodiments, a glycomimetic is compound B or compound C, as shown in FIG. 4, or a derivative thereof. In some embodiments, a glycomimetic is compound B or compound D, as shown in FIG. 13, or a derivative thereof.

The present invention includes methods of using glycomimetic compound as described herein and methods of synthesizing such glycomimetics. Also included in the present invention are compositions including one or more of the glycomimetic compounds described herein. Such a composition may include a pharmaceutically acceptable carrier. As used, a pharmaceutically acceptable carrier refers to one or more compatible solid or liquid fillers, diluents or encapsulating substances which are suitable for administration to a human or other vertebrate animal. Such a carrier may be pyrogen free. The present invention also includes methods of making and using the cytotoxic compounds, conjugates and compositions described herein.

The compositions of the present disclosure may be formulated in pharmaceutical preparations in a variety of forms adapted to the chosen route of administration. One of skill will understand that the composition will vary depending on mode of administration and dosage unit. For example, for parenteral administration, isotonic saline can be used. For topical administration a cream, including a carrier such as dimethylsulfoxide (DMSO), or other agents typically found in topical creams that do not block or inhibit activity of the peptide, can be used. Other suitable carriers include, but are not limited to, alcohol, phosphate buffered saline, and other balanced salt solutions. The compounds of this invention can be administered in a variety of ways, including, but not limited to, intravenous, topical, oral, subcutaneous, intraperitoneal, intramuscular, and intratumor deliver. In some aspects, the compounds of the present invention may be formulated for controlled or sustained release. In some aspects, a formulation for controlled or sustained release is suitable for subcutaneous implantation. In some aspects, a formulation for controlled or sustained release includes a patch. A compound may be formulated for enteral administration, for example, formulated as a capsule or tablet.

Administration may be as a single dose or in multiple doses. Preferably the dose is an effective amount as determine by the standard methods, including, but not limited to, those described herein. Those skilled in the art of clinical trials will be able to optimize dosages of particular compounds through standard studies. Additionally, proper dosages of the compositions can be determined without undue experimentation using standard dose-response protocols. Administration includes, but is not limited to, any of the dosages and dosing schedules, dosing intervals, and/or dosing patterns described in the examples included herewith.

In some embodiments, a pharmaceutical composition of a glycomimetic compound according to the present invention can be used as a traditional orally administered therapeutic. In some embodiments, a glycomimetic compound according to the present invention can be applied as an oral or nasal mucosal spray.

In some embodiments, a glycomimetic compound according to the present invention can be used to impregnate filters, masks, and clothing or any combination thereof. In some embodiments, a glycomimetic compound according to the present invention can be used to coat an indwelling medical device, such as for example, a catheter, a stent, an artificial joint, or a suture.

The agents of the present disclosure can be administered by any suitable means including, but not limited to, for example, oral, rectal, nasal, topical (including transdermal, aerosol, buccal and/or sublingual), vaginal, parenteral (including subcutaneous, intramuscular, and/or intravenous), intradermal, intravesical, intra-joint, intra-arteriole, intraventricular, intracranial, intraperitoneal, intranasal, by inhalation, or intralesional (for example, by injection into or around a tumor).

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intraperitoneal, and intratumoral administration. In this connection, sterile aqueous media that can be employed will be known to those of skill in the art. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA. Such preparation may be pyrogen-free.

For enteral administration, the inhibitor may be administered in a tablet or capsule, which may be enteric coated, or in a formulation for controlled or sustained release. Many suitable formulations are known, including polymeric or protein microparticles encapsulating drug to be released, ointments, gels, or solutions which can be used topically or locally to administer drug, and even patches, which provide controlled release over a prolonged period of time. These can also take the form of implants. Such an implant may be implanted within the tumor.

The compounds of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

The present invention includes a new class of carbohydrate-based anti-influenza agents that block the initial hemagglutinin-mediated adhesion of the virus to host cells. The agents may be used as therapeutics for treating or preventing influenza A in humans or livestock. In addition, other viruses and bacteria employ the same adhesion mechanism as influenza, thus the influenza blockers described herein may protect against a range of unrelated diseases. This is a novel strategy and is complementary to vaccination or to the use of current therapeutics that inhibit the action of viral neuraminidase.

A glycomimetic as described herein may be employed as a traditional small-molecule drug. A glycomimetic as described herein may also be employed in a formulation, in which the glycomimetic is conjugated to a multivalent carrier to generate a dendrimer (Sharon, 2006, *Biochimica Et Biophysica Acta-General Subjects;* 1760(4):527-537). The principle advantage of a dendrimer is that by increasing the number of ligands in a single molecular framework, avidity results in a significantly increased apparent affinity (Zhao et al., 2008, *Bioorg Med Chem;* 16:6333-6337). As a glycomimetic compound as described herein abrogates the initial adhesion of the influenza virus to host tissue, a glycomimetic in dendrimer form may be useful as a topically-applied agent.

A glycomimetic as described herein may be used as a carbohydrate-based anti-adhesive to reduce, inhibit or prevent infection. Adhesion of pathogenic organisms to host tissues is the prerequisite for the initiation of the majority of infectious diseases. In many systems, it is mediated by lectins present on the surface of the infectious organism that bind to complementary carbohydrates on the surface of the host tissues. Since anti-adhesive agents do not act by killing or arresting the growth of the pathogens, it is very likely that strains resistant to such agents will emerge at a markedly lower rate than of strains that are resistant to antibiotics.

A glycomimetic as described herein may be used as an anti-adhesive and may be applied as an oral or nasal mucosal spray. It may also be used to impregnate materials such as, for example, filters, masks, and clothing, to prevent the virus from crossing from the environment into the body. This method of trapping the virus could prevent the spread of influenza between humans (human formulation) or from birds to humans or other birds (avian formulation). Such an approach would be ideal for first responders or others anticipating a high risk of exposure.

The present invention includes methods of contacting cells with an agent or composition of the present invention. In some embodiments, the contacting step occurs in vitro. In some embodiments, the contacting step occurs in vivo. In some embodiments, the cells are present in a cell culture, a tissue, an organ, or an organism.

The first stage of infection for many pathogens is their adherence through specific interactions between surface proteins and glycans present on host cells. The present invention includes methods of preventing or reducing transmission and/or infection, the method including administering to a subject a glycomimetic or composition as described herein to prevent pathogen adhesion and thus, infection.

In some embodiments, a Type I, Type II, Type III, Type IV, or Type V glycomimetic of the present invention inhibits the binding of a pathogen to a sialylated galactose on the surface of a target cell or tissue. In some embodiments, the cell surface sialylated galactose includes a terminal Neu5Ac-α-(2-3)-Gal or Neu5Ac-α-(2,6)-Gal.

The present invention includes a method of treating a disorder in which a sialylated glycan receptor is implicated, the method including administering a glycomimetic or composition as described herein. In some embodiments, the disorder is mediated by an infectious agent that binds to a sialylated galactose on a host cell surface. In some embodiments, the sialylated galactose includes a terminal Neu5Ac-α-(2-3)-Gal or Neu5Ac-α-(2,6)-Gal.

The present invention includes methods of treating a disorder in which a sialylated glycan receptor is implicated, such as, for example, BK virus, *H. pylori, S. pneumoniae, M. pneumoniae, E. coli, N. meningitides, T. gondii*, and influenza A infections, the method including administering to a subject in need thereof a glycomimetic or composition as described herein.

As used herein "treating" or "treatment" can include therapeutic and/or prophylactic treatments. "Treating a disorder," as used herein, is not intended to be an absolute term. Treatment may lead to an improved prognosis or a reduction in the frequency or severity of symptoms. Desirable effects of treatment include preventing occurrence or recurrence of disease, alleviation of symptoms, diminishment of any direct or indirect pathological consequences of the disease, decreasing the rate of disease progression, amelioration or palliation of the disease state, and remission or improved prognosis. Likewise, the term "preventing," as used herein, is not intended as an absolute term. Instead, prevention refers to delay of onset, reduced frequency of symptoms, or reduced severity of symptoms associated with a disorder. Prevention therefore refers to a broad range of prophylactic measures that will be understood by those in the art. In some circumstances, the frequency and severity of symptoms is reduced to non-pathological levels. In some circumstances, the symptoms of an individual receiving the compositions of the invention are only 90, 80, 70, 60, 50, 40, 30, 20, 10, 5 or 1% as frequent or severe as symptoms experienced by an untreated individual with the disorder.

Therapeutically effective concentrations and amounts may be determined for each application herein empirically by testing the compounds in known in vitro and in vivo systems, such as those described herein, dosages for humans or other animals may then be extrapolated therefrom.

It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

Toxicity and therapeutic efficacy of the compounds and compositions of the present invention can be determined by standard pharmaceutical procedures in cell cultures or experimental animals, for example, for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio between $LD_{50}$ and $ED_{50}$. Compounds that exhibit high therapeutic indices are preferred. The data obtained from cell culture assays and animal studies can be used in formulating a range of dosage for use in humans. The dosage of such compounds lies preferably within a range of circulating concentrations that include the $ED_{50}$ with little or no toxicity. The dosage can vary within this range depending upon the dosage form employed and the route of administration utilized. The exact formulation, route of administration and dosage can be chosen by the individual physician in view of the patient's condition.

An agent as described herein may be administered at once, or may be divided into a number of smaller doses to be administered at intervals of time. For example, compounds of the invention may be administered repeatedly, e.g., at least 2, 3, 4, 5, 6, 7, 8, or more times, or may be administered by continuous infusion. It is understood that the precise dosage and duration of treatment is a function of the disease being treated and may be determined empirically using known testing protocols or by extrapolation from in vivo or in vitro test data. It is to be noted that concentrations and dosage values may also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed compositions and methods.

In some therapeutic embodiments, an "effective amount" of an agent is an amount that results in a reduction of at least one pathological parameter. Thus, for example, in some aspects of the present disclosure, an effective amount is an amount that is effective to achieve a reduction of at least about 10%, at least about 15%, at least about 20%, or at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, or at least about 95%, compared to the expected reduction in the parameter in an individual not treated with the agent.

In some aspects of the methods of the present invention, a method further includes the administration of one or more additional therapeutic agents. One or more additional therapeutic agents may be administered before, after, and/or coincident to the administration of a glycomimetic compound as described herein. A glycomimetic compound and additional therapeutic agents may be administered separately or as part of a mixture or cocktail. In some aspects of the present invention, the administration of glycomimetic compound may allow for the effectiveness of a lower dosage of other therapeutic modalities when compared to the administration of the other therapeutic modalities alone, providing relief from the toxicity observed with the administration of higher doses of the other modalities.

In some aspects of the methods of the present invention, the administration a compound as described herein and the at least one additional therapeutic agent demonstrate therapeutic synergy. In some aspects of the methods of the present invention, a measurement of response to treatment observed after administering both a glycomimetic compound as described herein and the additional therapeutic agent is improved over the same measurement of response to treatment observed after administering either the glycomimetic compound or the additional therapeutic agent alone.

As used herein, the term "subject" includes, but is not limited to, humans and non-human vertebrates. In preferred embodiments, a subject is a mammal, particularly a human. A subject may be an individual. A subject may be an "individual," "patient," or "host. Non-human vertebrates include livestock animals, companion animals, and laboratory animals. Non-human subjects also include non-human primates as well as rodents, such as, but not limited to, a rat or a mouse. Non-human subjects also include, without limitation, chickens, horses, cows, pigs, goats, dogs, cats, guinea pigs, hamsters, mink, and rabbits.

As used herein "in vitro" is in cell culture and "in vivo" is within the body of a subject. As used herein, "isolated" refers to material that has been either removed from its natural environment (e.g., the natural environment if it is naturally occurring), produced using recombinant techniques, or chemically or enzymatically synthesized, and thus is altered "by the hand of man" from its natural state.

As a glycomimetic of the present invention prevents the initial adhesion of a pathogen, such as, for example, influenza virus, to mammalian cells or tissue, a glycomimetic as described herein may be effectively used as a topically-applied agent, oral spray, or nasal mucosal spray. In addition, because several other pathogens employ the same adhesion mechanism as influenza (Kirschner et al., 2008, *J Comput Chem;* 29:622-655), a glycomimetic as described herein may in addition to blocking influenza transmission and infection, may protect against a range of unrelated diseases.

In addition to administration to a subject for therapeutic use, a glycomimetic as described herein may be used to impregnate filters, masks, and clothing or any combination thereof in prophylactic strategies to reduce transmission and infection.

The present invention and/or one or more portions thereof may be implemented in hardware or software, or a combination of both. For example, the functions described herein may be designed in conformance with the principles set forth herein and implemented as one or more integrated circuits using a suitable processing technology, e.g., CMOS. As another example, the present invention may be implemented using one or more computer programs executing on programmable computers, such as computers that include, for example, processing capabilities, data storage (e.g., volatile and nonvolatile memory and/or storage elements), input devices, and output devices. Program code and/or logic described herein is applied to input data to perform functionality described herein and generate desired output information. The output information may be applied as an input to one or more other devices and/or processes, in a known fashion. Any program used to implement the present invention may be provided in a high level procedural and/or object orientated programming language to communicate with a computer system. Further, programs may be implemented in assembly or machine language. In any case, the language may be a compiled or interpreted language. Any such computer programs may preferably be stored on a storage media or device (e.g., ROM or magnetic disk) readable by a general or special purpose program, computer, or a processor apparatus for configuring and operating the computer when the storage media or device is read by the computer to perform the procedures described herein. The system may also be considered to be implemented as a computer readable storage medium, configured with a computer program, where the storage medium so configured causes the computer to operate in a specific and predefined manner to perform functions described herein.

The present invention and/or one or more portions thereof include circuitry that may include a computer system operable to execute software to provide for the design and/or characterization of a glycomimetic structure. Although the circuitry may be implemented using software executable using a computer apparatus, other specialized hardware may also provide the functionality required to provide a user with information as to the physiological state of the individual. As such, the term circuitry as used herein includes specialized hardware in addition to or as an alternative to circuitry such as processors capable of executing various software processes. The computer system may be, for example, any fixed or mobile computer system, e.g., a personal computer or a minicomputer. The exact configuration of the computer system is not limiting and most any device capable of providing suitable computing capabilities may be used according to the present invention. Further, various peripheral devices, such as a computer display, a mouse, a keyboard, memory, a printer, etc., are contemplated to be used in combination with a processing apparatus in the computer system.

In view of the above, it will be readily apparent that the functionality as described herein may be implemented in any manner as would be known to one skilled in the art.

The description provided herewith exemplifies illustrative embodiments. In several places throughout the application, guidance is provided through lists of examples, which examples can be used in various combinations. In each instance, the recited list serves only as a representative group and should not be interpreted as an exclusive list.

The present invention is illustrated by the following examples. It is to be understood that the particular examples, materials, amounts, and procedures are to be interpreted broadly in accordance with the scope and spirit of the invention as set forth herein.

EXAMPLES

Example 1

Computational Design of Glycomimetics

Many pathogens, such as avian influenza, *H. pylori* and *S. pneumonia*, employ cell-surface glycans which terminate in Neu5Ac-α-(2-3)-Gal as their adhesion partner (Ofek et al., 2003, *FEMS Immunol Med Microbiol;* 38:181-191). As a result, a glycomimetic anti-adhesive drug based on this structure could potentially prevent infection. In this project, sialylated galactose (α-Neu5Ac-(2,3)-Gal) will be employed as a scaffold in the design of high-affinity inhibitors of influenza A virus adhesion. Advanced computational methods will be employed to focus the number of glycomimetic synthetic targets to a select few that have the highest probability to block influenza adhesion and infection. Several glycomimetic lead scaffolds are currently being synthesised and their ability to inhibit avian influenza haemagglutinin will be assayed. The synthesis of lead compounds will employ commercially available galactose and sialic acid starting materials. The computational methods which are being used include both molecular dynamics (MD) and molecular mechanics—Poisson Boltzmann solvation approximation (MM-PBSA) calculations. Substituent remodelling was carried out using BOMB to scan libraries containing over 500 drug-like substituents (Jorgensen, 2009, *Acc Chem Res;* 42:724-733).

Example 2

Glycomimetics to Inhibit Pathogen-Host Adhesion

Many pathogens, such as avian influenza, *H. pylori* and *S. pneumonia*, employ cell-surface glycans which terminate in Neu5Ac-α-(2-3)-Gal as their adhesion partner (Ofek et al., 2003, *FEMS Immunology & Medical Microbiology;* 38:181-191). As a result, a glycomimetic anti-adhesive drug based on this structure could potentially prevent infection. In this project, sialylated galactose (α-Neu5Ac-(2,3)-Gal) A will be employed as a scaffold in the design of high-affinity inhibitors of influenza A virus adhesion. Advanced computational methods were employed to focus the number of glycomimetic synthetic targets to a select few that have the highest probability to block influenza adhesion and infection. Several glycomimetic lead scaffolds are currently being synthesized and their ability to inhibit avian influenza haemagglutinin (HA) will be assayed. The computational methods which are being used include both molecular dynamics (MD) and molecular mechanics—Poisson Boltzmann solvation approximation (MM-PBSA) calculations. Substituent remodelling was carried out using BOMB to scan libraries containing over 500 drug-like substituents (Jorgensen, 2009, *Accounts of Chemical Research;* 42:724-733).

Computing Methods

Figure 1B:
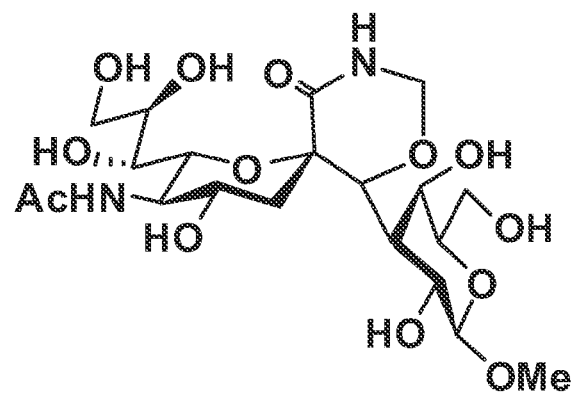
Figure 1C:
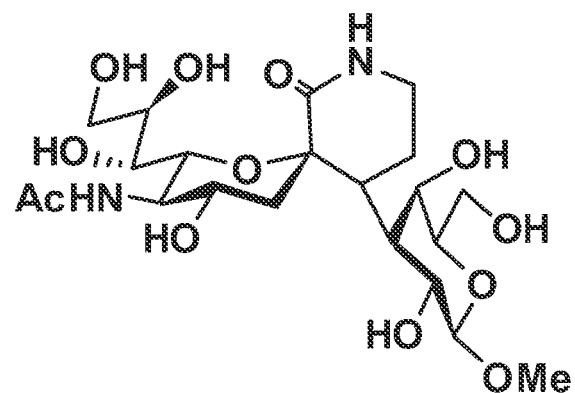

Structure B and C, as shown in FIGS. 1B and 1C were built using USFC Chimera (Pettersen et al., 2004, *J Computational Chemistry;* 25:1605-1612). B and C were then superimposed on to A (FIG. 1A) in complex with H5 HA structure 1JSN from the PDB (Ha et al., 2001, *Proc Natl Acad Sci;* 98:11181-11186). Antechamber, from the AMBER suite, was run to find missing force field parameters and provide reasonable substitutes. Using AmberTools 1.5 coordinate and topology files were created in tLEaP utilizing the General Amber Force Field (GAFF) and AMBER ff99SB. The system was solvated using TIP3P water with a 10 Å cut-off. All molecular dynamics (MD) simulations were carried out using AMBER. The water was minimized initially over 10,000 steps. The system was energy minimized using 5,000 steps of steepest decent followed by 5,000 steps of conjugate gradient. The system was heated to 300K over 100,000 steps. The simulation ran for 10 ns. α-carbons of the protein backbone were restrained throughout. Ligand heavy atoms were restrained for minimization and heating. MM/PBSA (Molecular Mechanics-Poisson Boltzmann Surface Area) was used to estimate $\Delta G_{binding}$. B and C were also simulated in solution for 100 ns. VMD was used to visualize the trajectories and to calculate the Φ and Ψ angles of the C-glycosidic linkage in B (Humphrey et al., 1996, *J Molec Graphics*; 14.1:33-38). These were compared to the Φ and Ψ angles from α-Neu5Ac-(2,3)-Gal complexed with influenza HA in the PDB (Gamblin et al., 2004, *Science*; 303:1838-1842; Lin et al., 2009, *Virology*; 392:73-81; and Ha et al., 2003, *Virology*; 309:209-218). FIG. 3A illustrates the position of the substitution (R) on structure B carried out in BOMB. All substituents contained in the library were scanned. The scoring function was modified to allow for the specificities of this case. FIG. 3B illustrates the structure for optimization with HA.

Results

Figure 2:
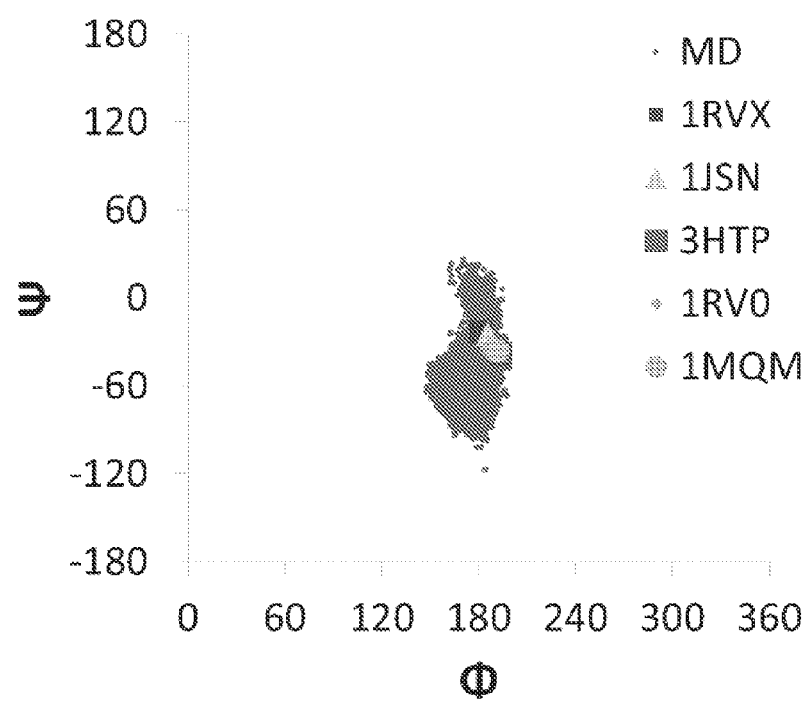
FIG. 2. φ and ψ angles from MD stimulation compared to crystal structure with native ligand.

The angles of the C-glycosidic linkage of B conformed well to the crystal structures of similar linkages are shown in FIG. 2. MM/PBSA results for structures B and C are presented in Table 2. Both scaffolds score similarly well. The BOMB results are presented in Table 3. The scores for the best 15 have been normalized against the starting structure. The table demonstrates a trend for electron rich substituted cyclic substituents. The scoring function used promotes good solute electrostatic interactions, which has appeared to heavily influence results.

TABLE 2

MMPBSA Data

| Scaffold | $\Delta G_{binding}$ | $\Delta G_{Electot}$ | $\Delta G_{VDWtot}$ |
| --- | --- | --- | --- |
| Structure B | −34.03 | −3.88 | −30.15 |
| Structure C | −34.33 | −1.97 | −32.36 |

TABLE 3

Potential substituents for putative anti-adhesives

| R | SCORE |
| --- | --- |
| hydrogen | 0.00 |
| m-aminophenyl | −0.65 |
| p-aminophenyl | −0.55 |
| 2-pyrrolyl | −0.53 |
| o-aminophenyl | −0.50 |
| 3-bromo-4-methoxyphenyl | −0.49 |
| 2-naphthyl | −0.43 |
| 3-pyrrolyl | −0.38 |
| p-bromophenyl | −0.37 |
| 4-methyl,2-furanyl | −0.36 |
| 3-chloro-4-methoxyphenyl | −0.35 |
| 2,5-dimethyl-4-methoxyphenyl | −0.35 |
| 3-azetidinyl (N-linking) | −0.34 |
| p-isopropylphenyl | −0.34 |
| p-aminomethylphenyl | −0.34 |
| p-mercaptophenyl (p-PhSH) | −0.33 |

Synthetic Approach

Glycomimetics B and C are currently being synthesized using the approach that is illustrated in FIG. 4. The syntheses employ commercially available galactose and sialic acid starting materials. Strategic protecting group introduction and manipulation provided the monosaccharide building blocks 1, 2, 4, and 5. C-glycosylation, lactam ring formation and deprotection will provide the target compound B. The target compound C will be obtained by tethering the monosaccharides via an amide linkage, followed by C-glycosylation, and finally deprotection. Currently the synthesis of the pseudo-disaccharide 3 has been completed using the samarium diiodide mediated coupling of galactoside 2 and sialoside 1. The formation of the lactam ring is now being investigated. In the near future, the synthesis of the tethered disaccharide 6 will be carried out from monosaccharides 4 and 5.

Conclusions

On the basis of our initial structural and energetic analyses, a first generation of scaffolds has been developed for the ligand which mimics the two terminal residues of the influenza receptor glycans. These target compounds are more rigid than the native receptor and therefore should benefit from less entropic penalty upon binding. After the completion of the synthesis, the synthetic anti-adhesives will be assayed for their inhibitory ability of glycan-HA interactions. The techniques of surface plasmon resonance (SPR) and isothermal titration calorimetry will provide direct measures of binding kinetics and thermodynamics. Lead by BOMB studies substituted versions of the scaffolds will be synthesised and assayed with a view to increasing binding affinity.

Example 3

Anti-Adhesion Based Influenza Blockers

With this example, a new class of anti-influenza therapeutics, based on blocking the initial adhesion between the viral surface hemagglutinin (HA) protein and the receptor glycans of host cells will be developed. In contrast to NA inhibition, by preventing viral adhesion, infection may be avoided entirely. These therapeutics will be a glycomimetic based on a molecular scaffold similar to the natural receptor, and will be developed through a close interplay between computational simulations, chemical synthesis and biological evaluation.

In this example, a fragment of the natural influenza receptor glycans found on host cells Neu5Ac-(α-(2-6)-Gal) will be employed as a chemical scaffold in the rational design of high-affinity inhibitors of hemagglutinin-mediated influenza A virus adhesion. This is a new and complementary strategy to existing therapeutics that target the inhibition of viral neuraminidase.

The development of anti-adhesion influenza blockers will include the following: the computationally-guided design of potential carbohydrate-based inhibitors of influenza hemagglutinin-glycan adhesion; the synthesis of optimized glycomimetic lead compounds; and the biophysical characterization of the ability of the glycomimetics to inhibit hemagglutinin binding to glycan receptors.

Rational Design of Glycomimetics. A prerequisite to the computation molecular design process is the ability to accurately model the structures and energies of the ligand-protein complexes. In the case of carbohydrate-protein complexes, a widely used set of parameters (GLYCAM) has been developed (Kirschner et al., 2008, *J Comput Chem*; 29:622-655) for use with the AMBER force field (Case et al., 2005, *J Comput Chem*; 26:1668-1688) for classical mechanical simulations. To provide as rigorous a model as possible, molecular dynamics (MD) simulations are employed, in the presence of explicit water and counter ions, as necessary to achieve charge neutrality. These simulations have been performed on the complex of the native glycan fragment with the HA1 domain of hemagglutinin (FIGS. 5A and 5B) for which x-ray structures are available for comparison. The simulations correctly maintained the 3D orientation of the ligand in the binding site, as indicated by the root mean square deviation (RMSD) in the ligand position plotted over the course of the simulation (see Table 4). See also Fadda and Woods, 2010, *Drug Discov Today;* 15(15-16):596-609.

There are several extremely important benefits of the MD simulations over simple energy minimization. Notably, MD simulations permit the effects of temperature and solvent to be included, and enable the generation of a statistically relevant ensemble of conformations. From this ensemble it is possible to compute average properties, such as interaction energies (Table 4). Similar calculations have been reported for several hemagglutinin-carbohydrate complexes using the GLYCAM force field, and the data computed in Table 4 are typical. The ability to partition the energies into contributions from electrostatic and van der Waals interactions, as well as from desolvation entropy are crucial to rational design. In addition, it is well established that carbohydrate-protein complexes display enthalpy-entropy compensation (Chervenak and Toone, 1995, *Biochem;* 34:5685-5695), and an examination of the data in Table 4 illustrates that more-simplistic modeling that neglects entropic effects would greatly overestimate the interaction energy. It is also noteworthy that desolvation effects approximately cancel benefits arising from direct electrostatic interactions (Woods and Tessier, 2010, *Curr Opin Struct Biol;* 20(5):575-583; and Newhouse et al., 2009, *J Am Chem Soc;* 131:17430-17422), and it is therefore essential to include the effects of desolvation in the analysis.

Table 4 shows binding energies for the native trisaccharide glycan (FIG. 1) with influenza HA, based on the crystal of the 1934 H1 co-complex (Gamblin et al., 2004, *Science;* 303:1838-1842), computed with the MM-PBSA method from a 5 ns MD simulation with GLYCAM/AMBER. Values are the difference in energies between the complex and free ligand and protein.

TABLE 4

Binding energies for the native trisaccharide glycan with influenza HA.
Average Binding Energy Contributions (kcal/mol)

| | |
|---|---|
| $\Delta E_{Direct\ Electrostatics}{}^{a}$ | −187.9 |
| $\Delta G_{Polar\ Desolvation}{}^{b}$ | 175.7 |
| Total Electrostatic Interaction | −12.2 |
| $\Delta E_{VDW}{}^{c}$ | −22.4 |
| $\Delta G_{Nonpolar\ Desolvation}{}^{d}$ | −5.4 |
| Total Non-Polar and van der Waals | −27.8 |
| $-T\Delta S_{TRV}{}^{e}$ | 28.0 |
| $-T\Delta S_{c}{}^{f}$ | 3.5 |
| Total Entropic Penalty | 31.5 |
| $\Delta G_{Binding}$ | −8.5 |

[a] Ligand-protein electrostatics from force field;
[b] Desolvation electrostatics from Poisson Boltzman (PB) approximation.
[c] Ligand-Protein van der Waals from force field;
[d] Non-polar desolvation from PB;
[e] translational, rotational and vibrational entropy from analysis of normal modes;
[f] Conformational entropy from an analysis of glycosidic torsion fluctuations (Kadirvelraj et al., 2006, *PNAS,* 103(21): 8149-8154; and Karplus and Kushick, 1981, *Macromol;* 14: 325-332).

Figure 5A:
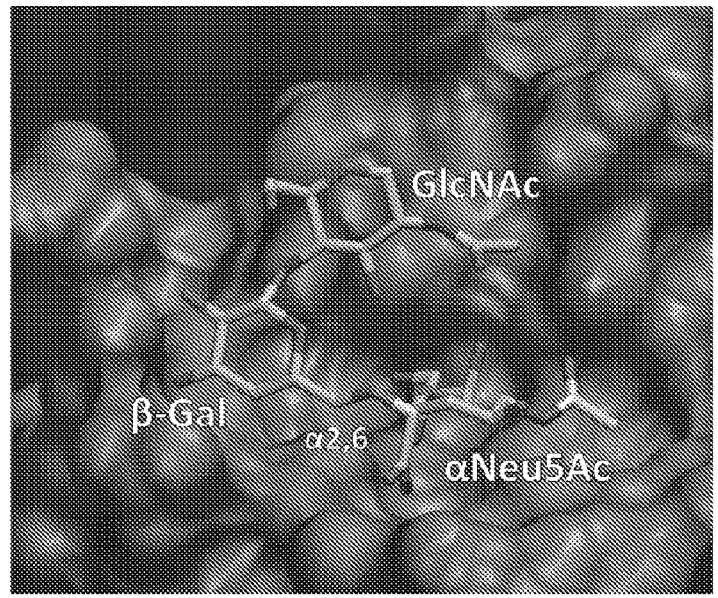
FIGS. 5A and 5B. Structure of the influenza receptor glycan sequence in complex with HA1 domain (FIG. 5A) and in complex with the conformationally-restricted glycomimetic scaffold (FIG. 5B).
Figure 5B:
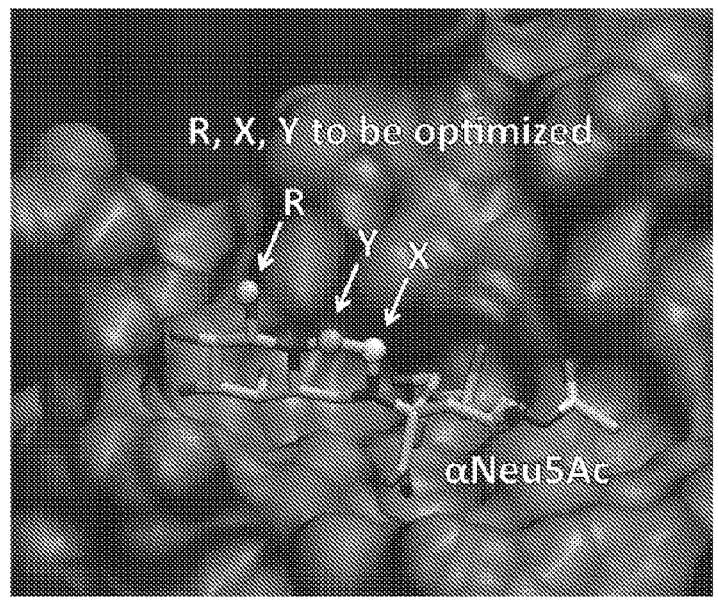

Glycomimetic Scaffold. It is important to note that approximately 85% of the total binding energy arises from interactions with only the terminal two residues (Neu5Ac-α-2-3-Gal) (Newhouse et al., 2009, *J Am Chem Soc;* 131: 17430-17422). On the basis of our initial structural and energetic analyses we have developed a scaffold for the ligand that mimics the terminal two residues of all human influenza receptor glycans and is more rigid than the native receptor, and therefore should benefit from less entropic penalty upon binding (FIGS. 5A and 5B). The native ligand is highly flexible and the stiffening that occurs upon binding results in a conformational entropy penalty ($-T\Delta S_c$) of approximately 3.5 kcal/mol. The fused ring structure of the glycomimetic scaffold (FIG. 1) introduces rigidity into the ligand, and preorders it into the correct conformation. This should result in a significant reduction in the entropy penalty. Reducing the conformational entropy penalty to zero, without any additional structural modifications, would lead to an affinity enhancement of approximately 340 fold. Notably, however, this scaffold has the important feature that all of the chemical alterations to the glycomimetic occur on the solvent side (R, X, Y in FIG. 5B), rather than on the contact face, of the protein-ligand complex. That is, it has correct shape and charge complementarity with respect to the protein surface. This feature will be beneficial for ensuring that naturally-occurring mutations in the protein surface are less likely to cause drug resistance, in contrast to the resistance developing against the neuraminidase inhibitor Tamiflu (Ferraris and Lina, 2008, *J Clin Virol;* 41(1):13-19).

Assays for influenza hemagglutinin-glycan binding. In order to facilitate the characterization of influenza virus binding, a multiplexed microsphere-based assay for simultaneous antibody-based strain typing and sub-typing (Yan et al., 2005, *Analyt Chem;* 77:7673-7678), as well characterization of carbohydrate receptor binding preference has been developed. For strain typing and sub-typing, distinct optically-encoded microspheres were functionalized with antibodies specific for influenza virus A sub-types H1N1 and H5N1. For receptor preference analysis, microspheres were functionalized with avian 2,3 influenza receptors or human 2,6 influenza receptors. Microsphere-bound virus was detected using fluorescence-labeled anti-influenza virus antibodies and measured using flow cytometry.

Figure 6:
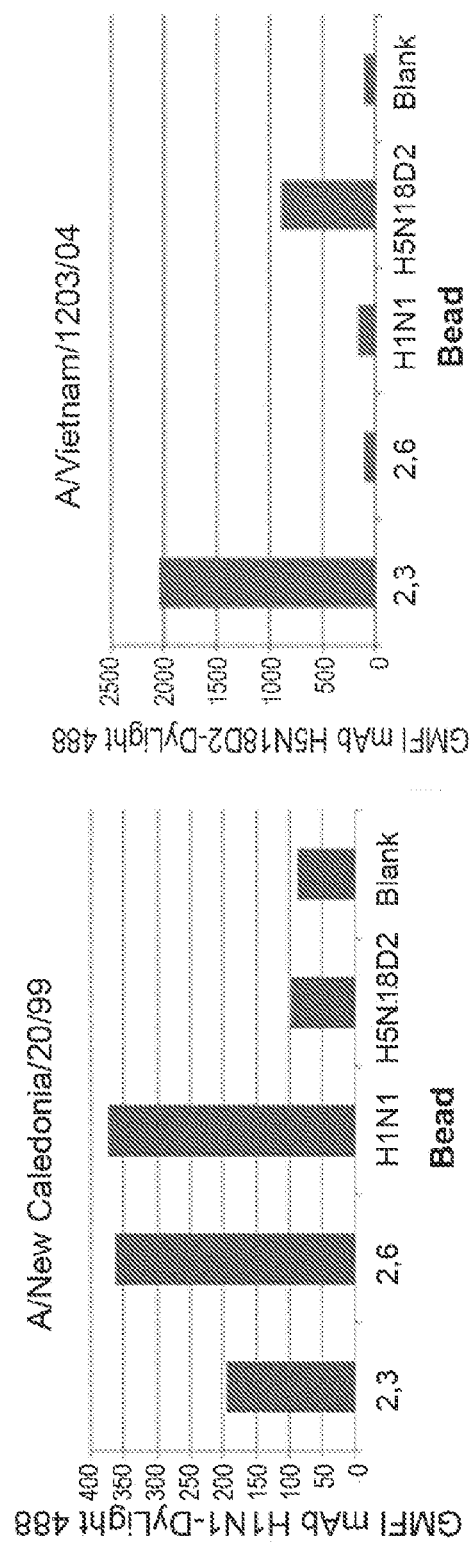
FIG. 6. Discrimination of human and avian-type influenza virus by binding to 2,3 or 2,6 receptors displayed on microspheres.

The data in FIG. 6 illustrate that the assay detects the binding of inactivated influenza virus to microspheres bearing carbohydrates with the appropriate receptor specificity. In addition the assay can identify the viral sub-type, as demonstrated with virus strains that have been previously characterized by other methods including hemagglutination and glycan microarray (FIG. 6).

The human influenza strain A/New Calcdonia/20/99 (H1N1) displayed its known preference for the human 2,6 receptor over the avian 2,3 receptor. The HPAI A/Vietnam/1203/04 (H5N1) demonstrated a clear preference for the 2,3 receptor. These assays work equally well, in fact slightly better, with recombinant HA protein (Yan et al., 2005, *Analyt Chem;* 77:7673-7678). Because a minimal amount of reagent is required, this assay will be amenable to high throughput screening of HA's for receptor specificity, as well as high throughput screening of inhibitors of HA.

Figure 7:
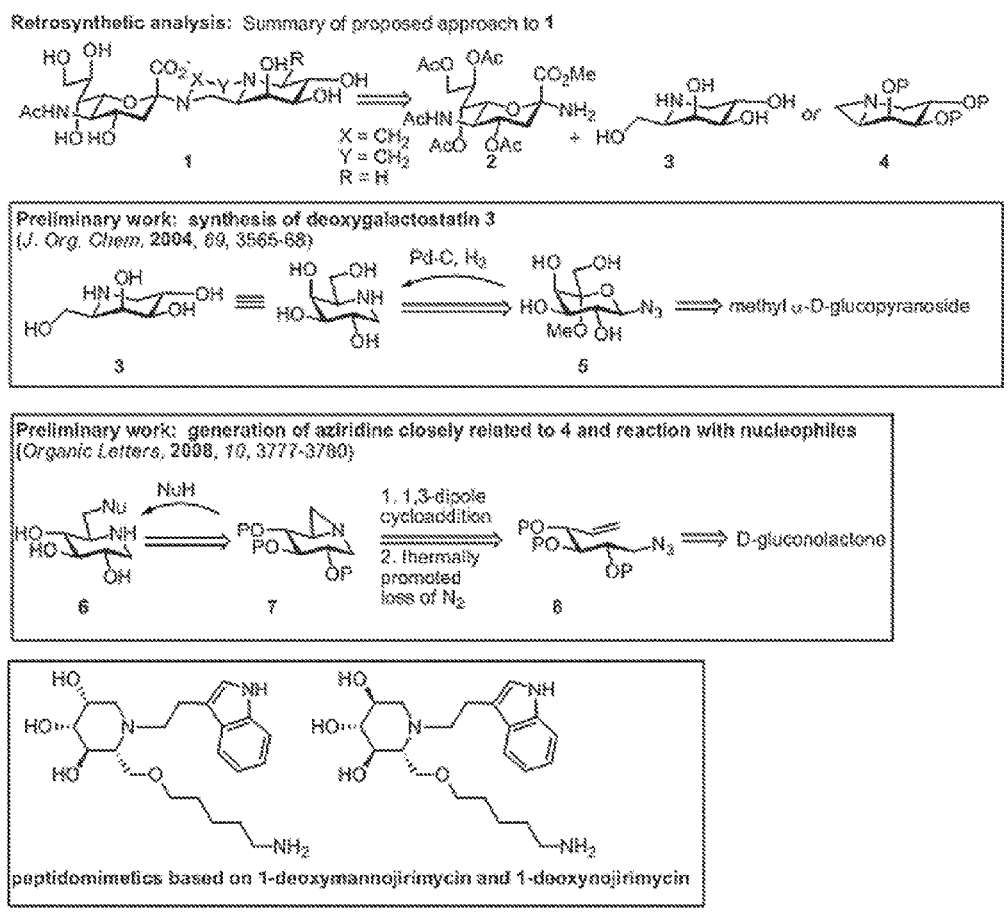
FIG. 7. Synthetic Scheme 1. Preliminary synthetic steps toward the scaffold synthesis.

Synthesis. Preliminary computational studies have led to the design of glycomimetics as potential inhibitors of influenza virus; the first target structure chosen for synthesis will be 1 where $X=CH_2$, $Y=CH_2$ and $R=H$. This target 1 contains an N-glycosylated sialic acid in which the aglycon is a bicyclic iminosugar derivative. The iminosugars are of interest as they show glycosidase activity and are nitrogen analogues of monosaccharides such as D-glucose, D-galactose and other sugars. More specifically the bicyclic iminosugar fragment is the nitrogen analogue of D-galactose and is called 1-deoxygalactostatin 3. As shown in FIG. 7 (Scheme 1) and FIG. 9 (Scheme 2), 1-deoxygalactostatin 3 or its related aziridine 4 and the sialic acid amine 2 will be used as building blocks for the synthesis of 1. The sialic acid amine 2 is known in the literature 1-Deoxygalactostatin (and other closely related iminosugars such as the glucose analogue 1-deoxynojirimycin and mannose analogue 1-deoxymannojirimycin) have been prepared by the co-applicants group. They have also been prepared by a number of other research groups and thus an abundance of routes to such compounds have been described in the literature (Cronin and Murphy, 2005, *Org Lett;* 7:2691-2693; Gouin and Murphy, 2005, *J Org Chem;* 70:8527-8532; Zhao et al., 2008, *Bioorg Med Chem;* 16:6333-6337; Chagnault et al., 2008, *Chem Med Chem;* 3:1071-76; and Danieli et al., 2007, *Scaffold Tetrahedron;* 63:6827-34).

FIG. 7 illustrates synthetic Scheme 1 and shows preliminary synthetic steps toward the scaffold synthesis. The proposed building block 3 has been generated via a cascade reaction promoted by catalytic hydrogenation from a 5-C-methoxy-galactopyranosyl azide derivative 5 (yield=~70%) (McDonnell et al., 2004, *J Org Chem;* 69:3565-3568). Various others have also been prepared by this route which can be used in a general synthesis of iminosugars. The glucose analogue aziridine 7 has been prepared by a stereospecific intramolecular cycloaddition of azide 8 and shown that its reaction with nucleophiles can give iminosugar derivatives 9 (Zhou and Murphy, 2008, *Org Lett;* 10:3777-3780). This supports the synthesis of 1 as illustrated in FIG. 9 (Scheme 2) from 4, which will be prepared from galactose/arabinose. Peptidomimetics 6-8 based on 1-deoxynojirimycin and 1-deoxmannojirimycin (synthesised structures) shown in Scheme 1 (FIG. 7) have been synthesized using elaborate synthetic sequences that involve a variety of protecting group manipulations and N-alkylation reactions. In addition, castanospermine and its derivatives have been synthesized, supporting the preparation of bicyclic iminosugars (Cronin and Murphy, 2005, *Org Lett;* 7:2691-2693). The generation of multivalent glycomimetics (Gouin and Murphy, 2005, *J Org Chem;* 70:8527-8532) will be utilized in the creation of carbohydrate-based dendrimers (Cronin and Murphy, 2005, *Org Lett;* 7:2691-2693).

Experimental Design and Methods

Figure 8:
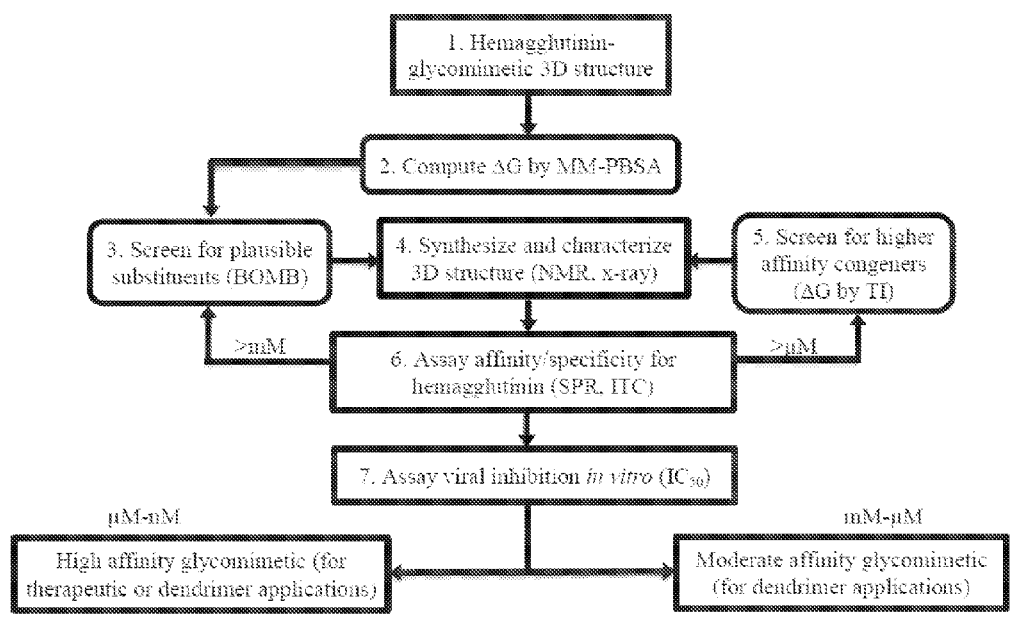
FIG. 8. Glycomimetic lead discovery and optimization protocol.

To develop an optimal inhibitor, the iterative procedure shown in FIG. 8 will be used, in which computational predictions guide synthesis, and biological assays with inactivated virus are employed to ultimately assess performance. The design process will begin with the crystal structures of H1 influenza hemagglutinin complexed with human glycans (Gamblin et al., 2004, *Science;* 303:1838-1842), for which extensive structural and biological affinity data are available (Stevens et al., 2006, *Nature;* 4:857-864). These structures will be subjected to refinement by molecular dynamics simulation in the presence of explicit water at room temperature (Step 2, FIG. 8).

Computational simulations using the BOMB method will be employed to identify pendant groups that may be added to the basic scaffold (FIG. 5) to enhance affinity (Step 3, FIG. 8), and optimal leads evaluated to synthetic accessibility. The compounds will be assayed for their ability to bind to HA (Step 6, FIG. 8), and those that are higher affinity than the native glycan receptor will be further assayed for their ability to block the adhesion of inactivated virus to glycan receptors (Step 7, FIG. 8). Sub-optimal binders, that nevertheless have better affinities than the native ligand will be subjected to a second level of computational discovery, based on the application of thermodynamic integration (TI) calculations. TI calculations are extremely useful for estimating the effect of modest structural alterations on affinity (for example, OH to Ome) (Jorgensen, 2004, *Science;* 303(5665):1813-1818). Such a strategy has not yet been applied in glycomimetic design, but appears to be highly appropriate, particularly given the challenges associated with combinatorial synthetic carbohydrate chemistry (Seeberger, 2002, *Combinatorial Chemistry;* 6(3):289-296).

Computational Methods

Molecular dynamics (MD) simulation. All MD simulations will be performed under constant pressure and temperature (NPT) conditions with the SANDER module of AMBER (Case et al., 2005, *J Comput Chem;* 26:1668-1688) and the TIP3P (Jorgensen, 1981, *J Am Chem Soc;* 103:341-345) water model. All atoms will be treated explicitly. Periodic boundary conditions will be applied together with Ewald treatment of long-range electrostatics. Typically, the oligosaccharides, or oligosaccharide-protein complexes will be solvated by 10-20000 TIP3P water molecules, in a periodic cube. Initial configurations will be generated using the GLYCAM web-tool (available on the worldwide web at glycam.ccrc.uga.edu). Experimental observables such as NOE intensities will be computed wherever possible (Yongye et al., 2008, *J Phys Chem A;* 112(12):2634-2639) and used to check the accuracy of the simulations. For further details see Gonzalez-Outeriño et al. (Gonzalez-Outeriño et al., 2005, *Carbohydr Res;* 340:1007-1018). For very flexible glycans, accurate simulations may require extremely long sampling times (up to μs) nevertheless, such simulations are generally able to reproduce experimental NMR data for carbohydrates in solution (Gonzalez-Outeriño et al., 2005, *Carbohydr Res;* 340:1007-1018; Lycknert et al., 2002, *J Phys Chem B;* 106:5275-5280; Lycknert et al., 2004, *Carbohydr Res;* 339(7):1331-8; Lommerse et al., 2002, *Carbohydr Res;* 337(21-23):2279-99; and Gonzalez-Outeiriño et al., 2006, *Can J Chem;* 84(4):569-579).

Thermodynamic Integration (TI). In a typical TI simulation (Kadirvelraj et al., 2008, *J Am Chem Soc;* 130:16933-16942), the electrostatic and van der Waals mutations are decoupled, with separate mixing factors as recommended for use with AMBER (Case et al., 2005, *J Comput Chem;* 26:1668-1688). At each step (X) in the perturbation an equilibration phase (100 ps) is followed by a data collection phase (500-1000 ps) with the total mutation being divided into multiple steps in λ. The change in binding energy is computed by numerical integration of $\delta V/\delta \lambda$.

Substituent remodeling. The BOMB (Biochemical and Organic Model Builder) software (Jorgensen, 2004, *Science;* 303(5665):1813-1818) will be used to construct individual structures or combinatorial libraries given a selected glycan scaffold and substituents, based on the alignment of the native glycan scaffold in the reported HA-ligand crystal structures. An extensive conformational search with implicit treatment of solvent is performed using rotamer information, which is stored for each substituent. The analogs have all principal torsion angles variable, while the host can be rigid or partially flexible. The BOMB libraries contain more than 500 drug-like substituents.

Direct ΔG calculations with the Poisson Boltzmann solvation approximation (MM-PBSA). The details of the approach taken followed closely those reported for other carbohydrate-protein complexes (Kadirvelraj et al., 2006, *PNAS;* 103(21):8149-8154). Using the MD trajectories collected from explicitly-solvated simulations of the ligand-HA complexes, the binding free energy is computed directly from the components (Equations 1 and 2, shown below):

$$\Delta G_{bind} = \Delta G_{complex} - \Delta G_{protein} - \Delta G_{ligand} \quad [1]$$

$$\Delta G = \Delta E_{MM} - T\Delta S_{MM} + \Delta G_{Desolvation} \quad [2]$$

Prior to the analyses, the water molecules are removed from the solvated trajectories and the energy contribution from solvation is then obtained through application of the Poisson-Boltzman implicit solvent approximation (Kollman et al., 2000, *Acc Chem Res;* 33(12):889-97). The vibrational, translational and rotational contributions to the entropy are derived from a normal mode analysis of the energy-minimized coordinates, while the conformational entropy is estimated from an analysis of the covariance matrix of the relevant internal coordinates (Karplus and Kushick, 1981, *Macromol;* 14:325-332). Changes in conformational entropy, arising primarily from hindered rotations, will be estimated from the motions of the backbone torsion angles in the free and bound forms of each CPS from the determinants of the covariance matrices for the torsion angles in the bound and free states (Karplus and Kushick, 1981, *Macromol;* 14:325-332).

Synthesis

General. All reactions chosen in the synthetic sequences will follow standard literature procedures and be carried out under inert conditions when required. All new compounds will be characterized by standard analytical techniques. This will include $^1$H-NMR, $^{13}$C-NMR, HRMS/Elemental analysis, IR, NMR spectra. 1H-NMR signals for new compounds will be assigned with the aid of COSY. 13C signals will be assigned with the aid of DEPT-135, HSQC and HMBC. IR spectra will be recorded using thin film on NaCl or Germanium plates. Optical rotations will be determined at the sodium D line at 20° C. All relevant TLC for monitoring reactions will be performed on aluminium sheets pre-coated with Silica Gel 60 (HF254, E. Merck) and spots visualized by UV and charring with 1:20 H2SO4-EtOH or with 1:1 KMnO4 (1% w/v solution)-NaHCO3 (5% w/v solution) or with Cerium Molybdate stain. Flash chromatography or HPLC will generally be used for compound purification before biological testing. Solvents THF, Ether, CH2Cl2 and methanol will be used as obtained from a Pure-Solv™ solvent purification system. All other solvents will be dried according to the standard accepted procedures.

Retrosynthetic Analysis. Two proposed routes to the initial target compound I are outlined in Scheme 2 (FIG. 9). 1-Deoxygalactostatin will be prepared according to literature procedure (McDonnell et al., 2004, *J Org Chem;* 69:3565-3568). Protecting group chemistry on 3 will be then investigated with a view to generate amino alcohol 9. The reaction of 9 with oxirane will give the diol 10 and its subsequent dimesylation will generate 11. The synthesis of piperidines and piperazines by double displacement of a dimesylate precursor is common in organic synthesis (Smid et al., 2005, *J Med Chem;* 48:6855-6869). The sialic acid amine 2 will be thus be prepared according to literature procedures (Rothermel et al., 1992, *Liebigs Ann Chemie;* 2:799-802; and Llinares and Roy, 1997, *Chem Commun;* 2119-2120) (3 steps from sialic acid) and the reaction of this amine 2 with the dimesylate 11a is expected to lead to 12.

Once 12 is in hand then the removal of protecting groups (de-O-acetylation, de-O-benzylation) by standard methods will give the desired compound 1. Should any difficulties arise in the piperazine ring synthesis by this approach, then other strategies will be investigated. This could involve preparation of the N-oxide 11b and study of its reaction with 2, for example. Should any difficulties be encountered alternative approaches will be investigated. For example the azide 13 will be prepared from L-arabinose. The thermally promoted azide-alkene cycloaddition will give triazoline 14. Thermal decomposition of 14 in the presence of 2 is expected to generate, via the aziridine 4, the disaccharide mimetic 15. piperazine formation by reaction of 15 with dibromoethane will lead to 12. Subsequent deprotection will give the target compound 1.

Once the synthesis has been established, biological evaluation of 1 will take place. Computational methods and the results from initial inhibition assays will be used to guide the design of second generation compounds based on the scaffold 1. The synthetic route will be modified appropriately to generate the second generation compounds.

Protein Expression, Purification and Biochemical/Biophysical Assays

Figure 10:
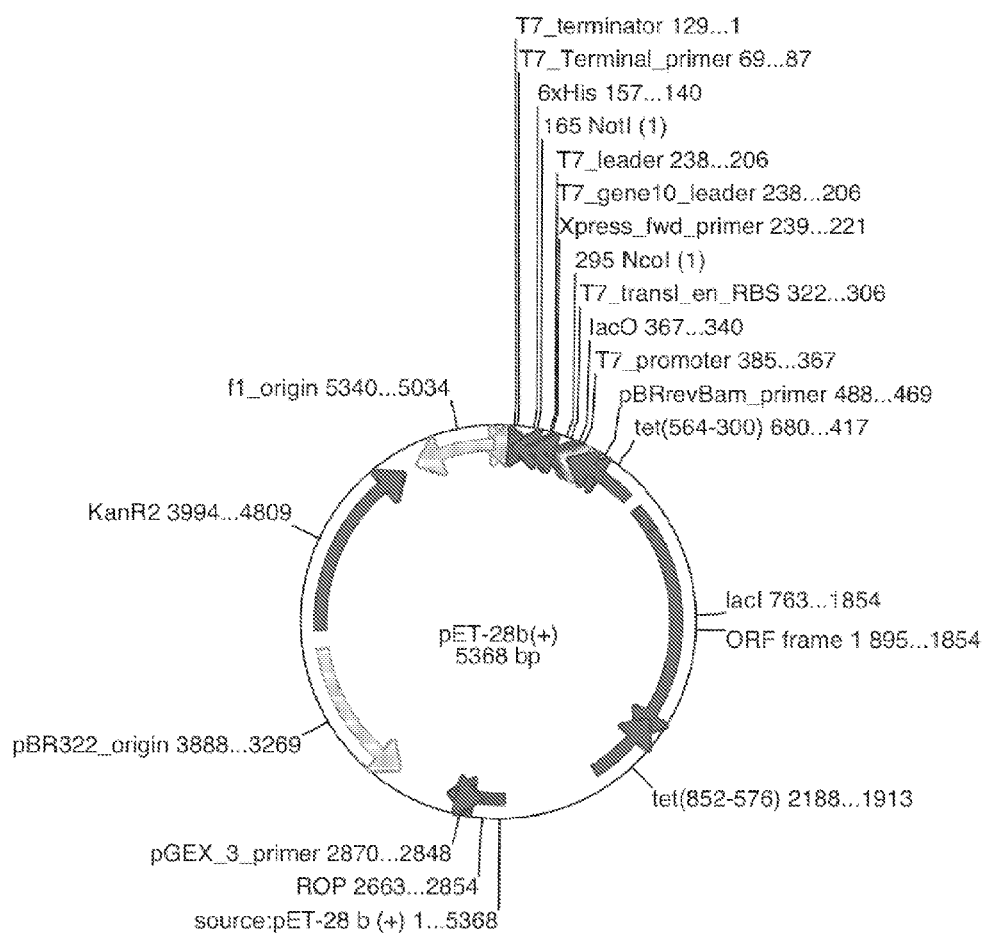
FIG. 10. The construct for the expression of truncated HA1 in the pET-28b(+) vector.

Expression of truncated H5 HA1. In order to measure monomeric binding affinities using surface Plasmon resonance (SPR) or isothermal titration calorimetry (ITC), as well as for NMR and crystallographic studies, a monomeric form of the influenza hemagglutinin ligand binding domain HA1 was generated. This monomeric form is identical to that employed in all of the computational studies, and is derived from the highly pathogenic H5 avian influenza hemagglutinin (A/Vietnam/1203/2004). The nucleotide sequence of HA1 for the H5 strain coding for residues 56-269 was cloned into the Multiple Cloning Site of the vector pET-28b(+) (Novagen) and transformed into various *E. coli* strains. T7 driven expression from the lac promoter of the plasmid after induction of the cells with IPTG leads to the production of a HA1 fragment containing the receptor binding site of the influenza A virus with a C-terminal His-tag (FIG. 10). The recombinant protein has a molecular weight of 29.74 kDa and contains two disulfide bridges in the correctly folded form.

Flow-cytometric inhibition assays for influenza binding. In a typical assay, glycan-labeled microspheres are prepared by incubating 100 µL of 5 µM biotinylated human (Neu5Acα2-6[Galβ1-4GlcNAcβ1-3]2β-SpNH-LC-LC-biotin) or avian (Neu5Acα2-3[Galβ1-4GlcNAcβ1-3]2β-SpNH-LC-LC-biotin) influenza receptor (provided by the Consortium for Functional Glycomics, Scripps) with 1×10$^7$ NeutrAvidin conjugated microspheres in PBS, 0.02% Tween for 1 hr at 4° C. on rotator, followed by washing four times with 0.5 mL PBS, 0.02% Tween, and resuspending in 50 µL PBS, 0.02% Tween. A 0.03 mg/mL solution of influenza virus or hemagglutinin is incubated with 1 µL of each of the carbohydrate-labeled microspheres in 20 µL buffer (PBS, 0.1% BSA, 0.01% Tween) for 1 h at room temperature, followed by washing one time with 0.5 mL buffer. To detect bound virus, beads are resuspended in 50 µL of a 50 nM fluoresceinated anti-influenza antibody solution for 1 h at room temperature, followed by washing one time with 0.5 mL buffer, and resuspending in 0.2 mL buffer for analysis by flow cytometry. Measurements of microsphere fluorescence are made on a Becton-Dickenson FACSCalibur (San Jose, Calif.). Sample was illuminated at 488 nm (15 mW) and forward angle light scatter (FALS), 90° light scatter (side scatter, SSC), and fluorescence signals were acquired through a 530 (±30) nm band-pass filter.

To determine $IC_{50}$ values, the multiplexed assay will be performed as described above with a range of inhibitor concentrations incubated with the influenza virus (or hemagglutinin) and bead solution. An $IC_{50}$ curve will be obtained by measuring the decrease in fluorescence intensity by flow cytometry. The concentration of inhibitor that results in half of the maximum fluorescence is the $IC_{50}$.

Binding studies by surface plasmon resonance. SPR analyses will be conducted using a Biacore 2000 apparatus with recombinant HA immobilised on the SPR chip surface. The binding analyses are typically performed at 10 and 25° C. Glycans will be obtained from the Consortium for Functional Glycomics (Scripps), and are prepared by 2-fold serial dilution to obtain an appropriate concentration range (0.01-10 µM) over a low-density immobilization surface of recombinant protein (3000 RU).

Example 4

Development of Anti-Adhesion Therapeutics

The present example described a new class of carbohydrate-based anti-influenza agents that block the initial hemagglutinin-mediated adhesion of the virus to host cells. This is a novel strategy and is complementary to vaccination or to the use of current therapeutics that inhibit the action of viral neuraminidase. The agents may be used as therapeutics for treating or preventing influenza A in both humans and livestock. In addition, other viruses and bacteria employ the same adhesion mechanism as influenza, thus the influenza blockers described herein may protect against a range of unrelated diseases.

In order to combat both human influenza A (H1N1) and also the more virulent avian influenza A (H5N1), fragments of the natural influenza receptors found on host cells (for example, α-Neu5Ac-(2,3)-Gal (avian receptor) and α-Neu5Ac-(2,6)-Gal (human receptor)) will be employed as scaffolds in the design of high-affinity glycomimetic inhibitors of influenza virus adhesion. This example will utilize computational drug design methods and carbohydrate synthesis. The potential for oligosaccharides containing terminal sialic acid (Neu5Ac) to compete with natural glycans and thus function as anti-adhesives has been demonstrated, and preliminary experimental studies are encouraging (Ilona Idanpaan-Heikkila et al., 1997, *J Infect Dis;* 176:704-712). However, considerable work needs to be done to establish approaches for converting the endogenous oligosaccharides into high affinity inhibitors that can compete effectively at low to moderate concentrations against the native glycans. In this example, fragments of the natural influenza receptors found on host cells (α-Neu5Ac-(2,3)-Gal (avian receptor) and α-Neu5Ac-(2,6)-Gal (human receptor)) will be employed as scaffolds in the design of high-affinity inhibitors of virus adhesion. Advanced computational methods will be employed to focus the number of glycomimetic synthetic targets to a select few that have the highest probability to block influenza adhesion and infection. This example will include the computationally-guided design of potential carbohydrate-based inhibitors of influenza hemagglutinin-glycan adhesion; the synthesis of optimized glycomimetic lead compounds; and the biophysical characterization of the ability of the glycomimetics to inhibit hemagglutinin binding to glycan receptors.

The outer membrane of the influenza virion is made up of a lipid bilayer that is densely studded with two viral membrane glycoproteins hemagglutinin (HA) and neuraminidase (NA). HA is a protein that binds tightly to the sugar portions of various cell-surface glycoproteins by recognizing and binding sialic acid (Neu5Ac). Human influenza viruses preferentially bind to glycans containing terminal sialic acid residues linked to galactose though α-(2,6) linkages. Whereas, avian viruses bind to sialic acid residues linked to galactose connected by α-(2-3) linkages (Wong and Yuen, 2006, *Chest;* 129(1):156-168). HA permits the influenza virus to adhere to a host cell during the initial infection. NA is a glycosidase that promotes the cleavage of sialic acid from glycoprotein saccharide chains. When the glycosidic linkage is cleaved, the viral particle is no longer tethered to the host cell and can infect other cells.

In this example, fragments of the natural influenza receptors found on host cells (Neu5Ac-(2,3)-Gal (avian receptor) and Neu5Ac-(2,6)-Gal (human receptor)) will be employed as scaffolds in the design of high-affinity inhibitors of influenza A virus adhesion. In scaffold-based drug design, an anchoring moiety provides the specificity for the receptor, and the design process consists of appending various functional groups to a core scaffold in an attempt to fill the void space in the binding site and match electrostatic surface interactions. Substituent modifications of carbohydrate scaffolds have been shown to lead to promising affinity enhancements (Sharon, 2006, *Biochim Biophys Acta;* 1760(4):527-37).

Computational methods are well suited to determining potential modifications of the basic scaffold (Jorgensen, 2004, *Science;* 303(5665):1813-1818), but they have not yet been widely applied to the design of carbohydrate-based inhibitors. A significant challenge in using carbohydrates as therapeutic agents is the low affinity of most carbohydrate-protein interactions. However, several carbohydrate leads have been converted to glycomimetic drugs (Ernst and Magnani, 2009, *Nature Rev Drug Disc;* 8:661-677) and the NA inhibitors Relenza and Tamiflu demonstrate that with appropriate chemical derivatisation molecules based on carbohydrate scaffolds can be converted into anti-influenza agents. A more significant limitation has been the lack of accurate and convenient computational tools for use in guiding glycomimetic design. The synthetic chemistry associated with carbohydrates is highly specialized, and not amenable to the creation of large combinatorial libraries of the type required by high-throughput screening, although advances continue to be made toward this goal (Werz et al., 2007, *J Am Chem Soc;* 129:2770-2771). Thus, a rational design strategy for glycomimetics is greatly needed and hence it is our plan to establish this protocol. In addition, there is considerable potential for the influenza blockers we are developing to be effective against several pathogens.

Many pathogens employ the same glycans as influenza A (sialylated galactose) as their adhesion partner, including, but not limited to, BK virus, *H. pylori*, *S. pneumoniae*, *M. pneumoniae*, *E. coli*, *N. meningitides*, and *T. gondii*.

This project will combine state-of-the-art computational methods employing the GLYCAM/AMBER force field (Kirschner et al., 2008, *J Comput Chem;* 29:622-655; Woods, R. J., C. J. Edge, M. R. Wormald, and R. A. Dwek, GLYCAM_93: A Generalized Parameter Set for Molecular Dynamics Simulations of Glycoproteins and Oligosaccharides. Application to the Structure and Dynamics of a Disaccharide Related to Oligomannose, in Complex Carbohydrates in Drug Research, K. Bock, et al., Editors. 1993, Munksgaard: Copenhagen, Denmark. p. 15-36; and Case et al., 2005, *J Comput Chem;* 26:1668-1688) with scaffold-based carbohydrate synthesis to develop compounds capable of inhibiting influenza adhesion. To develop an optimal inhibitor, an iterative procedure as shown in FIG. 8 will be employed, in which computational predictions guide synthesis, and biological assays with inactivated virus are employed to ultimately assess performance.

Experimental Design

The design process will begin with the crystal structures of H1 or H5 influenza hemagglutinin complexed with their respective receptor glycans (Gamblin et al., 2004, *Science;* 303:1838-1842; Ha et al., 2001, *Proc Natl Acad Sci USA;* 98(20):11181-6), for which extensive structural and biological affinity data are available (Stevens et al., 2006, *Nature;* 4:857-864). These structures will be subjected to refinement by molecular dynamics simulation (GLYCAM/AMBER) in the presence of explicit water at room temperature (Step 2, FIG. 8).

Computational simulations using the BOMB (Biochemical and Organic Model Builder) method (Jorgensen, 2004, *Science;* 303(5665):1813-1818) will be employed to identify pendant groups that may be added to the basic scaffold to enhance affinity (Step 3, FIG. 8). Once an optimal lead has been identified, the synthetic accessibility will be evaluated and a viable synthetic strategy will be established and carried out (Step 4, FIG. 8). The compounds will be assayed for their ability to bind to HA (Step 6, FIG. 8). The glycomimetics that have higher affinity than the native glycan receptor will be further assayed for their ability to block the adhesion of inactivated virus to glycan receptors (Step 7, FIG. 8). Sub-optimal binders that have better affinities than the native ligand will be subjected to a second level of computational discovery based on the application of thermodynamic integration (TI) calculations (Step 5, FIG. 8). TI calculations are extremely useful for estimating the effect of modest structural alterations on affinity (OH to OMe etc) (Jorgensen, 2004, *Science;* 303(5665):1813-1818). This computational protocol was developed with the goal of focusing synthetic effort on the most promising candidates (Jorgensen, 2004, *Science;* 303(5665):1813-1818). Such a strategy has not yet been applied in glycomimetic design, but appears to be highly appropriate given the challenges associated with combinatorial synthetic carbohydrate chemistry (Seeberger, 2002, *Combinatorial Chemistry;* 6(3):289-296).

There is literature precedent which suggests that approximately 85% of the total binding energy arises from interactions of the protein and only the two terminal residues (Neu5Ac-α-2-3-Gal) (Newhouse et al., 2009, *J Am Chem Soc;* 131:17430-17422). On the basis of initial structural and energetic analyses, including as shown in the previous examples, a first generation of scaffolds for the ligand have been developed which mimic the two terminal residues of the influenza receptor glycans. These target compounds are more rigid than the native receptor and therefore should benefit from less entropic penalty upon binding (FIGS. 12B and 23D). The fused ring structure of the glycomimetic scaffolds introduces rigidity into the ligands, and preorders them into the correct conformation. To ensure that naturally-occurring mutations in the protein surface are less likely to cause drug resistance, the scaffolds have the chemical alterations on the solvent side, rather than on the contact face of the protein-ligand complex (FIGS. 12B and 12D (see arrows).

Glycomimetics B and D are currently being synthesized using the approach that is illustrated in FIG. 13. The syntheses employ commercially available galactose and sialic acid starting materials. Strategic protecting group introduction and manipulation followed by glycosylation and deprotection will provide the target compounds B/D (FIG. 13). Currently the synthesis has commenced on iminosugar 4 and the sialyl donors 1 and 3 are near completion. The synthesis of the galactosyl acceptor 2 has been accomplished.

After the completion of the synthesis, the experimental confirmation of the predicted binding energy will be determine. The techniques of surface plasmon resonance (SPR) and isothermal titration calorimetry will provide direct measures of binding kinetics and thermodynamics (Gutierrez Gallego et al., 2004, *Glycobiology;* 14(5):373-386; Ford et al., 2003, *PROTEINS: Struct Funct Genet;* 53(2):229-240; Turnbull, 2004, *J Am Chem Soc;* 126:1047-1054; and Dam and Brewer, 2002, *Chem Rev;* 102:387-429) (see FIG. 8, Step 6). The recombinant HA will be immobilized on the SPR chip surface and the synthetic anti-adhesives will be assayed for their inhibitory ability of the glycan-HA interactions.

Example 5

General Methods

Synthesis: NMR spectra were recorded (25° C.) with a 500 MHz spectrometer. The frequency is 500 MHz for $^1$H NMR and 125 MHz for $^{13}$C NMR. Data are reported in the following order: chemical shift (δ) in ppm; multiplicities are indicated s (singlet), d (doublet), t (triplet), q (quartet), m (multiplet); coupling constants (J) are given in Hertz (Hz). Chemical shifts are reported relative to internal $Si(CH_3)_4$ in $CDCl_3$ (d 0.0) for $^1$H and $CDCl_3$ (d 77.0) for $^{13}$C. NMR signals were assigned with the aid of two-dimensional $^1$H, $^1$H(COSY) and/or $^1$H, $^{13}$C (HSQC) experiments. Processing of the spectra was performed with MestReNova software. Low- and high-resolution mass spectra were in positive and/or negative mode as indicated in each case. TLC was performed on aluminum sheets pre-coated with silica gel and spots visualized by UV and charring with $H_2SO_4$-EtOH (1:20), or cerium molybdate. Solvents for chromatography were technical grade. Petroleum ether 40-60° C. was used for column chromatography and thin layer chromatography (TLC). Flash chromatography was carried out with silica gel 60 (230-400 mesh). $CH_2Cl_2$, MeOH, toluene, DMF, acetonitrile and THF reaction solvents were used as obtained from a Pure Solv™ Solvent Purification System. Anhydrous pyridine was used as purchased.

Computational analysis of structural conformation: Ligand parameters and charges were determined using Antechamber in AMBER 7 with the General AMBER force field (GAFF) (D. A. Case, T. A. D., T. E. Cheatham, III, C. L. Simmerling, J. Wang, R. E. Duke, R. Luo, R. C. Walker, W. Zhang, K. M. Merz, B. Roberts, B. Wang, S. Hayik, A. Roitberg, G. Seabra, I. Kolossvai, K. F. Wong, F. Paesani, J. Vanicek, J. Liu, X. Wu, S. R. Brozell, T. Steinbrecher, H. Gohlke, Q. Cai, X. Ye, J. Wang, M.-J. Hsieh, G. Cui, D. R. Roe, D. H. Mathews, M. G. Seetin, C. Sagui, V. Babin, T. Luchko, S. Gusarov, A. Kovalenko, and P. A. Kollman: AMBER11. University of California, San Francisco, 2010). The ligands were solvated using TIP3P (Jorgensen et al., 1983, *J Chem Phys;* 79:926-935) and neutralized using counter ions. The systems were minimized, heated to K=300 and then simulated under constant pressure and temperature (NPT) conditions for 25 ns. Torsion angles which correspond to the Φ and Ψ angles in the disaccharide structure were measured at each time step.

Computational Binding Studies: Starting structures were generated from a complex of H5 avian influenza haemagglutinin bound to the avian receptor analogue (PDB ID: 1JSN). The ligands were manually modelled in. Ligand parameters and charges were determined using Antechamber in AMBER 7 with the General AMBER force field (GAFF). (D. A. Case, T. A. D., T. E. Cheatham, III, C. L. Simmerling, J. Wang, R. E. Duke, R. Luo, R. C. Walker, W. Zhang, K. M. Merz, B. Roberts, B. Wang, S. Hayik, A. Roitberg, G. Seabra, I. Kolossvai, K. F. Wong, F. Paesani, J. Vanicek, J. Liu, X. Wu, S. R. Brozell, T. Steinbrecher, H. Gohlke, Q. Cai, X. Ye, J. Wang, M.-J. Hsieh, G. Cui, D. R. Roe, D. H. Mathews, M. G. Seetin, C. Sagui, V. Babin, T. Luchko, S. Gusarov, A. Kovalenko, and P. A. Kollman: AMBER11. University of California, San Francisco, 2010). The protein ligand complexes were solvated TIP3P TIP3P (Jorgensen et al., 1983, *J Chem Phys;* 79:926-935) and neutralized using counter ions. The systems were minimized, heated to K=300 and then simulated under constant pressure and temperature (NPT) conditions for 50 ns. To obtain the $\Delta G_{binding}$ 500 uncorrelated snapshots were extracted from each trajectory for processing using the MMPBSA.py script (Miller et al., 2012, *J Chem Theory Comput;* 8:3314-3321).

Example 6

Synthesis of Selected Type I Compounds

Target glycomimetics of type I (specifically 1, Scheme 1) were synthesized from commercially available galactose and sialic acid starting materials.

Scheme 1

Sialic acid and Galactose

The preparation of the galactose aldehyde 6 was achieved in 5 steps from the known alcohol 7 (scheme 2). The alcohol 7 was prepared according to a procedure reported by Kohata et al., 1984, *Carbohydr Res;* 132:127-135).

Oxidation of the alcohol 7 was accomplished using the Dess-Martin periodinane and after 5 hours at room temperature, the ketone 8 was isolated in 94% (Scheme 2). Olefination of the ketone 8 was performed using the methyltriphenylphosphonium bromide Wittig reagent and potassium tert-butoxide to give alkene 9 in 91%. Hydroboration of the alkene 9 using 9-BBN was followed by oxidation with a basic solution containing hydrogen peroxide and led to a mixture of the corresponding 3-hydroxymethylene galactopyranoside 10 and gulopyranoside 11, which were not separable by silica gel chromatography. The two epimers were obtained in a ratio of 1.0:1.0 galacto-10: gulo-11, as determined by $^1$H NMR spectroscopy. Oxidation using the Dess-Martin periodinane provided a mixture of the corresponding aldehydes that when treated under basic conditions ($Et_3N$ in dichloromethane (1:9)), allowed for epimerization to the thermodynamically favoured equatorial aldehyde 12. The configuration at C-3 was deduced from the large $J_{2,3}$ vicinal coupling constant (11.3 Hz) for the galacto epimer 12. A vicinal coupling constant for the gulo epimer is estimated smaller (~5 Hz).

Scheme 2

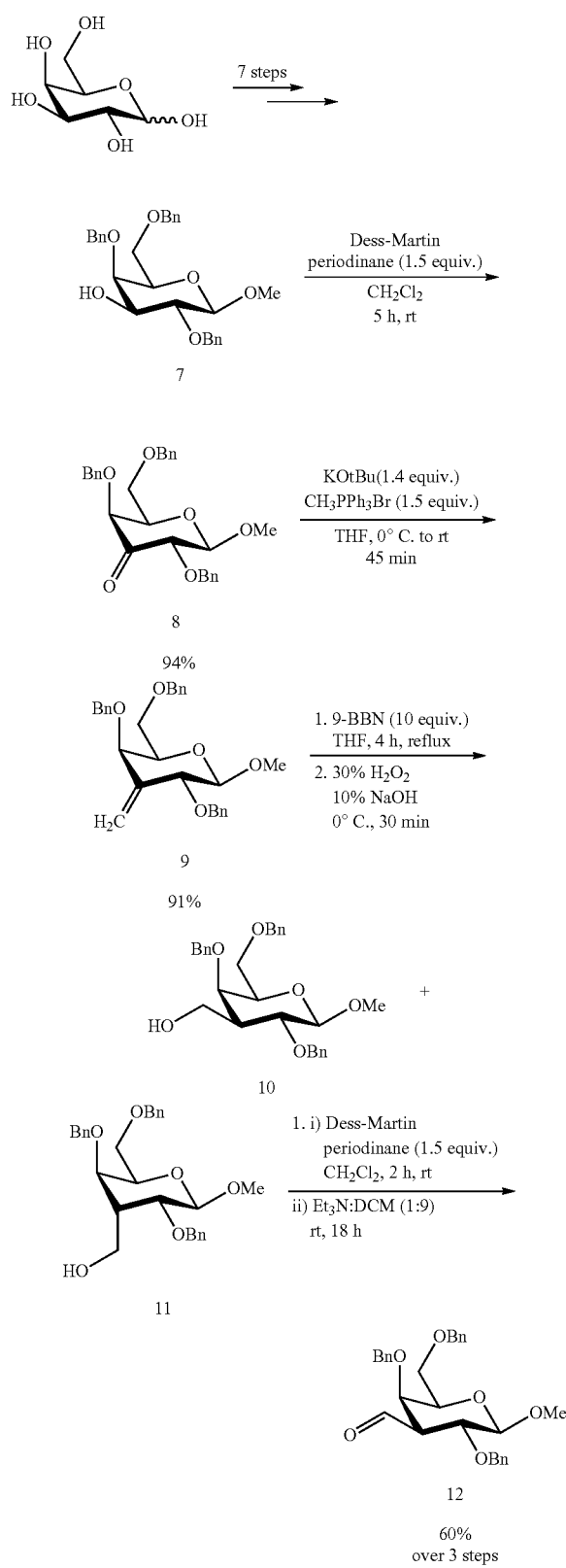

NMR for Compound 12: $^1$H NMR (500 MHz, CDCl$_3$) δ 9.50 (d, J=1.4 Hz, 1H, CHO), 7.40-7.15 (m, 15H, Ar), 4.93 (d, J=11.1 Hz, 1H, CHHPh), 4.69 (d, J=11.1 Hz, 1H, CHHPh), 4.55-4.40 (m, 4H, 2×CH$_2$Ph), 4.34 (d, J=7.6 Hz, 1H, H-1), 4.17 (d, J=2.5 Hz, 1H, H-4), 4.05 (dd, J=11.3, 7.6 Hz, 1H, H-2), 3.70-3.59 (m, 3H, H-5, H-6ab), 3.57 (s, 3H, OCH$_3$), 2.46 (ddd, J=11.3, 3.0, 1.8 Hz, 1H, H-3). $^{13}$C NMR (126 MHz, CDCl$_3$) δ 201.40 (CHO), 138.16, 137.64, 137.54, 128.48, 128.39, 128.25, 128.19, 128.02, 128.01, 127.91, 127.90, 127.87, 127.80 (Ar), 105.99 (C-1), 75.89 (C-5), 74.80 (CH$_2$Ph), 74.49 (CH$_2$Ph), 74.03 (C-4), 73.57 (CH$_2$Ph), 73.21 (C-2), 68.08 (C-6), 57.13 (C-3), 56.77 (OCH$_3$).

The preparations of the sialic acid building blocks 4 and 5 (Scheme 3) were accomplished using the literature procedures reported by Malapelle et al. (Malapelle et al., 2007, *Eur J Org Chem;* 19:3145-3157) and Okamoto et al. (Okamoto et al., 2008, *J Org Chem;* 73:3460-3466) respectively.

Scheme 3

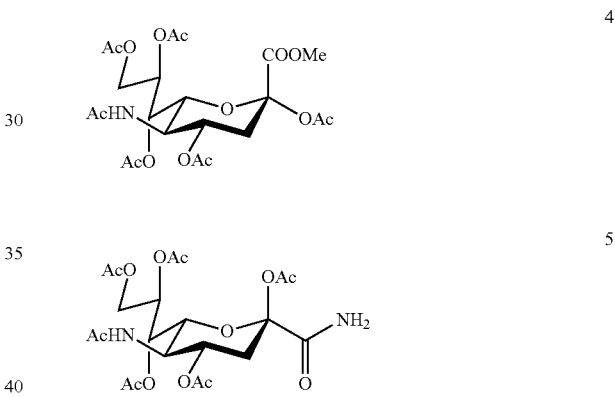

C-glycosylation between 4 and 12 using samarium diiodide was patterned after a literature method (Bazin et al., 1999, *J Org Chem;* 64:7254-7259) in which the C-glycosylation of similar monosaccharides was reported. Under these conditions, a 1:1 ratio of acetate 4 and aldehyde 12 gave 31% of the C-disaccharide 13 in a 1:1 ratio of R:S isomers (as determined by $^1$HNMR) which were not separable by silica gel chromatography. The yield of 13 was increased to 49% when 2.0 equivalents of the acetate 4 were used. The ratio of R:S isomer was left unchanged (1:1, determined by $^1$HNMR).

NMR of Compound 13: $^1$H NMR (500 MHz, CDCl$_3$) δ 7.41-7.27 (m, 30H, Ar), 5.43 (m, 2H, 2×H-8'), 5.29 (dd, J=9.2, 1.8 Hz, 1H, H-7'), 5.22 (dd, J=9.2, 2.1 Hz, 1H, H-7'), 5.15 (d, J=10.2 Hz, 1H, NH), 5.09-5.02 (m, 2H, NH, CHHPh), 4.94 (d, J=11.2 Hz, 1H, CHHPh), 4.84-4.72 (m, 3H, CHHPh, 2×H-4'), 4.66 (d, J=11.7 Hz, 1H, CHHPh), 4.63-4.43 (m, 10H, H-1, 9×CHHPh), 4.38 (d, J=7.4 Hz, 1H, H-1), 4.31 (d, J=2.4 Hz, 1H, H-4), 4.30-3.60 (m, 21H, 2×H-2, 2×H-5, 4×H-6, 2×H$_{bridge}$, 2×H-5', 2×H-6', 4×H-9', OCH$_3$), 3.59-3.53 (m, 9H, 3×OCH$_3$), 3.15 (d, J=2.7 Hz, 1H, H-4), 2.52 (dd, J=13.2, 4.6 Hz, 1H, H-3'), 2.28-2.20 (m, 3H, H-3, 2×H-3'), 2.17 (2s, 6H, 2×Ac), 2.05-1.97 (m, 16H, H-3, 5×Ac), 1.89 (s, 3H, Ac), 1.84, 1.83 (2s, 6H, 2×Ac), 1.81-1.73 (m, 1H, H-3'). $^{13}$C NMR (126 MHz, CDCl$_3$) δ 171.36, 171.04, 171.00, 170.62, 170.57, 170.18, 169.89, 169.82 (C=O), 138.71, 138.67, 138.32, 137.55, 137.47, 128.43, 128.40, 128.36, 128.33, 128.32, 128.30, 128.22, 128.19, 128.10, 127.91, 127.87, 127.83, 127.71, 127.70, 127.63, 127.58, 127.48, 127.42, 127.41 (Ar), 106.59, 106.12 (C-1), 83.63, 82.44 (C-2'), 76.75, 76.54, 76.02, 75.96, 74.83, 74.75, 74.37, 73.55, 73.50, 73.36, 72.85, 72.37 (C-2, C-4, C-5, CHOH, C-5', C-6', 6×CH$_2$Ph), 70.21, 69.97 (C-4'), 68.31, 68.28, 68.18 (C-6, C-8'), 67.20, 67.06 (C-7'), 62.21 (C-9'), 56.95, 56.76, 52.41, 52.24 (OCH$_3$), 49.52 (C-5'), 42.94, 42.83 (C-3), 35.99 (C-3'), 23.20, 21.32, 21.14, 20.90, 20.87, 20.81, 20.73, 20.63 (COCH$_3$).

C-glycosylation between 5 and 12 was carried out under the same conditions as for the synthesis of compound 13. Reaction of the 3-formyl galactoside 12 with 2.0 equivalents of the acetate 5 in the presence of freshly prepared samarium (II) iodide afforded the corresponding C-disaccharides 15(R/S) in approximately 27%. This approach is disadvantaged by the low yield obtained and by difficulty in the purification of the C-disaccharide 15.

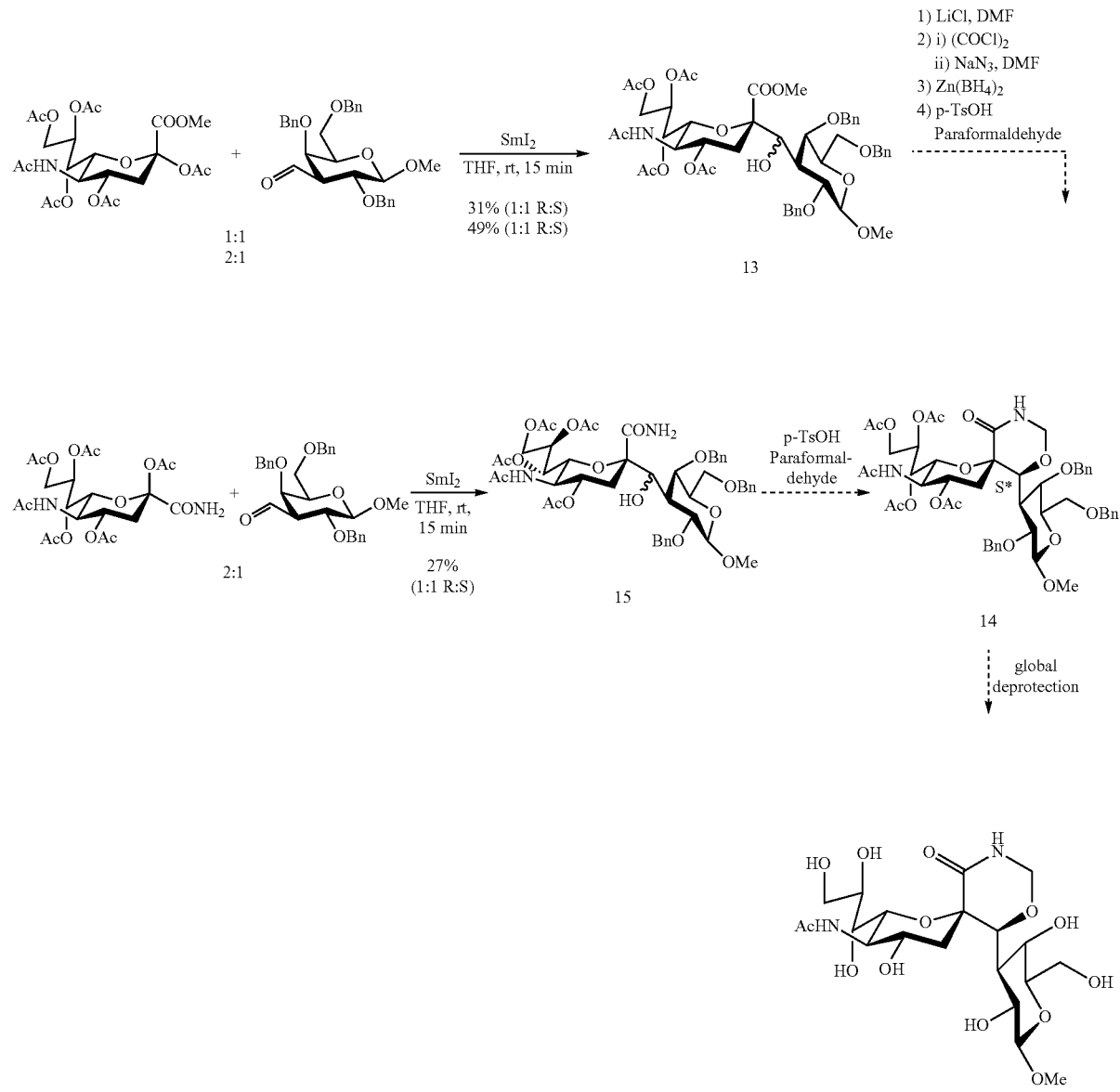

Scheme 4

The completion of the scaffold 14 will involve the lactam ring formation, resolution of the R- and S-isomers and deprotection. The proposed synthetic route is detailed in Scheme 4.

Alternatively the target glycomimetics of type I (specifically compound 16, Scheme 5) were synthesized from commercially available galactose and sialic acid starting materials via the synthetic strategy shown below.

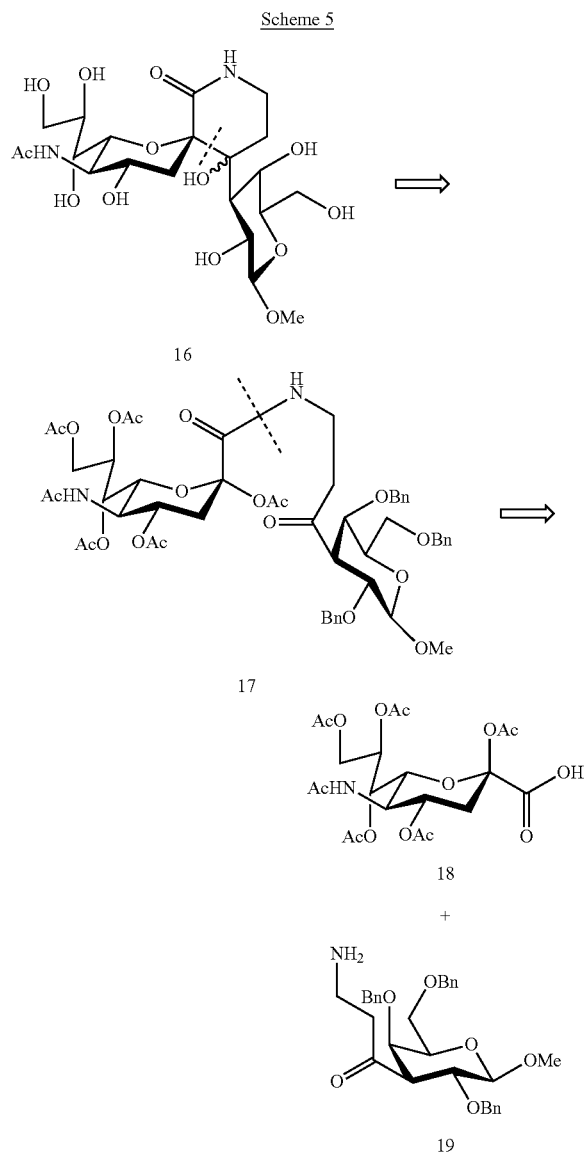

Scheme 5

The reaction of the intermediate 12 with vinyl magnesium bromide gave a mixture of the corresponding vinyl alcohols which were subjected to Dess-Martin oxidation to give the α,β-unsaturated ketone 20 in 73% over 2 steps (Scheme 6). The vinyl ketone 20 was converted to the azide via an aza-Michael reaction and the Staudinger reaction afforded the amine 19 in 67% yield over 2 steps.

NMR of Compound 19: $^1$H NMR (500 MHz, CDCl$_3$) δ 7.58-7.06 (m, 15H, Ar), 4.90 (d, J=10.8 Hz, 1H, CHHPh), 4.63 (dd, J=10.0, 6.4 Hz, 1H, CHHPh), 4.58-4.35 (m, 4H, 4×CHHPh), 4.31 (d, J=7.7 Hz, 1H, H-1), 3.75-3.57 (m, 3H, H-5, H-6ab), 3.55 (s, 3H, OCH3), 2.71 (m, 3H, H-3, CH$_2$NH$_2$), 1.99-1.83 (m, 1H, CH$_2$C=O). $^{13}$C NMR (126 MHz, CDCl$_3$) δ 208.67 (C=O), 137.61, 128.51, 128.50, 128.48, 128.33, 128.31, 128.28, 128.25, 128.22, 128.00, 127.97, 127.93, 127.91, 127.80, 127.54, 127.52 (Ar), 106.15 (C-1), 76.09 (C-5), 74.76, 74.40, 74.30, 74.28, 73.62 (C-2, C-4, 3×CH$_2$Ph), 68.22 (C-6), 57.98, 56.73 (C-3, OCH$_3$), 40.41 (CH$_2$NH$_2$), 24.95 (CH$_2$C=O).

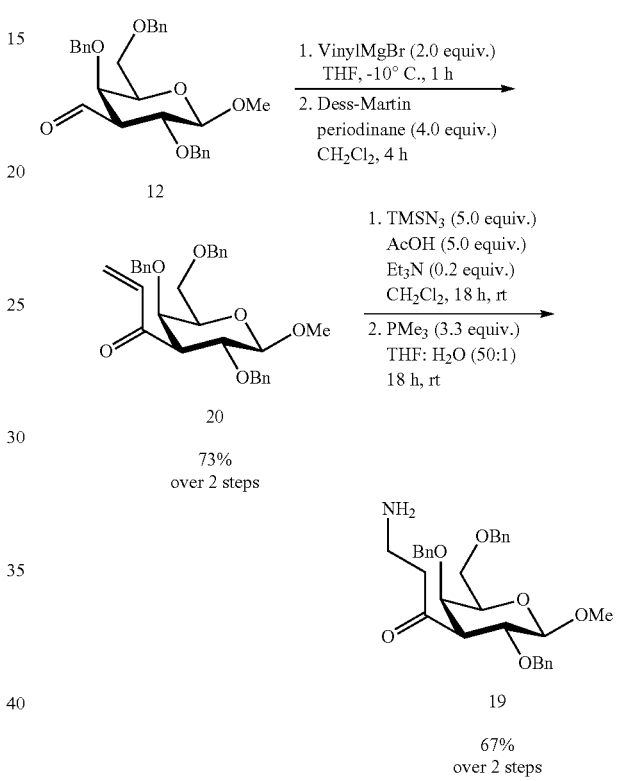

Scheme 6

The acid 18 was prepared according to the literature procedures reported by Paulsen et al. (Paulsen et al., 1984, Carbohydr Res; 125:47-64). The acid 18 was converted to its corresponding acid chloride and was reacted with the amine 19 in a one-pot process to afford the tethered disaccharide 17 in 50% (Scheme 7).

NMR for compound 17: $^1$H NMR (500 MHz, CDCl$_3$) δ 7.41-7.14 (m, 15H, Ar), 5.47-5.16 (m, 3H, NH, H-4'H-7'), 5.08 (ddd, J=6.1, 2.7 Hz, 1H, H-8'), 4.91 (d, J=10.8 Hz, 1H, CHHPh), 4.63 (d, J=10.8 Hz, 1H, CHHPh), 4.57-4.35 (m, 5H, H-9a', 2×CH$_2$Ph), 4.30 (d, J=7.6 Hz, 1H, H-1), 4.21-3.91 (m, 5H, H-2, H-4, H-5', H-6', H-9b'), 3.80-3.67 (m, 1H, H-5), 3.68-3.56 (m, 2H, H-6ab), 3.54 (s, 3H, OCH$_3$), 3.37 (ddt, J=36.3, 13.8, 6.9 Hz, 2H, CH$_2$), 2.83-2.59 (m, 3H, H-3, CH$_2$), 2.52 (dd, J=13.6, 5.0 Hz, 1H, H-3a'), 2.14, 2.04, 2.03, 2.00, 1.99, 1.89 (5s, 15H, 5×Ac), 1.73-1.64 (m, 1H, H-3b'). $^{13}$C NMR (126 MHz, CDCl$_3$) δ 207.22 (C=O), 170.92, 170.56, 170.25, 170.06, 170.04, 167.81, 166.70 (COCH$_3$), 138.54, 137.61, 132.11, 132.03, 128.54, 128.46, 128.44, 128.29, 128.28, 128.22, 128.01, 127.95, 127.89, 127.80, 127.53 (Ar), 106.14 (C-1), 76.10 (C-5), 75.29, 74.60, 74.54, 74.20, 73.59, 72.63 (C-2, C-4, C-6', 3×CH$_2$Ph), 70.65 (C-8'), 68.29, 68.14, 67.78 (C-6, C-4', C-7'), 61.73 (C-9'), 58.06

(C-3), 56.70 (OCH$_3$), 49.78 (C-5'), 40.57 (CH$_2$), 37.02 (C-3'), 34.51 (CH$_2$), 23.18, 20.91, 20.81, 20.79, 20.73 (COCH$_3$).

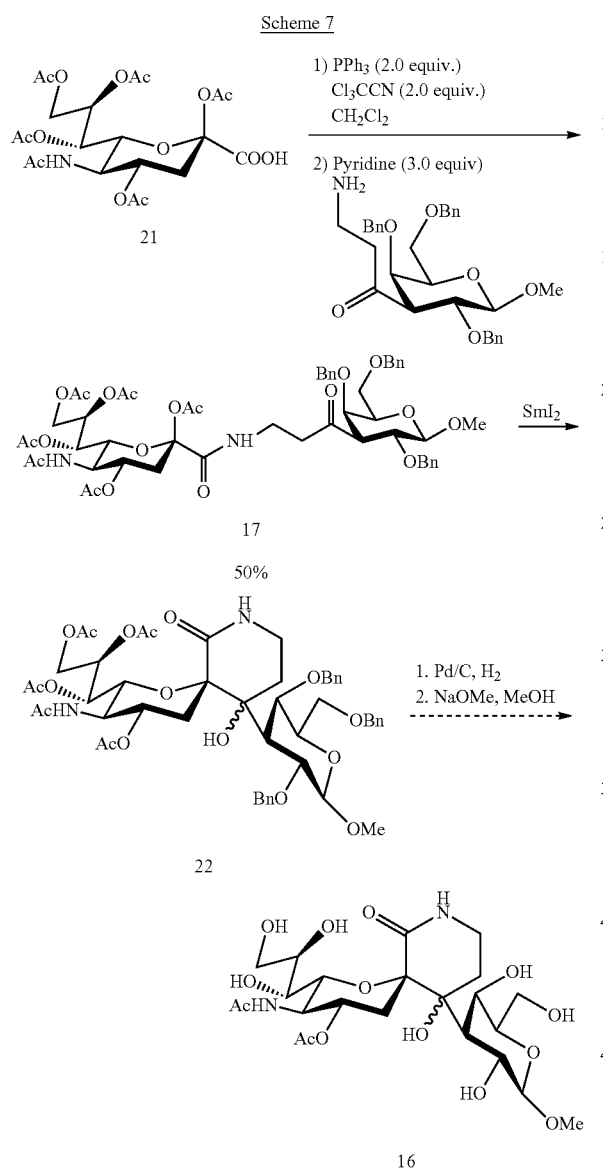

Scheme 7

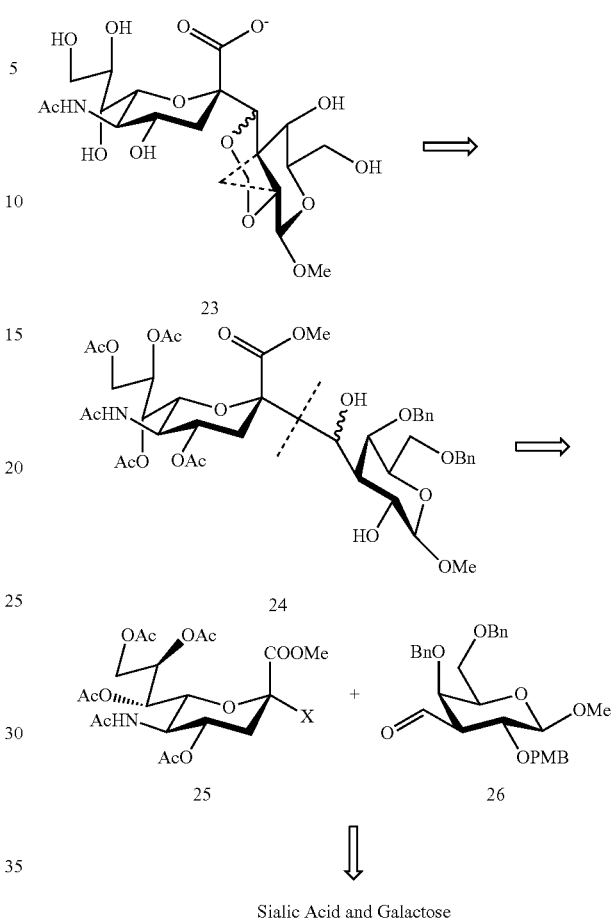

Scheme 8

Treatment of the compound 17 with freshly prepared samarium (II) iodide will give the corresponding C-disaccharide mixture 22. The mixture of isomers will then be subjected to global deprotection which will involve hydrogenolysis and Zemplén deacetylation to give the scaffold 16 as both the R and S isomers (Scheme 7).

Example 7

Synthesis of Type III Compounds

Target glycomimetics of type III (specifically 23, Scheme 8) were synthesized from commercially available galactose and sialic acid starting materials.

The acetonide 27 was prepared according to the literature procedures as reported by Busse et al. (Busse et al., 2007, *J Carbohydr Chem*; 26:159-194)

According to Scheme 9, the acetonide 27 was treated with p-methoxybenzyl chloride, tetrabutylammonium iodide and sodium hydride in DMF to give the fully protected galactoside 28 in 82% yield. Removal of the isopropylidene was accomplished using acidic conditions and the resulting crude diol was treated with sodium hydride and benzyl bromide to give the galactoside 29 in 95% yield over two steps. Removal of the allyl ether protecting group at O-3 was accomplished using palladium chloride in a mixture of toluene and methanol and after 2 hours at room temperature 87% yield of the alcohol 30 was obtained along with 10% yield of the side product 31. It was found that in order to minimize the formation of the side product 31 a basic work-up procedure was required. Thus, the reaction mixture was filtered over a pad of celite and the filtrate was neutralized (approximately pH 7, as indicated with pH paper) with triethylamine (0.3 equivalents). The alcohol 30 was then oxidized using the Dess-Martin periodinane and the ketone 32 was obtained in 90% yield. The Wittig olefination easily provided the alkene 33 in a near quantitative yield from the ketone 32. With the alkene 33 in hand, the hydroboration-oxidation reaction was performed. The hydroboration-oxidation reaction led to the expected anti-Markovnikov products, 3-hydroxymethylene galacto- and gulopyranoside (34), with the hydroxyl group adding to the less-substituted carbon. However, in this case, approximately the same amount (44%) of the Markovnikov product 35 was also isolated. Dess-Martin oxidation of the alcohol mixture 34 gave the corresponding aldehydes, which under basic conditions selectively gave the thermodynamic 3-formyl galactopyranoside 26.

NMR of compound 26: $^1$H NMR (500 MHz, CDCl$_3$) δ 9.47 (d, J=1.7 Hz, 1H, CHO), 7.52-7.05 (m, 12H, Ar), 6.98-6.75 (m, 2H, Ar), 4.85 (d, J=10.8 Hz, 1H, CH$_2$Ph), 4.64 (d, J=10.8 Hz, 1H, CH$_2$Ph), 4.57-4.41 (m, 4H, 2×CH$_2$Ph), 4.34 (d, J=7.6 Hz, 1H, H-1), 4.16 (d, J=3.3 Hz, 1H, H-4), (dd, J=11.3, 7.6 Hz, 1H, H-2), 3.80 (s, 3H, OCH$_3$), 3.71-3.49 (m, 6H, H-5, H-6ab, OCH$_3$), 2.44 (ddd, J=11.4, 3.0, 1.8 Hz, 1H, H-3). $^{13}$C NMR (126 MHz, CDCl$_3$) δ 201.52 (C=O), 159.31, 137.62, 137.54, 130.26, 129.91, 129.57, 128.45, 128.33, 128.21, 127.97, 127.86, 127.84, 127.76, 127.68, 113.80, 113.79 (Ar), 106.02 (C-1), 75.86 (C-5), 74.76, 74.05, 74.02, 73.54, 72.66 (C-2, C-4, 3×CH$_2$Ph), 68.07 (C-6), 57.07 (C-3), 56.74, 55.23 (OCH$_3$).

The anomeric 2-thiopyridyl derivative of sialic acid 36 (Scheme 10) was prepared following literature procedures reported by Malapelle et al. (Malapelle et al., 2009, *Heterocycles;* 77:1417-1424).

The treatment of a solution of sulfide 36 and aldehyde 26 in THF at room temperature with a freshly prepared solution of SmI$_2$ in THF led to the formation of the C-glycoside 37 in 15% yield (Scheme 10). With the C-disaccharide in hand, removal of the p-methoxybenzyl protecting group will be carried out with DDQ to give the alcohol 24. Ring formation can then be attempted using dibromomethane under acidic conditions to give the tricyclic compound 39. The removal of the benzyl ether protecting groups using hydrogenolysis will then be carried out followed by Zemplén deacetylation to furnish the target compound 23 (Scheme 10).

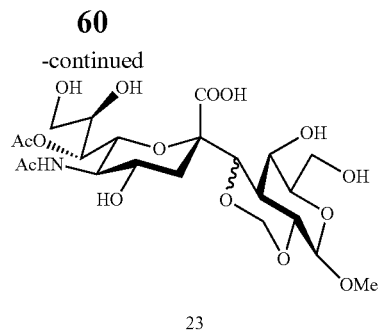

23

Scheme 10

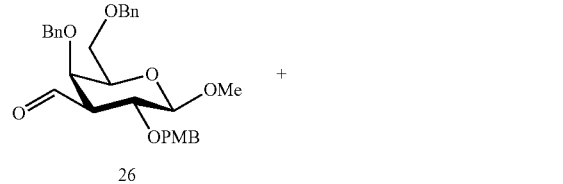

26

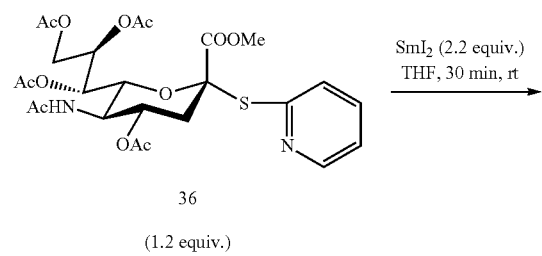

36 (1.2 equiv.)

SmI$_2$ (2.2 equiv.) THF, 30 min, rt

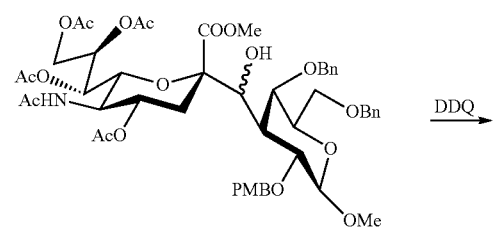

37
15%

DDQ

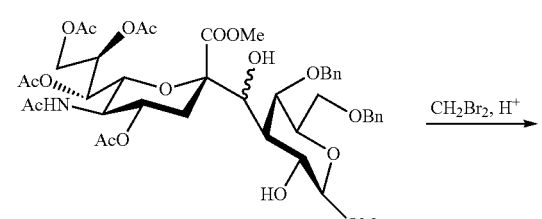

24

CH$_2$Br$_2$, H$^+$

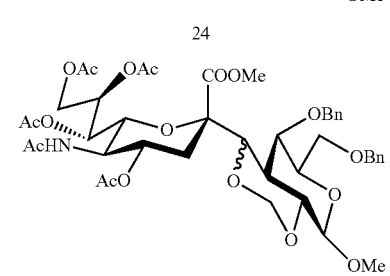

39

1. Pd/C, H2
2. LiOH

Example 8

Synthesis of Type IV Compounds

Target glycomimetics of type IV (specifically 40, Scheme 11) were synthesized from commercially available galactose and sialic acid starting materials.

Scheme 11

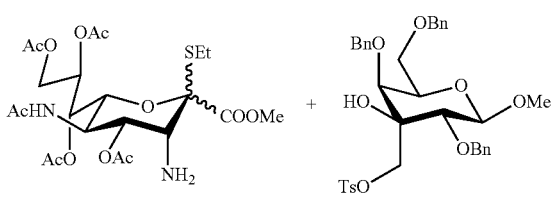

The C-3 azido derivative of sialic acid 42 (Scheme 12) was prepared following literature procedures reported by Paulsen et al. (Paulsen et al., 1991, *Liebigs Ann Chem;* 487-495).

Scheme 12

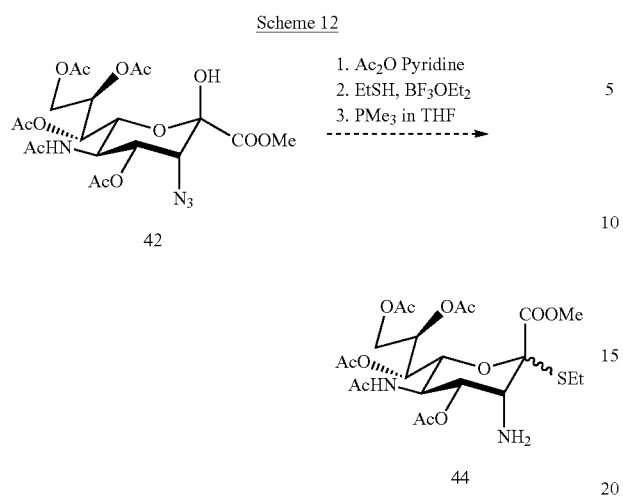

With the azido derivative 42 in hand, acetylation of the anomeric position will be accomplished using acetic anhydride and pyridine (Scheme 12). The thioethyl glycoside will be furnished by activation of the anomeric acetate with $BF_3OEt_2$ and then displacement using ethanthiol. The Staudinger reduction will then be used to convert the C-3 azide to the amine 44 (Scheme 12).

Intermediate 9 was subjected to the Upjohn dihydroxylation using catalytic osmium tetroxide and a stoichiometric amount of NMO as an oxidant to give an inseparable mixture of the 1,2 diols 45 (Scheme 13). Tosylation of the primary alcohols should allow for the separation of the two isomers. With the amine 44 and the tosylate 43 in hand, tethering of the glycosides will be carried out, followed directly by glycosylation to give the tricyclic compound 46. The target scaffold 42 will be obtained after global deprotection, which will involve hydrogenolysis and Zemplén deacetylation (Scheme 13).

NMR of compound 45: $^1$HNMR (500 MHz, $CDCl_3$) δ 7.48-7.17 (m, 15H), 4.90 (d, J=11.1 Hz, 1H, CHHPh), 4.85 (d, J=11.3 Hz, 1H, CHHPh), 4.75-4.60 (m, 3H, H-1, 5×CHHPh), 4.59-4.44 (m, 5H, 3×CHHPh), 4.40 (d, J=7.9 Hz, 1H, H-1), 4.19 (ddd, J=7.5, 6.3, 1.2 Hz, 1H, H-3), 4.02 (d, J=11.9 Hz, 1H, CHHOH), 3.79 (ddd, J=7.2, 5.9, 1.3 Hz, 1H, H-3), 3.73 (d, J=1.3 Hz, 2H, 2×H-4), 3.67-3.58 (m, 8H, H-2, 2×H-5, 2×H-6ab, CHHOH), 3.56 (s, 3H, $OCH_3$), 3.53 (s, 4H, CHHOH, $OCH_3$), 3.50-3.46 (m, 2H, CHHOH).

Scheme 13

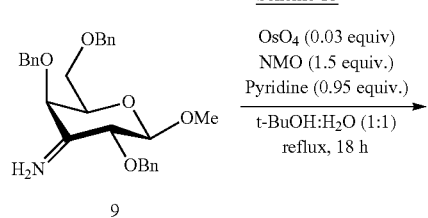

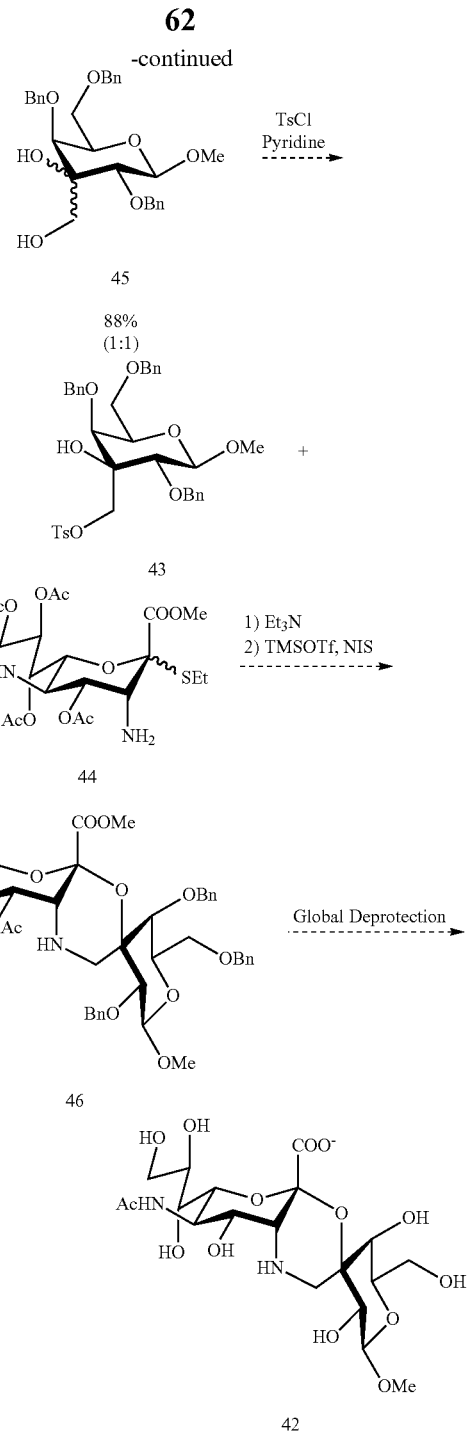

Example 9

Comparison of Scaffold Structures to Neu5Ac-α-(2-3)-Gal Structure

The conformation of the scaffolds was studied by performing molecular dynamics simulations in solution for 25 ns. In general oligosaccharide conformations are governed by the glycosidic dihedral/torsion angles which are represented by phi and psi (Φ and Ψ, respectively). The torsion angles for the scaffolds were measured and compared with the relevant torsion angles from the human influenza receptor in complex with haemagglutinin measured from X-ray crystal structure. The average angles for selected scaffolds (1, 47-52, Scheme 14) are summarized in Table 5. The average angles of Φ and Ψ for Neu5Ac-α-(2-3)-Gal were calculated using the following structures from the PDB: 1RVX, 1RV0 (Gamblin et al., 2004, *Science;* 303:1838-1842), 1JSN (Ha et al., 2001, *Proc Natl Acad Sci USA;* 98:11181-11186), 3HTP (Lin et al., 2009, *Virology;* 392: 73-81), and 1MQM (Ha et al., 2003, *Virology;* 309:209-218).

Scheme 14

TYPE I
1: A=NH, B=O
47: A=NH, B=CH$_2$
48: A=O, B=CH$_2$
49: A=O, B=O

TYPE III
50: A=O
51: A=CH$_2$

TYPE IV
52

The molecular dynamics study of the scaffold's torsion angles shows that the phi angle for the scaffolds is generally in good agreement with that of the natural ligand, sialyl galactose. While there is more variation in the psi torsion angle amongst the scaffolds, they also compare well to the conformation of the natural ligand bound in various crystal structures of HA subtypes. Based on these results we predict that each of these structures could bind to influenza haemagglutinin. This prediction may also be made for the other pathogens which bind Neu5Ac-α-(2-3)-Gal.

TABLE 5

| Compound | Phi Φ | Psi Ψ |
|---|---|---|
| 1 | 172.3 | 296.3 |
| 47 | 184.1 | 348.0 |
| 48 | 182.1 | 342.5 |
| 51 | 174.5 | 311.9 |
| 52 | 176.5 | 291.9 |
| Neu5Ac-α-(2-3)-Gal (PDB average) | 188.06 | 328.38 |

Example 10

Estimation of Protein-Ligand Binding Energy

MM-PBSA is a method which uses molecular mechanic energies (MM), a continuum Poisson-Boltzmann (PB) solvent model and a solvent accessible surface area (SA) dependant non polar solvation term. It may also include an entropy contribution however, this can be omitted if the study focuses on a series of compounds with similar structures and only the relative order of binding affinity is of interest. A summary of the results are presented in Table 6.

$$\Delta G_{bind} = \Delta G_{complex} - \Delta G_{protein} - \Delta G_{ligand}$$

The free energy of each reactant is calculated by summing four terms:

$$\Delta G = \langle \Delta_{EMM} \rangle + \langle \Delta G_{Solv} \rangle + \langle \Delta G_{np} \rangle - T \langle \Delta_{SMM} \rangle$$

$\Delta G_{solv}$=Polar solvation energy of molecule (estimated using Poisson-Boltzmann);
$\Delta G_{np}$=Non-polar solvation energy (estimated using the solvent accessible surface area of the molecule)
T=Temperature
$\Delta_{SMM}$=Entropy of the molecule
$\Delta_{EMM}$=is the molecular mechanics energy of the molecule, i.e. sum of the internal energy of the molecule, electrostatics and van der Waals interaction $$\Delta_{EMM} = E_{int} + E_{es} + E_{vdW}$$

TABLE 6

| Scaffold | ΔG$_{binding}$ | Std. Dev. | Std. Err. Mean | ΔG relative to Disaccharide |
|---|---|---|---|---|
| 1 | −34.0322 | 4.3054 | 0.1925 | 7.2509 |
| 47 | −34.3304 | 4.9827 | 0.2228 | 6.9527 |
| 48 | −31.388 | 5.1226 | 0.2488 | 9.8951 |
| 49 | −30.7307 | 4.949 | 0.2213 | 10.5524 |
| 50 | −41.0297 | 6.9933 | 0.3128 | 0.2534 |
| 51 | −38.0675 | 6.6173 | 0.2959 | 3.2156 |
| 52 | −43.0028 | 5.8354 | 0.261 | −1.7197 |
| Neu5Ac-α-(2-3)-Gal | −41.2831 | 6.4715 | 0.2894 | 0 |

*All results in kcal/mol

The results obtained from the computational binding studies are shown in Table 6. From these studies all of the scaffolds are predicted to bind to the haemagglutinin protein (Table 6, ΔG$_{binding}$). The standard deviation of the total binding energy is approximately 5 kcal/mol for the scaffolds and the natural ligand (Table 6, Std Dev). Taking into consideration the standard deviation, the total binding energies of all of the scaffolds are comparable and it can be assumed that all of the scaffolds should bind to haemagglutinin competitively or superior to the natural ligand (Neu5Ac-α-(2-3)-Gal). To clearly illustrate which scaffolds can be predicted to bind preferentially over the natural ligand, the relative binding energies were calculated (Table 6, ΔG relative to Disaccharide). Scaffolds of the Type III (50 and 51) and IV (52) are predicted to bind better than or competitively to haemagglutinin relative to the natural disaccharide. Scaffolds of the Type I (1, 47-49) are predicted to bind competitively to haemagglutinin relative to the natural disaccharide. Although the compounds of Type I are predicted to be less effective for their anti-adhesion properties of haemagglutinin, these scaffolds are predicted to be useful for their anti-adhesion properties with other pathogens (for example: *Clostridium botulinum*).

Example 11

Synthesis of Type V Compounds

Target glycomimetics of type V (specifically 53, Scheme 15) were synthesized from commercially available galactose and sialic acid starting materials.

Scheme 15

53

54

55

⇓ sialic acid and galactose starting materials

Example 12

Biophysical Characterization

A variety of methods will be used for the biophysical characterization of the glycomimetic compounds described herein. For example, predicted binding energy may be determined. The techniques of surface plasmon resonance (SPR) and isothermal titration calorimetry will provide direct measures of binding kinetics and thermodynamics (Gutierrez Gallego et al., 2004, *Glycobiology;* 14(5):373-386; Ford et al., 2003, *PROTEINS: Struct Funct Genet;* 53(2):229-240; Turnbull, 2004, *J Am Chem Soc;* 126:1047-1054; and Dam and Brewer, 2002, *Chem Rev;* 102:387-429) (see FIG. 8, Step 6). The recombinant HA may be immobilized on the SPR chip surface and the synthetic anti-adhesives will be assayed for their inhibitory ability of the glycan-HA interactions.

Biophysical characterization may include a determination of the ability of a glycomimetic to inhibit hemagglutinin binding to glycan receptors, or the binding of another target carbohydrate ligand to its glycan receptor. For example, and of the methods described in WO 2012/118928 or US 2011/0257032 (which are herein incorporated by reference) may be used.

Example 13

Characterization of Synthetic Glycomimetics

Upon the completion of the synthesis of a glycomimetic compound with predicted desirable ligand binding characteristics using computational methods and molecular simulations methods described in the previous example, pathogen-glycan binding inhibition ability will be confirmed using various experimental binding assays.

For example, the inhibitory ability of the glycan-protein interactions will be assessed by techniques including, but not limited to, multiplexed microsphere-based assay, surface plasmon resonance (SPR), and competitive ELISA.

In order to facilitate the characterization of influenza virus binding, a multiplexed microsphere-based assay for simultaneous antibody-based strain typing and sub-typing as well as characterization of carbohydrate receptor binding preference will be used. See, for example, Yan et al., 2005, *Analyt Chem;* 77:7673-7678.

For strain typing and sub-typing, distinct optically-encoded microspheres were functionalized with antibodies specific for influenza virus A sub-types H1N1 and H5N1. For receptor preference analysis, microspheres were functionalized with avian 2,3 influenza receptors or human 2,6 influenza receptors. Microsphere-bound virus was detected using fluorescence-labeled anti-influenza virus antibodies and measured using flow cytometry. FIG. 6 illustrates that the assay detects the binding of inactivated influenza virus to microspheres bearing carbohydrates with the appropriate receptor specificity. In addition the assay can identify the viral sub-type, as demonstrated with virus strains that have been previously characterized by other methods including hemagglutination and glycan microarray (FIG. 6).

The human influenza strain A/New Caledonia/20/99 (H1N1) displayed its known preference for the human 2,6 receptor over the avian 2,3 receptor. The HPAI A/Vietnam/1203/04 (H5N1) demonstrated a clear preference for the 2,3 receptor. These assays work equally well, in fact slightly better, with recombinant HA protein (Yan, et al., 2005, *Analyt Chem;* 77:7673-7678). Because a minimal amount of reagent is required, this assay will be amenable to high throughput screening of HA's for receptor specificity, as well as high throughput screening of inhibitors of HA.

Flow-cytometric inhibition assays will be used for assessing pathogen binding. In a typical assay, glycan-labeled microspheres are prepared by incubating 100 μL of 5 μM biotinylated human (Neu5Acα2-6[Galβ1-4GlcNAcβ1-3]$_2$β-SpNH-LC-LC-biotin) or avian (Neu5Acα2-3[Galβ1-4GlcNAcβ1-3]$_2$β-SpNH-LC-LC-biotin) influenza receptors (or any other biotinylated-glycan) with $1\times10^7$ NeutrAvidin conjugated microspheres in PBS, 0.02% Tween for 1 hr at 4° C. on rotator, followed by washing four times with 0.5 mL PBS, 0.02% Tween, and resuspending in 50 μL PBS, 0.02% Tween. A 0.03 mg/mL solution of influenza virus or haemagglutinin is incubated with 1 μL of each of the carbohydrate-labeled microspheres in 20 μL buffer (PBS, 0.1% BSA, 0.01% Tween) for 1 h at room temperature, followed by washing one time with 0.5 mL buffer. To detect bound virus, beads are resuspended in 50 μL of a 50 nM fluoresscinated anti-influenza (or anti-HA) antibody solution for 1 h at room temperature, followed by washing one time with 0.5 mL buffer, and resuspending in 0.2 mL buffer for analysis by flow cytometry. The virus or HA protein may also be directly fluoresceinated, for detection purposes. Measurements of microsphere fluorescence will be made on a Becton-Dickenson FACSCalibur (or similar instrument). Samples are illuminated at 488 nm (15 mW) and forward angle light scatter (FALS), 90° light scatter (side scatter, SSC), and fluorescence signals acquired through a 530 (±30) nm bandpass filter.

To determine $IC_{50}$ values, the multiplexed assay will be performed as described above with a range of inhibitor concentrations incubated with the influenza virus (or haemagglutinin) and bead solution. An $IC_{50}$ curve will be obtained by measuring the decrease in fluorescence intensity by flow cytometry. The concentration of inhibitor that results in half of the maximum fluorescence is the $IC_{50}$.

Binding studies by surface plasmon resonance will be used. SPR analyses will be conducted using a suitable apparatus (for example, Biacore or Reichert) with the recombinant or isolated HA immobilised on the SPR chip surface. The desired immobilisation level is achieved by varying contact time. The remaining reactive groups are blocked by ethanolamine-HCl. Mock-derivatised flow cells serve as reference surfaces. The binding analyses are typically performed at 10 and 25° C. Glycans or anti-adhesion molecules are prepared for binding analysis by 2-fold serial dilution to obtain an appropriate concentration range (0.01-10 μM) over a low-density immobilisation surface of recombinant protein (3000 RU). The synthetic anti-adhesives can also be assayed for their ability to inhibit natural glycan-HA interactions using SPR.

Example 14

Therapeutics for the Inhibition of Influenza

The effectiveness of the glycomimetics described herein in preventing or minimizing influenza infection will be tested. Any of many available models systems may be used, including, but not limited to mouse and ferret animal model systems. Ferret is an excellent small animal model for influenza virus infection. There is a remarkable similarity in the lung physiology and morphology between ferrets and humans. Ferrets are highly susceptible to infection with influenza viruses.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A glycomimetic compound having the formula of Type III

Type III 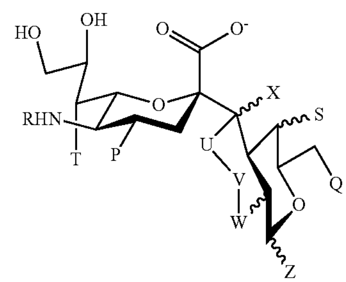 and pharmaceutically acceptable salts thereof, wherein

P is independently selected from the group consisting of a halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, $C_6$-$C_{20}$ aryl ester, $OCH_3$, OBenzyl, and OCyclohexyl;

Q is independently selected from the group consisting of a halogen, OH, $CF_3$, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and $C_6$-$C_{20}$ aryl ester;

R is independently selected from H, $C_1$-$C_5$ aliphatic ester, Ac ($CH_3C{=}O$), $C(O)CF_3$, triazole, and azide;

S is independently selected from the group consisting of an axial or equatorial halogen, OH, H, $C_1$-$C_5$ aliphatic ether, $C_1$-$C_5$ aliphatic thioether, $NH_2$, $C_1$-$C_5$ aliphatic amine, $C_1$-$C_6$ aryl amine, $C_5$-$C_{10}$ aryl ether, $C_1$-$C_{20}$ aliphatic ester, and $C_6$-$C_{20}$ aryl ester;

T is independently selected from the group consisting of a halogen, OH, H, $C_1$-$C_5$ aliphatic ether, $C_1$-$C_5$ aliphatic thioether, $NH_2$, $C_1$-$C_5$ aliphatic amine, $C_1$-$C_5$ aryl amine, $C_5$-$C_{10}$ aryl ether, $C_1$-$C_{20}$ aliphatic ester, and $C_6$-$C_{20}$ aryl ester;

U is independently selected from $C_1$-$C_5$ aliphatic, O, NH, S, and $C_1$-$C_5$ aliphatic amine;

V is independently selected from a $C_1$-$C_5$ aliphatic;

W is independently selected from $C_1$-$C_5$ aliphatic, O, NH, S, and $C_1$-$C_5$ aliphatic amine;

X is independently selected from H, OH, halogen $C_1$-$C_5$ aliphatic ester, $C_1$-$C_5$ aliphatic ether, $C_5$-$C_{10}$ arylether, $C_1$-$C_{20}$ aliphatic ester, $C_6$-$C_{20}$ aryl ester, $OCH_3$, OBenzyl, and OCyclohexyl;

Z is independently selected from $C_1$-$C_5$ aliphatic, $C_1$-$C_{20}$ aryl, $C_1$-$C_{20}$ aliphatic ether, $C_1$-$C_{10}$ aliphatic thioether, NH$_2$, C$_1$-C$_5$ aliphatic amine, C$_1$-C$_5$ aryl amine, C$_1$-C$_{20}$ aliphatic ester, C$_6$-C$_{20}$ aryl ether, and a monosaccharide.

2. The glycomimetic compound of claim 1, wherein P is selected from H, OH, halogen, C$_1$-C$_5$ aliphatic ester, C$_1$-C$_5$ aliphatic ether, C$_5$-C$_{10}$ arylether, C$_1$-C$_{20}$ aliphatic ester, C$_6$-C$_{20}$ aryl ester, OCH$_3$, OBenzyl, and OCyclohexyl; U is O or CH$_2$; V=CH$_2$; W=NH; X=H; Z=OCH$_3$; S=axial OH; R=Ac (CH$_3$C=O); T=OH; and Q=OH.

3. The glycomimetic compound of claim 1, wherein U is O or CH$_2$; and V is selected from a C$_1$-C$_5$ aliphatic.

4. The glycomimetic compound of claim 3, wherein W is selected from C$_1$-C$_5$ aliphatic, O, NH, S, and a C$_1$-C$_5$ aliphatic amine.

5. The glycomimetic compound of claim 4, wherein W=O.

6. The glycomimetic compound of claim 4, wherein U=O or CH$_2$; V=CH$_2$; W=O; X=H; S=axial OH; R=Ac (CH$_3$C=O); T=OH; Q=OH; Z=OCH$_3$; and P=OH.

7. The glycomimetic compound of claim 6, wherein U=O.

8. The glycomimetic compound of claim 6, wherein U=CH$_2$.

9. The glycomimetic of claim 1, wherein the monosaccharide is selected from the group consisting of glucose, mannose, galactose, GlcNAc, GalNAc, and ManNAc.

10. The glycomimetic of claim 1, wherein the glycomimetic inhibits the binding of a pathogen to cell surface sialylated galactose.

11. The glycomimetic of claim 10, wherein the cell surface sialylated galactose comprises a terminal NeuSAc-α-(2-3)-Gal.

12. The glycomimetic of claim 10, wherein the pathogen is BK virus, *H. pylori, S. pneumoniae, M. pneumoniae, E. coli, N. meningitides, T. gondii* or influenza A.

13. A composition comprising a glycomimetic of claim 1.

14. The composition of claim 13 formulated for oral, topical, mucosal, parenteral, or aerosol administration.

15. The composition of claim 13 formulated for impregnating filters, masks, clothing, and/or an indwelling medical device.

16. A method of impregnating an article, the method comprising contacting the article with a glycomimetic of claim 1.

17. An article impregnated with a glycomimetic of claim 1.

18. The article of claim 17, wherein the article is a filter, mask, an article of clothing, or an in dwelling medical device.

19. A method of impregnating an article, the method comprising contacting the article with a composition of claim 13.

20. An article impregnated with a composition of claim 13.

21. The article of claim 20, wherein the article is a filter, mask, an article of clothing, or an in dwelling medical device.

* * * * *

UNITED STATES PATENT AND TRADEMARK OFFICE
CERTIFICATE OF CORRECTION

PATENT NO. : 9,605,014 B2
APPLICATION NO. : 14/385312
DATED : March 28, 2017
INVENTOR(S) : Woods et al.

It is certified that error appears in the above-identified patent and that said Letters Patent is hereby corrected as shown below:

In the Specification

Column 48, Scheme 1, delete Scheme 1. Insert therefore:

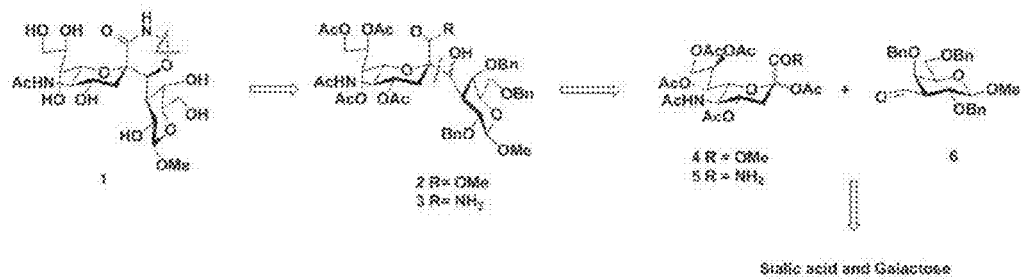

Column 49, Scheme 2, delete the text next to Compound 11. Insert therefore:

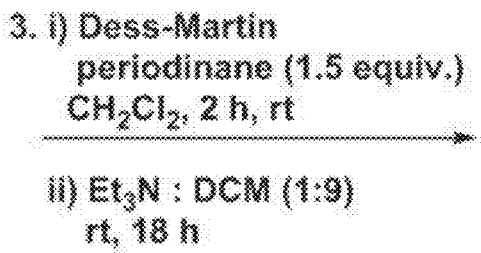

Signed and Sealed this
Fifth Day of December, 2017

Joseph Matal
*Performing the Functions and Duties of the
Under Secretary of Commerce for Intellectual Property and
Director of the United States Patent and Trademark Office*

Column 51 and 52, Scheme 4, delete Compound 15. Insert therefore:
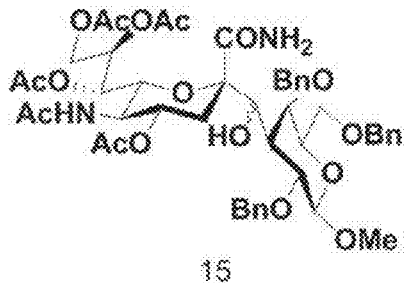
Column 55, Scheme 7, delete Compound 16. Insert therefore:
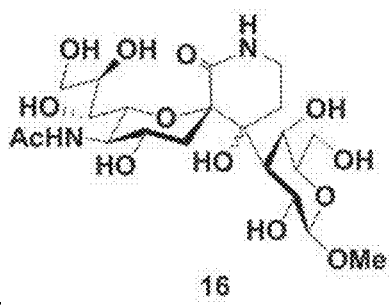
Column 60, Scheme 10, delete Compound 23. Insert therefore:
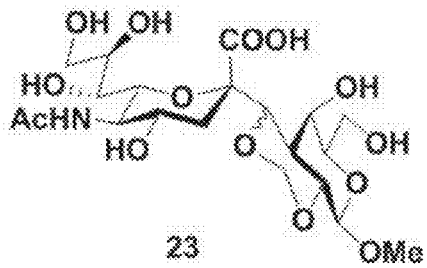
Column 60, Scheme 11, delete Compound 42. Insert therefore:
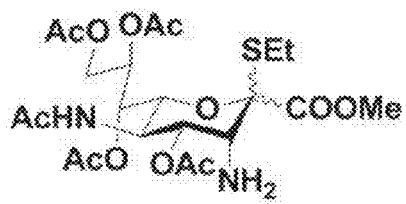

Column 61, Scheme 13, delete Compound 9. Insert therefore:

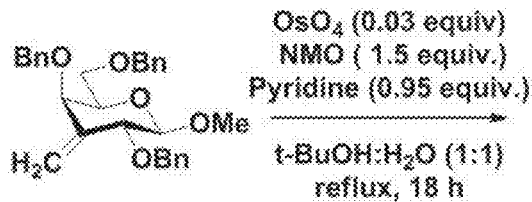

-- 9 --

In the Claims

Column 69, Claim 6, delete "wherein U = O or CH$_2$; V = CH$_2$; W = O; X = H; S = axial OH; R = Ac (CH$_3$C=O); T = OH; Q = OH; Z = OCH$_3$; and P = OH." and insert -- wherein U = CH$_2$. --

Column 69, Claim 8, delete "wherein U = CH$_2$" and insert -- wherein U = O or CH$_2$; V = CH$_2$; W = O; X = H; S = axial OH; R = Ac (CH$_3$C=O); T = OH; Q = OH; Z = OCH$_3$; and P = OH. --

Column 70, Claim 11, delete "NeuSAc-α-(2-3)-Gal." and insert -- Neu5Ac-α-(2-3)-Gal. --